(12) United States Patent
Moreno

(10) Patent No.: US 11,386,803 B1
(45) Date of Patent: Jul. 12, 2022

(54) COGNITIVE TRAINING SYSTEM AND METHOD

(71) Applicant: Sylvain Jean-Pierre Daniel Moreno, Ontario (CA)

(72) Inventor: Sylvain Jean-Pierre Daniel Moreno, Ontario (CA)

( * ) Notice: Subject to any disclaimer, the term of this patent is extended or adjusted under 35 U.S.C. 154(b) by 0 days.

(21) Appl. No.: 15/864,294

(22) Filed: Jan. 8, 2018

Related U.S. Application Data

(63) Continuation of application No. 14/017,493, filed on Sep. 4, 2013, now Pat. No. 9,881,515, which is a continuation-in-part of application No. 13/090,677, filed on Apr. 20, 2011, now Pat. No. 8,536,436.

(60) Provisional application No. 61/325,918, filed on Apr. 20, 2010.

(51) Int. Cl.
*G09B 19/00* (2006.01)
*G09B 15/00* (2006.01)
*G09B 7/02* (2006.01)

(52) U.S. Cl.
CPC ............... *G09B 19/00* (2013.01); *G09B 7/02* (2013.01); *G09B 15/00* (2013.01)

(58) Field of Classification Search
CPC .................................................... G09B 19/00
USPC ......................................................... 434/236
See application file for complete search history.

(56) References Cited

U.S. PATENT DOCUMENTS

| | | | |
|---|---|---|---|
| 2,447,213 A | 8/1948 | Sledge | |
| 3,733,957 A | 5/1973 | Peirano et al. | |
| 3,919,913 A | 11/1975 | Shrader | |
| 4,307,645 A | 12/1981 | Rauchi | |
| 4,321,853 A | 3/1982 | Tumblin | |
| 4,331,061 A | 5/1982 | Morgando | |
| 4,364,299 A | 12/1982 | Nakada et al. | |
| 4,399,731 A | 8/1983 | Aoki | |

(Continued)

OTHER PUBLICATIONS

Moreno et al. "Short-term music training enhances verbal intelligence and executive function." Psychol. Sci. vol. 22, No. 11 (Nov. 2011), pp. 1425-1433. doi: 10.1177/0956797611416999.

(Continued)

*Primary Examiner* — Kesha Frisby
(74) *Attorney, Agent, or Firm* — Rosenberg, Klein & Lee

(57) ABSTRACT

A cognitive training method having a processor to store exercise category data which has a number of task data, each of the task data including levels of difficulty. There is included a visual display and an audio transducer and a user interfaces actuated to accept user data in response to a selected task. The user data is sent from the user interface to the processor and the processor stores and evaluates the user input data and based upon evaluation of the user input data, adjusts a subsequent level of difficulty associated with a selected task. If user input data is above a correct data threshold, the level of difficulty may be adjusted responsive to an evaluation of the user input data. Values of training parameters are adjusted at least partially in accordance with stored user parameters, and there is transmitted to the user interface and to the user adjusted values of exercise and training parameters where at least one training task is selected to include a cue stimulus, a probe stimulus, and a distractor stimulus. A task difficulty is adjusted by selectively adjusting the task difficulty of the cue stimulus difficulty, the difficulty of the probe stimulus, and difficulty of the distractor stimulus.

21 Claims, 34 Drawing Sheets

(56) References Cited

U.S. PATENT DOCUMENTS

| | | | |
|---|---|---|---|
| 4,416,182 A | 11/1983 | Wise et al. | |
| 4,781,099 A | 11/1988 | Koike | |
| 4,832,605 A | 5/1989 | Bragin | |
| 5,038,662 A | 8/1991 | Ho | |
| 5,145,447 A | 9/1992 | Goldfarb | |
| 5,183,398 A | 2/1993 | Monte et al. | |
| 5,270,475 A | 12/1993 | Weiss et al. | |
| 5,287,789 A | 2/1994 | Zimmerman | |
| 5,496,179 A | 3/1996 | Hoffman | |
| 5,529,498 A | 6/1996 | Cassily et al. | |
| 5,540,132 A | 7/1996 | Hale | |
| 5,563,358 A | 10/1996 | Zimmerman | |
| 5,746,605 A | 5/1998 | Kennedy | |
| 5,906,494 A | 5/1999 | Ogawa et al. | |
| 6,057,501 A | 5/2000 | Hale | |
| 6,072,113 A | 6/2000 | Tohgi et al. | |
| 6,211,451 B1 | 4/2001 | Tohgi et al. | |
| 6,323,410 B1 | 11/2001 | Rackow | |
| 6,346,666 B1 | 2/2002 | Tsai et al. | |
| 6,353,168 B1 | 3/2002 | Sosoka et al. | |
| 6,417,435 B2 | 7/2002 | Chantzis et al. | |
| 6,464,508 B1 | 10/2002 | Ryan | |
| 6,504,090 B2 | 1/2003 | Tsai et al. | |
| 6,716,031 B2 | 4/2004 | Wood et al. | |
| 6,751,439 B2 | 6/2004 | Tice et al. | |
| 6,835,887 B2 | 12/2004 | Devecka | |
| 6,870,085 B2 | 3/2005 | MacCutcheon | |
| 7,122,004 B1 | 10/2006 | Cassily | |
| 7,199,298 B2 | 4/2007 | Funaki | |
| 7,271,329 B2 | 9/2007 | Franzblau | |
| 7,288,705 B1 | 10/2007 | Nelson | |
| 7,323,629 B2 | 1/2008 | Somani | |
| 7,332,664 B2 | 2/2008 | Yung | |
| 7,435,891 B2 | 10/2008 | Perla | |
| 7,465,864 B2 | 12/2008 | Heintz | |
| 7,507,892 B1 | 3/2009 | Wissen | |
| 7,525,035 B2 | 4/2009 | Katsuta | |
| 7,579,541 B2 | 8/2009 | Guldi | |
| 7,663,044 B2 | 2/2010 | Katsuta | |
| 7,667,120 B2 | 2/2010 | Suriano | |
| 7,772,480 B2 | 8/2010 | Brennan | |
| 7,806,759 B2 | 10/2010 | McHale et al. | |
| 7,919,705 B2 | 4/2011 | Miller | |
| 7,989,689 B2 | 8/2011 | Sitrick et al. | |
| 8,148,621 B2 | 4/2012 | Bright et al. | |
| 8,242,344 B2 | 8/2012 | Moffatt | |
| 8,273,973 B2 | 9/2012 | Kimmons et al. | |
| 8,319,083 B2 | 11/2012 | Adams | |
| 2001/0008100 A1 | 7/2001 | Devecka | |
| 2001/0011496 A1 | 8/2001 | Mishima et al. | |
| 2001/0029829 A1 | 10/2001 | Moe | |
| 2001/0029830 A1 | 10/2001 | Rosen | |
| 2001/0032539 A1 | 10/2001 | Chantzis et al. | |
| 2001/0045156 A1 | 11/2001 | Mishima | |
| 2002/0002899 A1 | 1/2002 | Gjerdingen et al. | |
| 2002/0004191 A1 | 1/2002 | Tice et al. | |
| 2002/0035916 A1 | 3/2002 | Tice et al. | |
| 2002/0043149 A1 | 4/2002 | Barlay | |
| 2002/0088337 A1 | 7/2002 | Devecka | |
| 2003/0118975 A1 | 6/2003 | Stamm et al. | |
| 2003/0207239 A1 | 11/2003 | Langlois | |
| 2005/0061140 A1 | 3/2005 | Vallery | |
| 2005/0153263 A1* | 7/2005 | De Ley | G09B 5/00 434/169 |
| 2005/0153267 A1* | 7/2005 | Goldman | G09B 7/00 434/308 |
| 2005/0262989 A1 | 12/2005 | Franzblau | |
| 2006/0107819 A1 | 5/2006 | Salter | |
| 2006/0141425 A1 | 6/2006 | De Ley et al. | |
| 2006/0196343 A1 | 9/2006 | Yung | |
| 2006/0199157 A1 | 9/2006 | Stamm et al. | |
| 2006/0288842 A1 | 12/2006 | Sitrick et al. | |
| 2006/0292529 A1 | 12/2006 | De Ley et al. | |
| 2007/0017351 A1 | 1/2007 | Aruffo | |
| 2007/0022866 A1 | 2/2007 | Perla | |
| 2007/0039450 A1 | 2/2007 | Ohshima et al. | |
| 2007/0065789 A1 | 3/2007 | Goldman et al. | |
| 2007/0134635 A1 | 6/2007 | Hardy et al. | |
| 2007/0141541 A1 | 6/2007 | Chan et al. | |
| 2007/0227339 A1 | 10/2007 | Suriano | |
| 2007/0288411 A1* | 12/2007 | Jenkins | G09B 5/02 706/45 |
| 2008/0003558 A1 | 1/2008 | Chan et al. | |
| 2008/0060499 A1 | 3/2008 | Sitrick | |
| 2008/0078281 A1 | 4/2008 | Katsuta | |
| 2008/0087160 A1 | 4/2008 | Gabert | |
| 2008/0133816 A1* | 6/2008 | Hurling | G06F 3/011 711/100 |
| 2008/0134861 A1 | 6/2008 | Pearson | |
| 2008/0271591 A1 | 11/2008 | Lemons | |
| 2009/0038468 A1 | 2/2009 | Brennan | |
| 2009/0069707 A1 | 3/2009 | Sandford | |
| 2009/0226860 A1 | 9/2009 | Garcia et al. | |
| 2010/0005952 A1 | 1/2010 | LaMon | |
| 2010/0011938 A1 | 1/2010 | Adams | |
| 2010/0077906 A1 | 4/2010 | Hagstrom | |
| 2010/0089221 A1 | 4/2010 | Miller | |
| 2010/0095828 A1 | 4/2010 | Adams | |
| 2010/0159426 A1 | 6/2010 | Ben-Haim et al. | |
| 2010/0192752 A1 | 8/2010 | Bright et al. | |
| 2010/0233661 A1 | 9/2010 | Franzblau | |
| 2010/0242709 A1 | 9/2010 | Salter | |
| 2010/0313736 A1 | 12/2010 | Lenz | |
| 2011/0041671 A1 | 2/2011 | Moffatt | |
| 2011/0094365 A1 | 4/2011 | Kimmons et al. | |
| 2011/0185879 A1 | 8/2011 | Cole | |
| 2011/0256520 A1 | 10/2011 | Siefert | |
| 2011/0283866 A1 | 11/2011 | Hogan | |
| 2011/0318721 A2 | 12/2011 | Kespy-Yahi | |
| 2012/0090446 A1 | 4/2012 | Moreno | |
| 2013/0216985 A1* | 8/2013 | de Villers-Sidani | G09B 19/00 434/236 |

OTHER PUBLICATIONS

Forgeard et al. "The relation between music and phonological processing in normal-reading children and children with dyslexia." Music Perception vol. 25, No. 4 (Apr. 2008), pp. 383-390. doi: 10.1525/mp.2008.25.4.383.

Overy. "Dyslexia and music: From timing deficits to musical intervention." Ann, N.Y. Acad. Sci. vol. 999, No. 1 (Nov. 2003), pp. 497-505. doi; 10.1196/annals.1284.060.

Schlaug et al. "In vivo evidence of structural brain asymmetry in musicians." Science vol. 267, No. 5198 (Feb. 3, 1995), pp. 699-701.

\* cited by examiner

| | Rhythm | Voice Awareness | Musical Ear | Theory | Musical Product | Creativity |
|---|---|---|---|---|---|---|
| Pond: Lesson 1 – 3 | Animal Walking 1 (RE1) | Story module | Animal Noises 1 | Name the animals 1 | Songs 1 &2 | Drawing the animals 1 |
| Lesson 4 -6 | Animal Walking 2 (RE1) | Mime 1 Turtle | Animal Noises 2 | Name the animals 2 | Songs 1 &2 | Drawing the animals 2 |
| Lesson 7 - 9 | Animal Walking 3 (RE1) | Mime 1 " | Animal Noises 3 | Name the animals 3 | Songs 1 &2 | Drawing the animals 3 |
| Pond Forest: Lesson 10 – 12 | Jump Jump Stop! 1 (RE2) | Mime 2 Monkey | Animal Calls 1 | Animal Stacking 1 | Songs 3 & 4 | Animal Shapes/ Puzzles 1 |
| Lesson 13 -15 | Jump Jump Stop! 2 (RE2) | Mime 2 " | Animal Calls 2 | Animal Stacking 2 | Songs 3 & 4 | Animal Shapes/ Puzzles 2 |
| Lesson 16 – 18 | Jump Jump Stop! 3 (RE2) | Mime 3 Cat | Animal Calls 3 | Animal Stacking 3 | Songs 3 & 4 | Animal Shapes/ Puzzles 3 |
| Forest: Lesson 19 – 21 | Slow Med. Fast! 1 (RE3) | Mime 3 " | Three in a Row 1 | Lines and spaces 1 | Songs 5 & 6 | Picture to Music 1 |
| Lesson 22 – 24 | Slow Med. Fast! 2 (RE3) | Mime 4 Anteater | Three in a Row 2 | Lines and spaces 2 | Songs 5 & 6 | Picture to Music 2 |
| Lesson 25 – 27 | Slow Med. Fast! 3 (RE3) | Mime 4 " | Three in a Row 3 | Lines and spaces 3 | Songs 5 & 6 | Picture to Music 3 |
| Temple: Lesson 28 – 30 | Feel the beat 1 (RE4) | Mime 5 " Hippo | Animal Calls 4 | Name the animals 4 | Songs 7 & 8 | Animal Shapes/ Puzzles 4 |
| Lesson 31- 33 | Feel the beat 2 (RE4) | Mime 5 " | Animal Calls 5 | Name the animals 5 | Songs 7 & 8 | Animal Shapes/ Puzzles 5 |
| Lesson 34 – 36 | Feel the beat 3 (RE4) | Mime 6 Elephant | Animal Calls 6 | Name the animals 6 | Songs 7 & 8 | Animal Shapes/ Puzzles 6 |
| Jungle: Lesson 37-39 | Animal Dance 1 (RE5) | Mime 6 " | Three in a Row 4 | Place the Animals 1 | Songs 9 & 10 | Drawing Music 1 |
| Lesson 40-42 | Animal Dance 2 (RE5) | Mime 7 " Giraffe | Three in a Row 5 | Place the Animals 2 | Songs 9 & 10 | Drawing Music 2 |
| Lesson 43-45 | Animal Dance 3 (RE5) | Mime 7" | Three in a Row 6 | Place the Animals 3 | Songs 9 & 10 | Drawing Music 3 |
| Farm: Lesson 46-48 | Body Rhythm 1 (RE6) | Mime 8 Bird | Tone Race 1 | Lines and Spaces 4 | Songs 11 & 12 | Moving to Music 1 |
| Lesson 49-51 | Body Rhythm 2 (RE6) | Mime 8" | Tone Race 2 | Lines and Spaces 5 | Songs 11 & 12 | Moving to Music 2 |
| Lesson 52-54 | Body Rhythm 3 (RE6) | Mime 1 " | Tone Race 3 | Lines and Spaces 6 | Songs 11 & 12 | Moving to Music 3 |
| City: Lesson 55-57 | Rhythm Building 1 (RE7) | Mime 2 | Match the Bells 1 | Animal Follow 1 | Songs 13 & 14 | Compose a song 1 |
| Lesson 58-60 | Rhythm Building 2 (RE7) | Mime 3 " | Match the Bells 2 | Animal Follow 2 | Songs 13 & 14 | Compose a song 2 |
| Lesson 61-63 | Rhythm Building 3 (RE7) | Mime 4 " | Match the Bells 3 | Animal Follow 3 | Songs 13 & 14 | Compose a song 3 |
| Party Room: Lesson 64-66 | Body Rhythm 4 (RE8) | Mime 5 | Tone Race 4 | Place the Animals 4 | Songs 15 & 16 | Drawing Music 4 |
| Lesson 67-69 | Body Rhythm 5 (RE8) | Mime 6 | Tone Race 5 | Place the Animals 5 | Songs 15 & 16 | Drawing Music 5 |
| Lesson 70-72 | Body Rhythm 6 (RE8) | Mime 7 " | Tone Race 6 | Place the Animals 6 | Songs 15 & 16 | Drawing Music 6 |
| Theatre: Lesson 73-75 | Rhythm Building 4 | Mime 8 " | Match the Bells 4 | Animal Follow 4 | Songs 17 & 18 | Compose a song 4 |
| Lesson 76-78 | Rhythm Building 5 | Mime 1 & 2 | Match the Bells 5 | Animal Follow 5 | Songs 17 & 18 | Compose a song 5 |
| Lesson 79-81 | Rhythm Building 6 | Mime 3 & 4 | Match the Bells 6 | Animal Follow 6 | Songs 17 & 18 | Compose a song 6 |
| Stage: Lesson 82-84 | Rhythm Review 1 | Mime 5 &6 | Ear Review 1 | Theory Review 1 | Pick a Song 1-6 | Creative Review 1 |
| Lesson 85-87 | Rhythm Review 2 | Mime 7 & 8 | Ear Review 2 | Theory Review 2 | Pick a Song 7-12 | Creative Review 2 |
| Lesson 88-90 | Rhythm Review 3 | Mime Review 1 - 8 | Ear Review 3 | Theory Review 3 | Pick a Song 13-18 | Creative Review 3 |

FIG. 10

| | |
|---|---|
| 440 | Start Game |
| 442 | Operate user information Module:<br>Enter User information (used to track user performance) |
| | Operate story module:<br>Show a cartoon associated with the levels |
| 574 | Operate training Module:<br>Present all 6 categories of exercises at a particular level (e.g., one after the other - 6 in each lesson)<br>Once 3 repetitions or a certain level of performance is reached for all the exercise, the user moves onto the next lesson (e.g., Fig. 10)<br>After each exercise, a series of questions will test the user learning. |
| 444 | Operate user assessment Module:<br>Obtain all statistics related to the training and save for the user |
| 446 | Operate interactive map:<br>Show interactive map with levels and translate the performance onto a spatial position (e.g., higher level = higher performance) |

FIG. 35

COGNITIVE TRAINING SYSTEM AND METHOD

RELATED PATENT APPLICATIONS

This is a continuation of U.S. patent application Ser. No. 14/017,493, filed on Sep. 4, 2013, entitled "Cognitive Training System and Method", which is a Continuation-In-Part Application of U.S. patent application Ser. No. 13/090,677, filed on Apr. 20, 2011, entitled "System and Method For Providing Music Based Cognitive Skills Development", now U.S. Pat. No. 8,536,436, issued on Sep. 17, 2013, which is based upon Provisional Application No. 61/325,918, filed on Apr. 20, 2010

FIELD OF THE INVENTION

The present invention relates to programs for training a human subject and in particular to systems and methods of increasing cognitive capabilities.

BACKGROUND OF THE INVENTION

Over the past several years scientists have consistently shown that formal musical training, such as Teaming to play an instrument, can improve cognitive performance. At the behavioral level, music expertise or training is associated with improved performance in other cognitive domains such as language, attention, intelligence and motor skills. These "positive transfers" are possibly explained by findings which show that music training modifies brain areas related to various cognitive skills. This may be especially true in regions responsible for language, namely, planum temporale, Heschl's gyms and the inferior frontal gyms. Similar to language, music is a symbolic representation of meaning and requires time-frequency processing by the auditory system, deconstruction of sounds into components, and auditory discrimination for words transmitted vocally.

Previous work has identified several factors that may be responsible for reading and language impairment (LI) in children with low intelligence. Various auditory-processing deficits, related to both temporal and pitch information, have been implicated. Impaired pitch processing within natural speech may contribute to deficient phonological representations in LI children that may, in turn, lead to a deficit in reading skills. It has been demonstrated that audio-visual training improved the level of performance of LI children, and normalized their brain wave activity associated with language processing.

A landmark study by Dr. Overy (Overy, 2003) found that a musical remediation program with LI children showed a positive effect of musical training on both phonologic and spelling skills. This study supports the rehabilitative potential of musical training Forgeard et al. (2008) conducted a longitudinal study with normal-reading children and a pilot study with LI children. Their results indicated a strong association between musical discrimination abilities and language-related skills. In children with LI, musical discrimination predicted phonological skills, which in turn predicted reading ability. Taken together, the findings of Forgeard and Overy suggest that music intervention that successfully strengthens basic skills of auditory perception in children with language impairments may also remediate some of their language deficits.

Brain imaging can show brain areas that are influenced by music stimuli and tasks. Structural MRI studies have shown anatomical differences between the brains of musicians and non-musicians. For example, a study by Schlaug et al. (1995) showed a link between musical expertise and structural changes in the brain. The study explored whether the mid-sagittal area of the corpus callosum, which is involved in the coordination of movement, is influenced by musical expertise (in this case, in keyboard or string instrument players). Results showed a significantly larger anterior portion of the corpus callosum in musicians than in non-musicians. Early and intensive training in keyboard and string players may facilitate increased and faster communication between the brain's hemispheres in order to perform complex movements with both hands.

Other studies have also demonstrated structural differences between musicians and non-musicians' brains, finding significant differences in the planum temporale (related to verbal memory processing and absolute pitch), the posterior band of the precentral gyrus (related to motor processing), the corpus callosum (related to cross-hemisphere communication), the anterior-medial region of Heschl's gyms (related to auditory processing), the inferior frontal gyrus (related to executive functions such as attention and language), the inferior lateral temporal lobe (related to auditory processing) and parts of the cerebellum (related to motor processing).

These brain areas are involved both in skills related to music processing and are also relevant to skills that are related to language, memory, auditory detection and discrimination processing, and other skills that are central to many sensory and cognitive processes of more generalized tasks. Cognitive training that relies upon music-related exercises should also benefit non-musical cognitive skills.

Traditional training that is intended to assist a user master playing a particular musical instrument may be beneficial, but may require years of effort in order to realize proficiency. Learning to play a musical instrument may be frustrating, expensive, and require attention and commitment that exceeds many users, especially young children.

The current invention can provide advantages over other types of training, such as traditional training on an instrument. By being designed to provide sensory and cognitive training with music-based exercises which are designed to focus on practice of particular skills related to, for example, attention, sound discrimination, sound template matching, and auditory memory, users may efficiently obtain generalized sensory and cognitive benefits. The training may produce larger benefits than music lessons because it is designed to be more engaging, fun and entertaining, to the user while reducing potential levels of frustration. The intention of the current invention training is to leverage positive transfer to provide sensory and cognitive training to users with these and other advantages, as will be described.

SUMMARY OF THE INVENTION

In one embodiment, the training of the present invention may be implemented in a video game format that is designed to provide music-based exercises to a user. This format provides advantages for cognitive training in that it is designed to be easier and more entertaining, engaging, and non-frustrating than traditional music training. The training avoids the tedious repetition of the same training task that often accompanies learning to play a musical instrument and also avoids emphasizing music production. It is an object of the invention to avoid focusing upon the manual dexterity component of music related to music production to make the training more fun and engaging.

It is an advantage of the current invention to dissociate the skill of playing an instrument from the difficulty level of a music-based task of the training. For example, in music training a person may not be required to remember and play longer pieces of music until they have mastered playing shorter pieces (and may be required to remember relatively less if sheet music is used). The current training dissociates cognitive difficulty from sensory-motor ability since task difficulty is not tied to performing musical pieces. Memory exercises can be provided without any music being played. By modulating characteristics such as the number of stimuli that are shown to a user, the number of items a user must store in memory can be easily increased.

It is an object of the invention to avoid drawing upon several musical skills simultaneously, as may occur when a musician performs or learns to play an instrument. The current training exercises often focus independently upon a particular skill or small set of skills (e.g., auditory discrimination, auditory template matching, abstract representation of musical concepts, relationships between symbolic concepts and sounds or values, etc). Providing training which focuses upon a limited set of particular skills enables the user to attend to a particular skill. Further, this approach allows a user to be presented with a task which engages a skill that might not typically be encountered until later years of music training.

In one aspect of the invention, a music-based cognitive exercise may be designed in order to train and improve a particular aspect, or several aspects, of sensory or cognition processing. For example, in one exercise a user may be shown two or more audiovisual cue stimuli (each visual cue is paired with a distinct musical sound cue). The user is then shown two or more visual probes (e.g., a set of animal characters are shown on a computer display). The user is then presented with a sound probe and is asked to select which visual probe is a correct match for the sound probe (e.g., "can you choose the animal that made that sound?"). This exercise requires that a user match the sound probe to prior memories of an audiovisual cue, in order to select the correct visual probe. This task may specifically train various types of sensory processing (e.g. auditory discrimination) and cognitive skills such as memory (e.g., working auditory memory) processing that may not be typically focused upon, either individually or in combination with other skills, during traditional music training. For example, simply playing a violin may not provide for simple and focused matching of an auditory probe to previously presented sound or audiovisual templates.

It is a further object of the invention to avoid monotony, by alternating between a selected set of exercise categories to provide a variety of training tasks to a user over relatively short intervals.

In another aspect of the invention, the exercises may be made relatively fun for children by using animated animal characters, each of which may be paired with a unique music-related characteristic. The characteristic may be a particular sound or set of sounds, and moving to a particular rhythm, beat, or tempo.

In another aspect of the invention, the training may present to a user cartoons and stories that introduce stimuli, stimulus pairings (e.g., associating an animal and particular sound), audio-visual associations, concepts and skills that are evaluated during the exercises. The cartoon and video game format of the training, game-like aspects of many of the training tasks, and animated stories that reinforce associations which are tested, are an advantage of the invention since information is introduced and reinforced in a manner that is intended to seem more like a game and less like schoolwork or training.

It is a further object of the invention to provide training that can serve to exercise selective attention and auditory discrimination (cognitive and sensory filtering of non-relevant stimuli). For example, in a further embodiment of the invention, training stimuli are presented against a distracting auditory or visual background.

It is a further object of the invention to provide training which exercises brain areas common to many cognitive processes and language production, so the training generalizes to other cognitive domains such as reading, attention, etc.

In this respect, before explaining at least one embodiment of the invention in detail, it is to be understood that the invention is not limited in its application to the details of construction and to the arrangements of the components set forth in the following description or illustrated in the drawings. Components in the drawings may be implemented in other orders or configurations, and steps of illustrated methods may be omitted, repeated, or contingently invoked in some embodiments of the invention. Any particular step may be operated in isolation, in a different order, or with only a subset of other steps shown. Any titles, headings, or subheadings used herein are for descriptive, clarification purposes only and are not intended to limit the invention in any manner. Modules and steps shown in a particular figure may be used in other figures, but all variations have not been shown to avoid cluttering of the figures. The invention is capable of other embodiments and of being practiced and carried out in various manners. Also, it is to be understood that the phraseology and terminology employed herein are for the purpose of description and should not be regarded as limiting.

BRIEF DESCRIPTION OF THE DRAWINGS

The invention and its objects will be better understood when consideration is given to the following detailed description and associated figures.

FIG. 10 is a table depicting an example of a curriculum implemented in the curriculum mode as well as a default order of lessons, each containing an exercise from the different exercise categories;

FIG. 35 is a table showing the exemplary steps of a method of one embodiment of the present invention;

The description, embodiments of the invention, and drawings are for exemplarily illustration and are not intended as a definition of the limits of the invention.

DETAILED DESCRIPTION OF THE INVENTION

Platform Overview.

Figure 1:
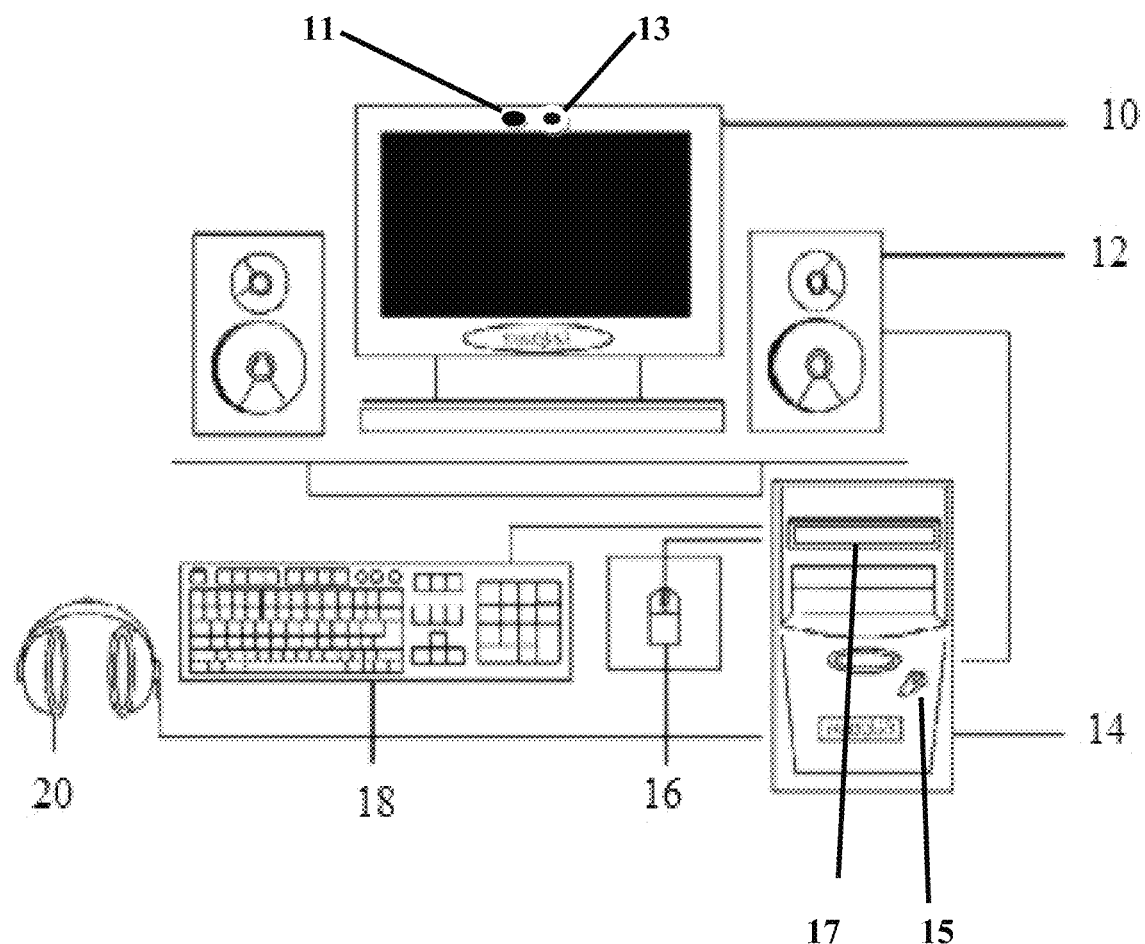
FIG. 1 is a general diagram of a computer system schematically represented and used to implement the training for a user.

Referring now to FIG. 1, there is shown a system of the present invention which is intended for use by a single user, or up to a few users who may participate either sequentially or jointly in the training. A device 14 may be a conventional personal computer. For example, a personal computer with at least the following elements: any Operating System, although at least a 32-bit system may be preferred; a Processor operating at a minimum of 1.6 GHz; Memory that is at least 2 GB; a Hard Drive that is at least 80 GB; optical drive 17, and one or more External Ports 15 that may include a USB port, ethernet port, and/or other ports. A microphone 11 and webcam 13 may serve as a user interface to allow recording and measurement of user behavioral response. User input can also be obtained by various devices and controllers that communicate with the device 14 though a port 15 or wirelessly. Wireless connectivity is also helpful when the training is implemented over the internet in conjunction with a server configured to provide the training. The device 14 on which the training platform is wholly or partially realized may also be a laptop, video game console, gaining platform, an e-reader, a tablet, smartphone, an interactive book, a TV with wireless access, a video presentation (such as a television (TV) show, which may also have means for accepting user input through a port or wirelessly), or a website. Regardless of device 14, the training platform will often be provided with access to the internet, webcams, microphones, motion sensors, and other accessories that may be used by the training. The system of the present invention may further include any of the following: a video display 10 which may be touch sensitive; one or more sound or audio transducers such as speakers 12 or headphones 20; an input device such as mouse 16; and a touchpad or keyboard 18 all of which can be connected using wired or wireless means.

The device 14 on which the training platform is realized should include a computer program product including computer instructions. The computer instructions may define a music based cognitive training utility. The music based cognitive training utility may include a series of training components, for example, exercises selected from two or more exercise categories. The computer instructions may be supplied by video-game software that may be implemented on a DVD, software residing on the device 14 or over the internet. The computer instructions may also be implemented on any device 14 such as a video-game console such as Wii.™, or an a hand-held smart-phone, or on a customized portable device which allows user input in the form of key-presses or by direct measurement of a person's behavior and vocalization using a web-camera, microphone, and/or movement sensors. In some embodiments of the present invention it may not be required for a user to provide responses to some or all of the training components, or at least the response isn't measured. For example, aspects of the training can be realized as a video presentation, such as a TV show or cartoon. Additionally, in one embodiment some exercises are presented in an interactive mode, via classroom or computer based training, and other parts of the training, such as story mode modules 32, are presented as part of a TV show which reinforces the training.

In one embodiment, the training is provided to the user in a variety of manners. For example, the training may present a particular order of default exercises, lessons and/or modules to a user. In this case, the user does not select choices about the order of the exercises, lessons or modules of the training. In other embodiments of the present invention a user may be able to make specific choices, including the difficulty level or order of exercises, lesson and/or modules to be viewed The system of the present invention may include a database 94, 96, server and/or other storage means 116, whereby elements of the computer program product of the present invention may be stored. For example, information relating to the performance of a user may be stored to data storage 112. The data storage 112 may be incorporated on a local device 14 or may be remotely linked to the device 14 through a wired or wireless connection, such as the internet.

Figure 38B:
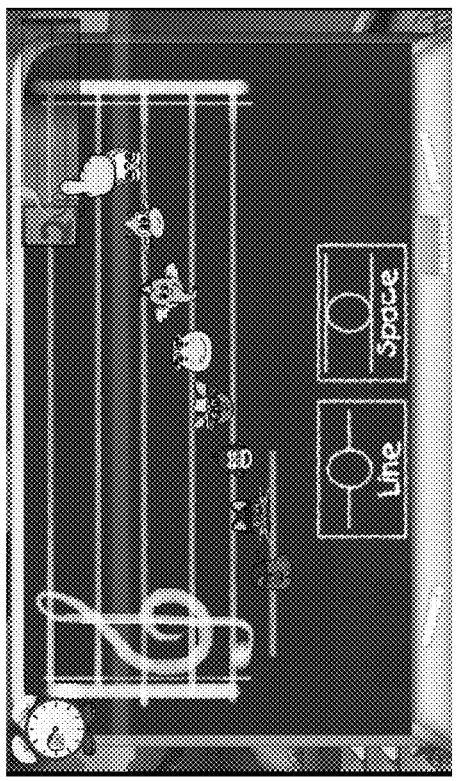
FIGS. 38a-d show 4 pictorial representations of exemplary game screens of the training.
Figure 39:
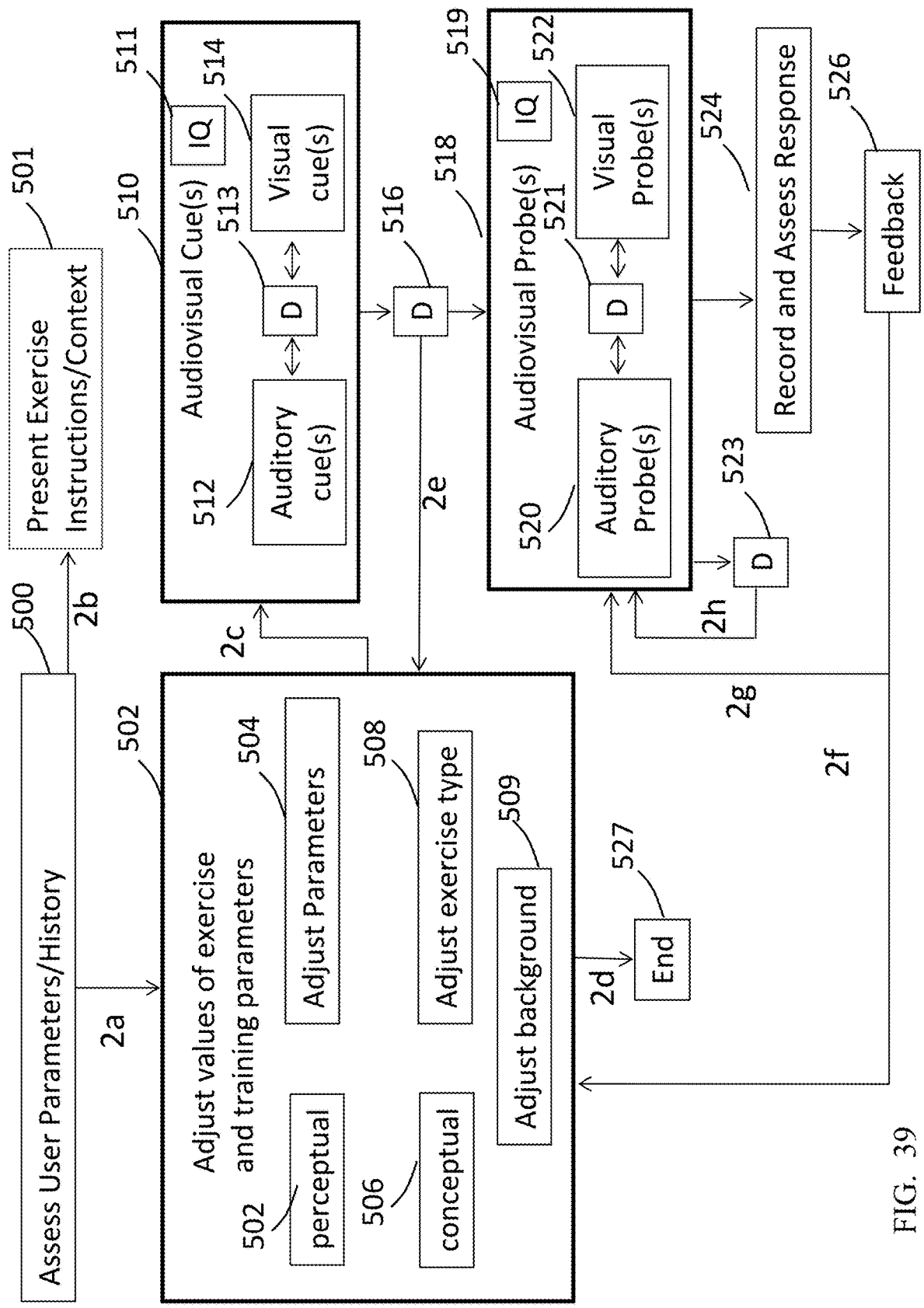
FIG. 39 is a flow chart showing an example embodiment of the training.
Figure 40:
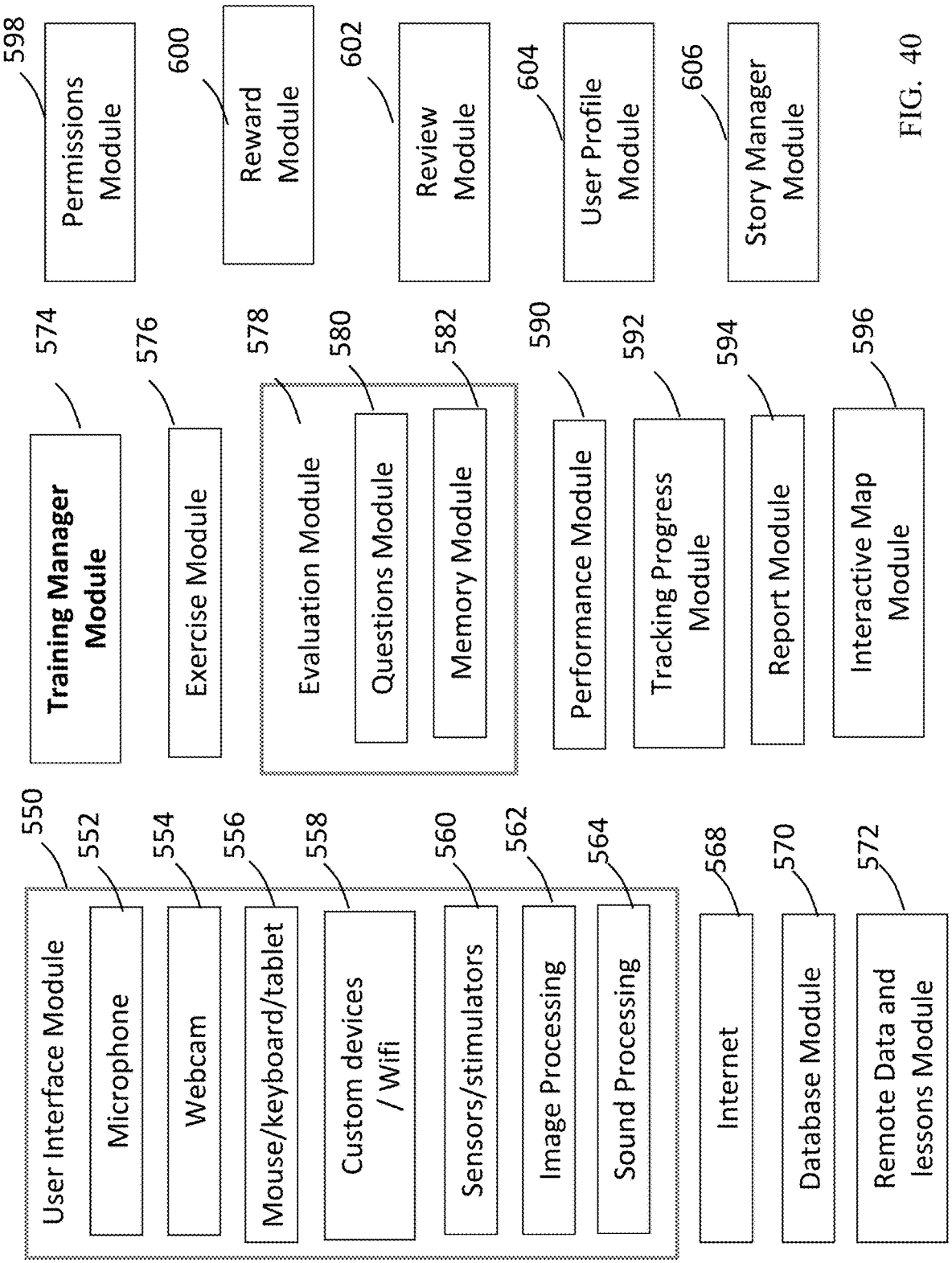
FIG. 40 is a representation of functional modules which may operate within the training program, in one embodiment of the present invention.

The overall cognitive training system as is depicted in FIGS. 1-42 includes a processor contained within a computer 14 where the processor is configured to present cognitive training to a user. At least one training program is contained within at least one of a set of computer modules associated with a series of training components as represented in FIG. 40 and detailed throughout the Specification. A visual display 456 (schematically represented in FIG. 41) is used in conjunction with an audio transducer 12 which are configured to be operated upon by the processor of the computer or computer device 14 to present visual and audio stimuli.

A user interface module 11, 13 allows the user to provide input to the processor of the computer 14 responsive to at least one of a specified ones of the training components. The training components are transmitted to the visual display 456 and audio transducer 12 from the processor of the computer 14.

The processor of the computer 14 is configured to (a) provide at least a first training component which is an audio-visual presentation of an animation which contains audio and visual stimuli in accordance with a theme that reinforces a cognitive pairing association of the visual and auditory stimuli and does not require a behavioral response from the user, and then present to the user, and, (b) provide at least one second training component selected from the group of: (i) at least one auditory cue through the audio transducer 12 and a visual cue through the visual display in order to realize a specific training exercise, (ii) provide at least one cross-modal cue, in a different modality than the auditory or visual cue previously presented with the cross-modal cue being selected as a function of the previously presented auditory and/or visual cue.

The processor is further configured to present to the user at least one of an auditory and a visual probe stimulus. The processor obtains user input responsive to a task presented to the user related to at least one of the auditory and visual probe stimuli as part of the second training component. Additionally the processor evaluates and stores the user input and then may adjust subsequent training of the user based upon the user input.

The processor of the computer 14 may be further configured present to the user at least a first visual cue and at least a first audio cue as part of the second training component, with the first visual cue and the first audio cue is associated with the audio and visual stimuli presented in the first training component. The first visual cue may be presented in the form of some predetermined contour with the auditory cue being a characteristic of the predetermined contour. As an example the predetermined contour of the first visual cue may be the depiction of an animal and the auditory cue may be a function of some characteristic of the animal.

The first visual cue and/or first audio cue may be selected from a set respective differing visual cues and audio cues presented to the user as a portion of the second training component.

The auditory and visual cues being presented to the user may be presented simultaneously, or at differing times where the auditory cue is presented to the user at a predetermined time interval either preceding or subsequent to the visual cue.

In general the audio and visual probe stimuli constitutes one of an audio and visual probe presentation which would require the pairing of a previously presented audio cue with a previously presented visual cue. The user may then input a pairing response to the user interface module with respect to a pairing between the auditory and visual cues previously presented.

Figure 2:
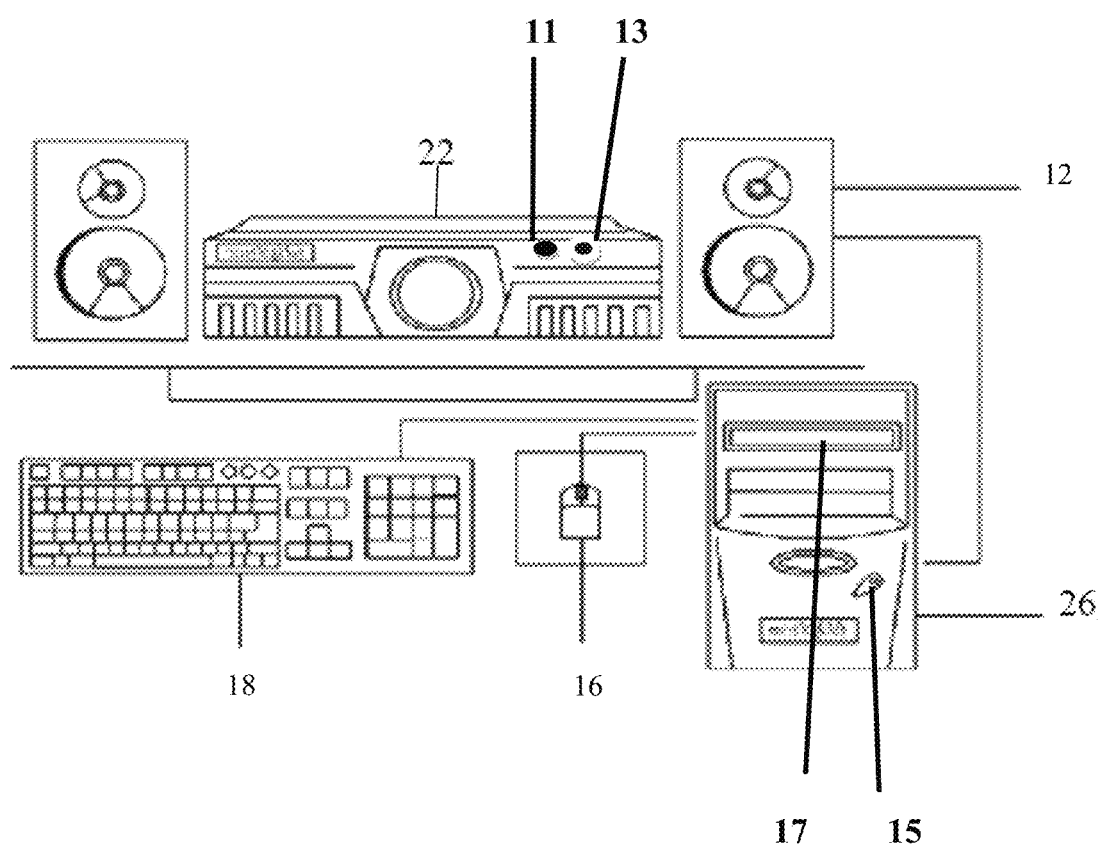
FIG. 2 is a general diagram of a computer system schematically represented and used to implement the training for a group format.

An alternative embodiment is shown in FIG. 2, wherein the system is be set-up in a manner that is more appropriate for use in a classroom. A device 26 similar to the device 14 can be used, but in addition to or instead of the display 10, there can be a video projector 22. Other accessories such as a touchpad display, a computer tablet that communicates with the device 26 and allows a teacher to control and modify the training. Wired or wireless training accessories can also communicate with the device 26.

Overview of Training.

The present invention provides systems and methods for allowing cognitive skills development realized using a unique cognitive-exercise based training platform which emphasizes but is not limited to music-based exercises, concepts, skills, associations, and paradigms.

In addition to training with musical exercises, cartoons, and stories, other types of non-musical exercises may be used either to supplement the music-based training exercises or in their own right, as described herein. The present invention may employ exercises which create associations for, or require processing related to, color, shape, sounds, and visual tokens. Exercises may also promote or require processing related to spatial rotation and spatial relationships, reading, repeating, and singing. The exercises are designed to promote changes in brain processing involved in verbal intelligence, attention, reading and language skills.

The invention may be operated by users of varying levels of musical skills or training, including none. The invention may be presented using characteristics that correspond to the prior musical training (if any) of a user, and may be adjusted according to cognitive capacity, age, IQ, ability, and attention span of a user. Performance of a user may dictate the parameter values used or adjusted in the training and the rate and path of progression of the user through available difficulty levels, task categories, and training schedules.

In a preferred embodiment of the present invention, the systems and methods may be realized using animated stories and video game exercises. Although many visual stimuli may be used, a preferred embodiment of the invention uses animated animal characters as the visual cues and probes of the training. The animals may have names, particular ways of dressing, walking, and unique voices which assist young users in remembering their individual identities. Accordingly, these animals are often deployed in various vignettes.

In some embodiments of the invention, musical exercises may be used which train users on skills that may facilitate playing a musical instrument, reading musical notation, or the like, but this is considered a secondary benefit, with the main intended benefits being related to cognitive training. Accordingly, for example, the exercises may utilize background distracting music which may decrease the ability of training to efficiently teach a musical skill since the intention is to train the student to increase cognitive skills related to "focus" rather than to increasing musical skills related to the musical exercise within which the user is engaged or to playing an instrument. This consideration does not dictate that the training exercises, and associated principles, could not be adapted to increase the emphasis on teaching a user to play a musical instrument.

Overview of Training Structure.

Figure 3:
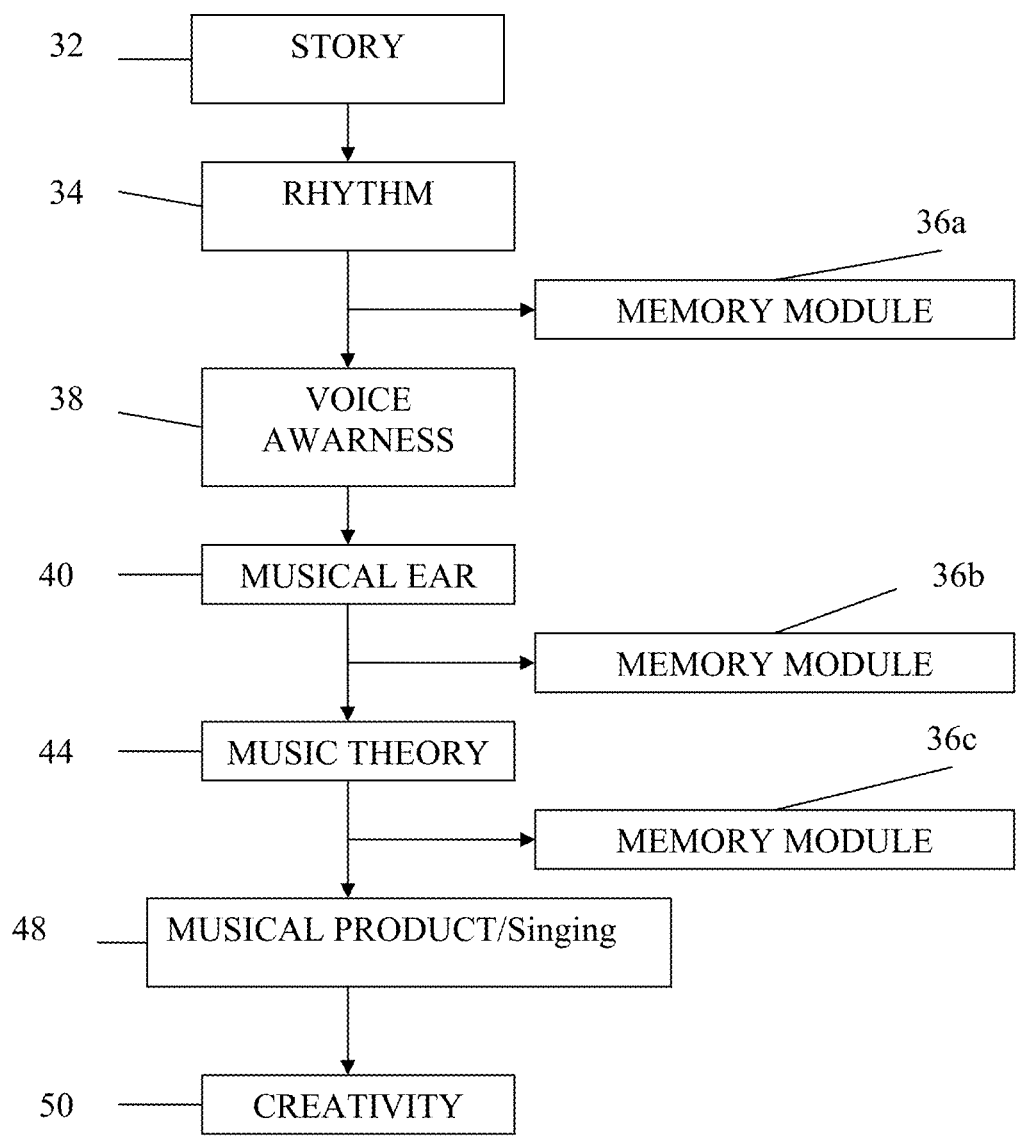
FIG. 3 is a flow chart of training session showing the exercise categories and memory modules being presented in a particular order.

The present invention may involve various compilations of training components including sessions, lessons, modules, exercises, and trials/tasks. A Session includes 1 or more presentations of at least 1 lesson (usually 2 to 3 presentations, where 3 repetitions is known as a "lesson triplet"). Lessons include at least 1 exercise from at least 1 exercise category, but usually between 2 and 6 categories, with a preference for 6, and can also include modules related to the exercises of the lesson. Modules may occur before or after a training exercise and provide the user with information related to the training or evaluate the user's knowledge, understanding, and skills and can include, for example, memory modules, question modules, story modules, demo and instruction modules which instruct or illustrate, to a user, what to do during a task. Exercises contain at least 1 trial with at least one stimulus, and can be passive or active. A trial can include several tasks, or 1 task which is repeated. Passive exercises do not require a user response or at least the response is not evaluated (i.e. a singing dog may ask the user as part of a song "can you say Doggie", but the exercise will continue whether the user says this or not). Active exercises require a user response. As shown in FIG. 3, a lesson may be organized to begin with a story module 32. Lessons may occur in a fixed format. Alternatively, exercises may be repeated within a lesson, and the selection, order, or difficulty lesson components may adjusted based upon user performance or preference of a user or administrator, and this can be controlled by the training manager module 574.

A story module 32 may be designed enables the user to understand the objectives of subsequently presented exercises and/or modules of the present invention. Different animal characters that the user may encounter during the training at each exercise or difficulty level may be introduced to the user via a story module. Accordingly, if appropriate, a story module may be invoked during a lesson, for example, if the user's performance meets a criterion for which the story module is defined.

As shown in the embodiment of FIG. 3, after the story module 32 there are 6 exercise categories that will now be briefly reviewed.

The training may present a rhythm exercise category 34 which may teach rhythm skills to a user. Alternatively a rhythm exercise 34 may simply be designed to be entertaining to the user and provide a break from more cognitively difficult exercises of the training. The rhythm exercise 34 may involve the user learning the basic principles of music rhythm, for example, such as rhythm perception, discrimination and production. Rather than just addressing the user's hand movements (e.g. clapping), the exercises may involve significant amounts of motor movement with whole body coordination.

After each exercise the evaluation module manager 578 may select and present an evaluation module containing a number of questions related to the training and evaluate the answers provided either to select subsequent questions, assess user performance, or for other reasons. One example of an evaluation module is a memory module 36a that may pose a small set (e.g. 3) of questions that are configured to test a user's memory about a previously completed exercise.

Several exercises categories are disclosed herein. Although different components of the exercises are reviewed for the particular embodiments illustrated, components and features disclosed for one type of exercise or exercise category may be applied to the other types of exercises and exercise categories. Many of the user responses in the training are made in response to questions. For example, "Which animal character lives the highest point on a musical staff?", "Which animal makes the following sound", "Which sound is made by the turtle?". The instructions may set up different contexts for the same stimuli. For example, if two series of notes are played, each having different notes and rhythms, the user may be instructed to attend to only one aspect of the stimulus, and ignore other aspects such as "which melody has the faster beat?" or "which melody has the notes played louder?" Accordingly, changing the question posed to a user may serve to allow the same stimuli to be used for different tasks, which in this example is a rhythm task or a musical ear task.

The lesson may include a voice awareness exercise category 38. The voice awareness exercise may be designed to warm-up the user's voice and train the speech skills of the participants. In a voice awareness exercise 38, a user may produce different sounds and learn about vocal range, voice volume, scooping voice (i.e. singing below an intended pitch) and vocal ornamentations. This may include using simple movements and voice mime. In addition to any skills that are trained in this category of exercise, voice awareness exercises may also have a high entertainment value, but may involve a lower level of motor skill requirements that the rhythm exercises. Consequently these may be easier then rhythm training for some young users who are still developing motor skills, and helps to avoid task frustration. Although questions may be asked by a memory module 36 related to the content of the vocal exercises, this is not shown in this example, in order to demonstrate that the memory module 36, or other type of evaluation will not always be evoked by the evaluation module manager 578. A lesson may omit an evaluation or memory module, or may only include this only after each repetition of the set of exercises, or after 3 repetitions.

The training may also present a musical ear exercise category 40 which may provide training related to hearing detection, discrimination, use of modality specific sensory memory and other auditory skills and processes. In a musical ear exercise 40, user may learn to detect musical notes, for example, such as C4 to C5, and may further learn to discriminate the notes and to produce or mimic the notes. After the musical ear exercise 40, a memory module 36b may pose one or more questions related to the musical ear exercise to the user. The musical ear exercise 40 may tend to require a higher level of user attention than other exercises.

The training may also present a music theory exercise category 44 in which a user may learn basic principles and knowledge about music theory. This type of exercise are designed to train skills shared with reading, such as promoting the relationship between a note on a musical staff and the corresponding musical sounds which is akin to the phoneme (sound) of a letter and the grapheme of the same letter. The music theory exercises 44 may introduce difficult and abstract concepts. Accordingly, music theory exercises may be considered to be the most cognitively difficult exercise category of the training, and somewhat removed from sensory processing, compared to other exercise categories. Accordingly, the music theory exercises 44 may require the user to sustain attention for a longer duration than required by other exercise categories, and may demand the highest level of attention. A memory module 36c may pose questions about the music theory exercise 44.

It is important to note the difficulty and attention demands of the exercise categories, since different categories may require varying drain upon cognitive resources. In this context it is obvious that the order of presenting exercises of different categories may be a design consideration related to the curriculum structure and content. Although these two categories (musical ear and music theory) are shown adjacent to each other, in FIG. 5 and FIG. 10, in an embodiment of the invention these exercises would not be presented sequentially for learning disabled, attention deficit, elderly or other users who may not be able to sustain attention very long. Instead an easier exercise such as voice awareness, or musical product 84, would be presented between these two categories.

In a musical product 48 exercise category, a user may learn about melody, songs and how to sing properly. The musical product 48 exercises may encourage memorization of song lyrics. In one example, a user is asked to match the pitch of one or more musical notes. A microphone and sound processing module 552 may be used to record the user's vocalizations, process the sound data, and determine if the user is matching the pitch correctly. At least one performance score, such as percent time where the instantaneous and/or average pitch correctly matching the target pitch within certain limits, or amount of variation in relative to correct pitch matching, may be calculated by the sound processing module 552. The target pitch may be adaptive according age and gender of the user. The precision of the music production can be an important aspect of the exercises and may be reflected in a performance score. As will be discussed, the complexity and conceptual difficulty of the vocalizations or lyrics may increase with harder difficulty levels.

The creativity exercise category 50 may be the most entertaining for a user. In a creativity exercise, a user may be asked to use the concepts, skills, and knowledge learned in recent exercises including exercises of earlier difficulty levels. The creativity exercises may not relate to musical skills and may focus, instead upon skills such as mental rotation or contour matching. For example, in the recent training a user may have been exposed to a series of animals that make certain sounds. A creative exercise may entail a user completing a jigsaw puzzle that, when completed, is in the shape of one of the animals (See FIG. 36C). Another exercise may entail choosing colors and dragging these onto parts of the animal's cloths so that the costume worn by the animal matches the clothing normally worn by the animal. Another task could entail a silhouette of an animal on one side of the screen and two animals on the left hand side of the screen, and the goal is to click on the animal that will match the silhouette (See FIG. 36B).

The present invention may terminate a training session by presenting both a musical product exercise 48 and then a creativity exercise 50. These exercises categories may reside at the end of each training lesson because these are designed to be relatively more playful and enjoyable to the user. Since the musical product 48 and creativity 50 exercises may each be perceived by a user as rewarding, they can serve as an incentive for the user to get through the earlier exercises. The creativity and musical product exercises may correspond to a reward's duration, with longer durations of these activities corresponding to larger rewards. Rather than, or in addition to, being used as an exercise category these may be provided as a reward to a user for good performance on an exercise, and may be presented more often by the reward module 600, if the parameter in the Training Manager Module 574 indicates this is warranted as part of the defined curriculum, in order to incentivize a user.

For each lesson, parameters related to the exercise sequence, lesson structure, and execution parameters of the exercises that follow the story module 32 may be fixed or may be dynamically adjusted. The training manager module 574 may be operated by the present invention to provide exercises to a user during each particular lesson. As shown in FIG. 3, there may be six exercise categories which may occur at each particular lesson and each exercise of the lesson may be at the same or different level. Less or more exercise categories may also be used.

Although questions may be asked during the training exercise itself, a series of questions may be presented to the user after each exercise, under control of the questions module 580. These questions may be adjusted by the questions module 580 in relation to the difficulty of the exercise in order to accurately test the user's learning. The answers to these questions may be utilized, along with users responses obtained during the exercises themselves, in the assessment of a user's performance calculated by the performance module 590. Performance may be defined as a percentage of correct responses. Reaction time measures (measured by the user interface module 550) may further be evaluated in relation to a particular expected time. For example, reaction times may be evaluated in relation to references measures such as a population normative value for average reaction time or the user's prior reaction times. In a preferred embodiment, if either a performance criterion (e.g. 75% correct responses) is reached for all, or a subset, of the exercises in a lesson or a maximum number of repetitions occur (e.g., 3 repetitions of the lesson may be the maximum number of allowed repetitions), then the user may be automatically moved to the next lesson of the training, and/or a higher level of difficulty. Further, only particular exercise of a lesson may be advanced in difficulty. Alternatively, upon reaching a performance criterion or a maximum number of repetitions, user may be allowed to select, from a set of available options, a higher difficulty level at their own discretion.

The present invention can be realized as a computer implemented method for training cognitive ability of a user. The method is implemented by one or more computer processors and comprises: grouping at least two training exercises selected from at least two of the exercise categories already disclosed and show in FIG. 3. At least one of the training exercise categories contains training related to at least two levels of increasing difficulty. The training includes presenting, to the user, at least one exercise of the at least two exercise categories at a level of difficulty that is selected to be appropriate for the user.

In another aspect the present invention is a system of music-based cognitive training comprising at least one device, such as a laptop or tablet computer, and a computer program including computer implementable instructions (i.e., a software program), which when made available to the at least one device, are operable to define a music-based cognitive training platform that is designed to improve one or more cognitive functions of a user. The music based cognitive training platform defines a series of exercises consisting of music- and sound-based training exercises designed to improve cognitive function, and are defined as cognitive training lessons, wherein each of the lessons includes two or more training components. The training components may be associated with different levels of difficulty. The training platform includes, or is linked to, a performance monitoring module which monitors, assesses, and/or records the performance of the individual for each training component. The training platform is operable to present to the individual, once the individual has achieved a minimum performance threshold for a first exercise component, a subsequent (second) exercise component or N-number of exercise components which are defined in a curriculum and which may be associated with an increasing level of difficulty relative to the preceding exercise component. The selection of the subsequent exercise component can be based on operation of the performance monitoring utility in order to adjust the difficulty level or exercise type according to the performance of the user. As such, the training platform is operable to enable adaptive training of the individual to iteratively improve the performance of the individual according to a training program defined in a training manager module.

A user may rely upon various input means to respond to the questions of the training, as managed by a user interface module 550. The response may be an oral (recorded by a microphone 552 and processed by sound processing module 564 having voice and pitch recognition), written (recorded by a tablet 556), typed (recorded by a keyboard 18), motion (recorded by a webcam 13) which is processed by imaging processing module 562, or any other response. Customized devices may record user behavior, such as hand movements recorded by a "smart" glove, or recorded by a sensor, and may use wireless communication to send data to the interactive module 558 operated by the training device 10. The performance module 590 may calculate the number of correct responses to the questions presented to the user and may further produce a result that is a ratio of user's correct responses to the total number of possible correct responses. User's performance can be assessed by the performance module 590 and reported by the reporting module 594. The user responses and performance may also be assessed in other ways such as by a teacher, parent, or other human based evaluation.

Unique Training Characteristics.

The training disclosed herein is unique from other cognitive training techniques in many manners. Although these are clarified throughout this material some consideration to this topic is given here.

In one embodiment of the training all the exercises of a lesson are presented in conjunction with background melodies or sounds which serve as a backdrop for the exercises. The idea is to force the user to more greatly involve engage the frontal network in the processing of the task and reinforce the ability to focus. The task may engage both the fronto-temporal and parieto-temporal networks.

In one embodiment, the background can contain a visual, a countdown timer or sound-based timer. The time allowed can be visually presented to a user with a clock, a clock that counts down in time, or a timer that makes ticking sounds. The time limit may be set in a fixed manner, or can be adjusted either as a function of difficulty level, user profile, user performance, or in another manner. The user may be required to complete an aspect of an exercise or lesson within a specified time limit. Failure to training component within an allotted time limit may cause the training to progress, so that a user does not spend too much time on a task. Users may get a higher score for finishing a task in less amount of time.

Some of the exercises of the current training may train a particular cognitive skill or musical concept by approaching the training from different angles. For example, a particular rhythm may be sung, clapped, matched, repeated, repeated with delay, identified, discriminated between several possible candidates, etc. While these different exercises vary in cognitive, sensory, and motor resources, for each task, the underlying skills (in this case, those related to beat analysis and processing) are commonly trained. Similarly, training a user about rhythm from auditory and visual modalities may reinforce common aspects of this skill from different modalities. Since some students may be better at processing either visual or auditory information, using different modalities in the training may benefit these individuals.

A main objective of the invention is to provide training, usually through a series of exercises, which is challenging without becoming too difficult or frustrating for the user. One manner of accomplishing this goal is by restricting feedback 526 provided by the performance module 590 to neutral or positive feedback and avoiding negative feedback. Another solution is to operate the training manager module 574 to limit the number of presentations of a particular exercise task within a given interval to avoid habituation or fatigue. For example, in some instances, an exercise task may be repeated three times, but not more than that, even if the user does not respond correctly at a required level (such as at least 75% correct answers). In order to avoid providing negative feedback, the training may not always operate the performance module 590 to evaluate a user's responses, or at least skip the provision of feedback 526 upon such evaluation.

Guiding Training Progression.

In one embodiment of the present invention, the training curriculum, including the sessions, lessons, exercises, modules, and other training components, may be adjusted by the training manager module 574. In order to make this type of adjustment, the training manager module 574 may use information obtained from the tracking progress module 592 (which calculates a user's progress), the performance module 590 (which provides information related to user performance), and relevant parameter values provided, for example, by the user profile module 604. In this manner the training may be adjusted based upon user current and historical performance, as well as their profile, which can include relevant parameter values related to, for example, age and grade level.

Figure 4:
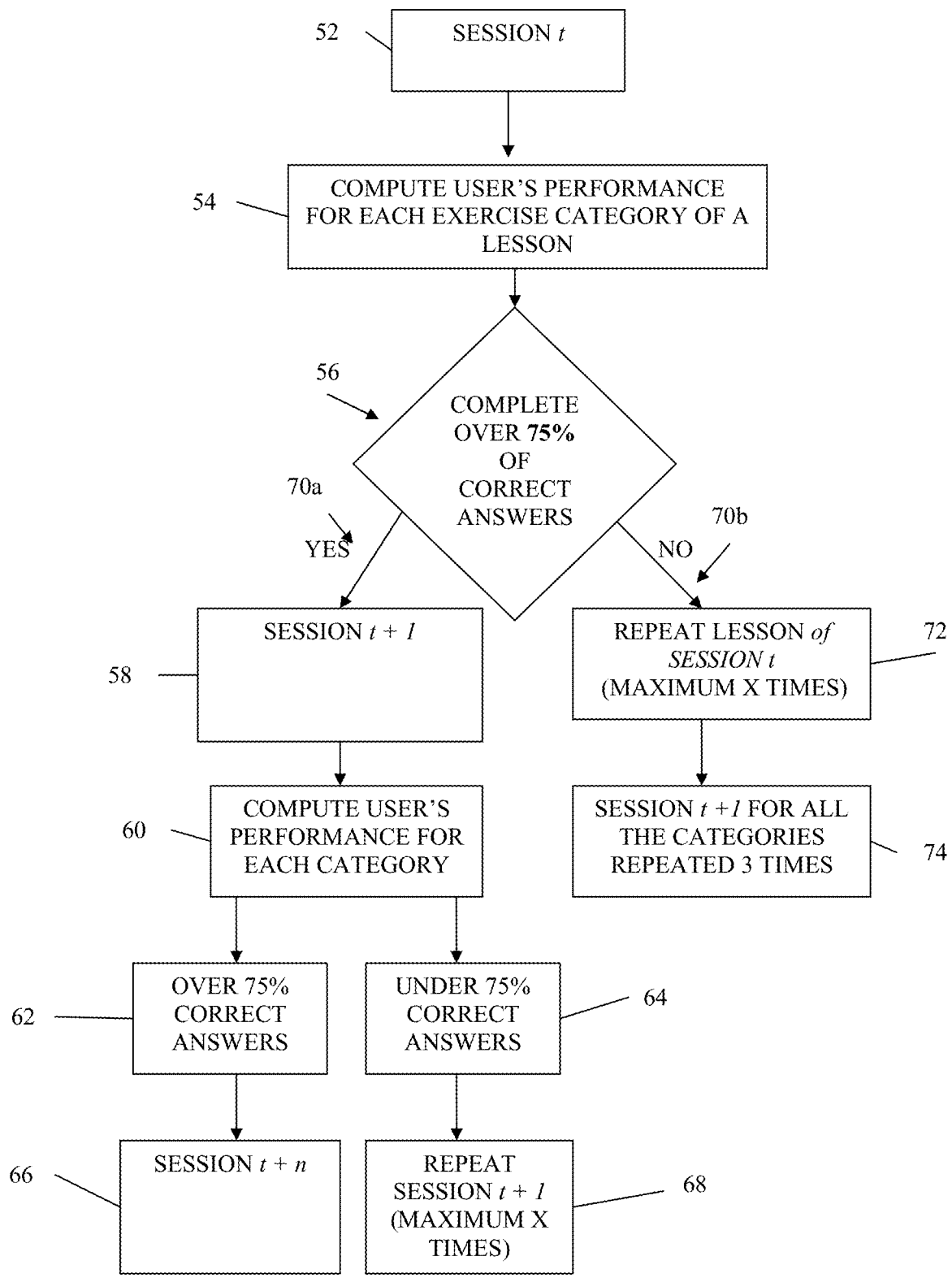
FIG. 4 is a flow chart showing the how the curriculum of the present invention is adjusted according to the evaluation of user performance.

As shown in FIG. 4, the parameters that guide the provision of a curriculum by the training manager module 574 may be based both upon user performance and the number of trials that have already been presented to a user. For example, after t-number of lessons 52 the tracking progress module 592 may analyze the user's performance which has been calculated by the performance module 590. In one embodiment, a minimum number of lessons in the session may be set to 2 and the maximum is set to 3. In other words, a requirement may be imposed that at least 2 lessons of a session must have been provided before the user is advanced to the next session. As an example, the user's performance may include information relating to a user's success rate for at least one exercise category, but normally is assessed across all categories of the lesson 54. The success rate may be indicated at least in part by the correct answers to questions posed to the user but may also include reaction time performance criteria.

If the analyzed performance 56 is assessed as reaching a performance criterion 70a (e.g., >75% correct responses), then the user may be considered to have obtain a "passing grade" on the training exercises, and the tracking progress module 592 may launch the next session 58 (i.e. t+1). Session t+1 may be comprised of a) the next lesson in the curriculum, b) session t, with any exercise category for which the user met the performance criterion being increased in difficulty, or c) session t, with any exercise category for which the user met the performance criterion being drawn from what would normally be session t+1. Alternatively, if the performance criterion is not met, then the session is repeated 72 up to maximum of X repetitions, where X is normally set to a maximum of 3 times to avoid frustration of the user. If a user has reached or exceeded the performance target criterion, as calculated by the performance module 590, then the progress tracker module 592 may make a determination that the user may be presented with session t+1, which can include lessons, exercises, or modules from later in the curriculum and which may be more difficult than what the user has just completed. Rather than changing the lesson in the current session, the lessons parameters may be adjusted so that the exercises are more difficult (e.g., more choices are presented to a user in order to increase difficulty of the task). If the performance is judged to be less than the performance target criterion then the training may consider the user to have "failed", and performance failure operations may occur, such as repeating the lesson "t" of the session.

After the t+1 session 58, the tracking progress module 592 may assess the user's performance 60, computed by the performance module 590, for each exercise category in the t+1 session. At this point, two cases may be possible, over or equal to 75% of correct answer 62 or fewer than 75% of correct answer 64.

If a user's performance is assessed with a minimum of the 75% performance criterion 62, the tracking progress module may launch the session t+n 66. In this step, 'n' may be increased by more than 1. In other words, if the user obtains over 75% (e.g., 100% for a majority of the exercises) then the user may be presented with a session, which is higher than the immediate next session of a curriculum (e.g. t+3 rather than simply t+2). Alternatively, when the user's performance is below the performance criterion (e.g., 75%) 64, the tracking progress module 592 may again launch same session 68 (in this case t+1). In this manner a user may repeat the same lessons, exercises, and modules of a session multiple times until a user's performance success art reaches a specified performance criterion.

The information collected and assessed as a user undertakes the training, may be the score calculated from correct responses and/or answers to questions posed to a user during or after the exercises by the evaluation module. In addition to performance criteria being applied by the performance module 590 to the users responses to the exercise tasks, performance criteria can be applied to the user's response data provided by the evaluation modules which may be included in the session. The reaction times of a user, either in response to individual or selected portions of an exercise, or the overall time required to complete an exercise, may also be assessed. Further, only incorrect responses and distributions of incorrect responses across various exercises may be assessed. User response information may be collected for each level of each exercise and for each category of exercise. The user responses and reaction time information may also be collected for each lesson and/or module or other grouping of exercises. For example, a lesson may include several exercises that are at the same level, and the lesson performance or individual exercise performance can be assessed. Time may also be assessed for time spent undertaking non-exercise activities, such as watching the story modules. The since a session may contain exercises of different levels, the levels of each exercise, may also be collected and assessed as part of the performance assessment.

In one embodiment of the present invention, the performance criterion may not change. For example, the performance rate can be set to 75% percent. In some embodiments of the present invention authorized control may be permitted that allows modification of the tracker progress module 592, so that the performance criteria may be adjusted. The training may also adjust the performance threshold from 'PT', to 'PT1'. For example, the training may start with a PT of 65% and move towards a PT1 of 85% as the curriculum progresses. The training criterion may increase or decrease with the overall performance of a user so that users who do not do as well at the training must meet a lower performance criterion (in order to keep them from being frustrated) and users who are better do not become bored.

Lesson Structure.

Figure 5:
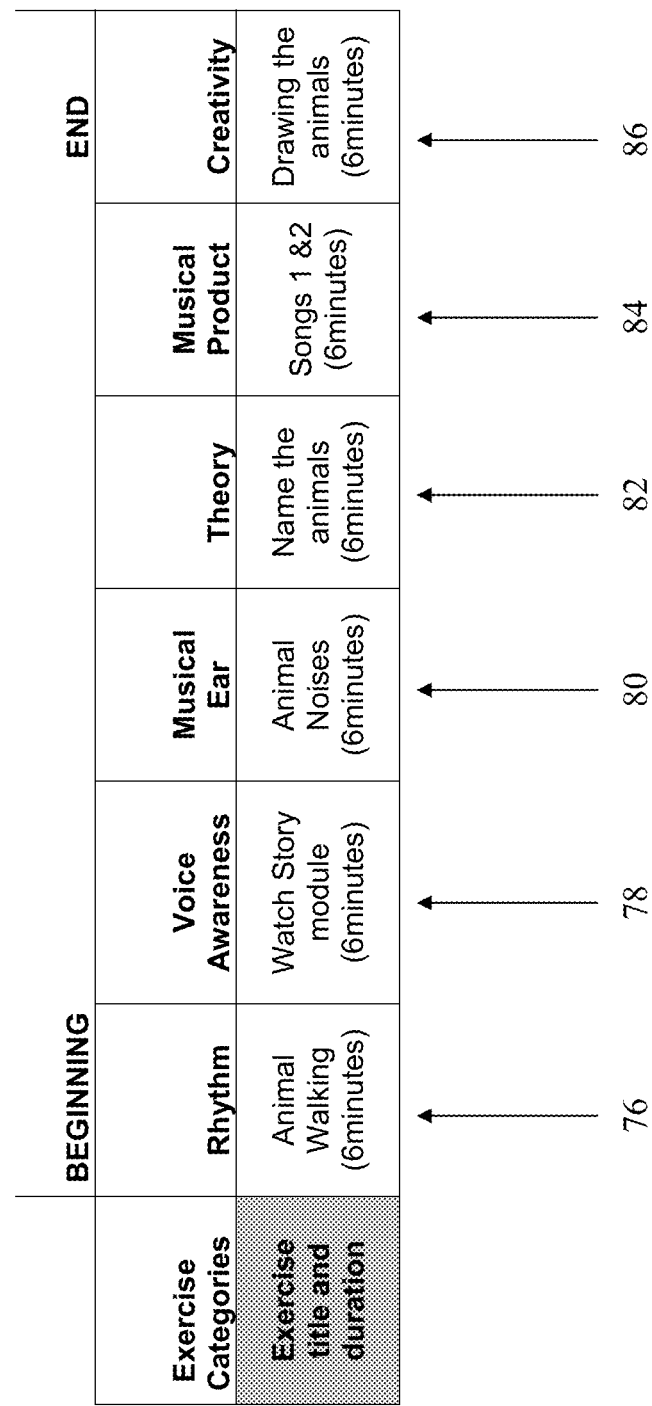
FIG. 5 is a table representing an example of a training lesson of the training program of the present invention which contains different exercise categories and illustrative durations.

A variety of types of training exercises may be included in lessons that are provided in each training session. For example, as shown in FIG. 5, there may be six categories of exercises in the present invention: Rhythm 76, Voice awareness 78, Musical ear 80, Theory 82, Musical product 84 and Creativity 86. In a typical embodiment, in the training there will be at least 3 exercise categories in each session, and at least one lesson will be preceded by a story module and followed by an evaluation module. The sequence and duration of lesson components may be fixed, or may be adjusted. For example, each exercise may last a similar span of time, such as between 5 to 10 minutes. As shown in FIG. 5, the duration of each type of exercise may be a consistent period of time that is 6 minutes. The duration of lesson components may also vary in accordance with various parameters related to user performance. Training time may also be varied according to user or administrator preferences, when allowed, such as the choice by a user to repeat training instructions or other training aspect. The duration of the exercise can include the time for both the instructions and the exercise activities to be presented to a user. A lesson with 6 exercises categories will typically last between 25 and 30 minutes. The exercise categories may be presented to a user in the order in which they are shown in FIG. 5, or in some other order.

Local, Remote, and Distributed Embodiments.

Figure 6:
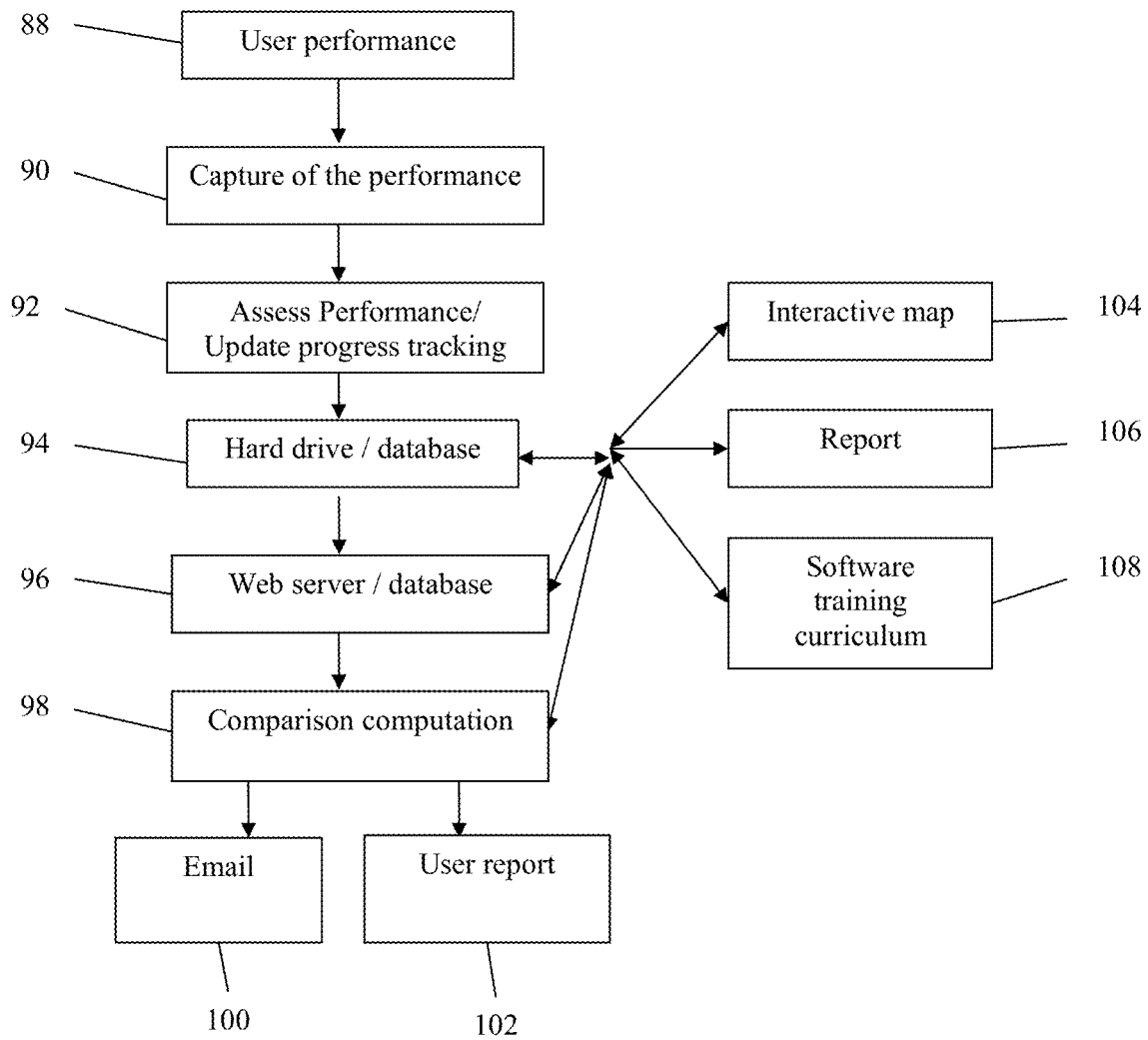
FIG. 6 is a flow chart showing tracking of user progress and the transfer, use and storage of training data.

FIG. 6 shows an example of tracking of user progress and the transfer, use and storage of training data. User performance information is derived from a user's interaction with the training 88. The performance data is captured and processed 90 by the user interface module 550. Performance is assessed 92 such as calculating a performance score. In step 92 an evaluation module may also be launched. The questions presented by the questions module 580 can be adjusted upon the user's performance, such as providing harder questions to user who has scored better performance. Performance for the exercises and the evaluation module can be assessed by the performance monitoring module 590 and the results provided to the tracking progress module 592. The users responses to the training, summary statistics and performance results are then stored to a data storage means, for example, such as a database 94 of the local device 14, or a database 96 stored on a server. The data related to responses collected during the training and performance results can be used in a variety of manners. For example, in one embodiment of the present invention the data may be utilized in four different ways.

A first manner is sending the data stored in the local data storage 94 to a web server database 96. The web server 96 may evaluate the data, for example, perform a comparison 98 between user data and reference data contained in the database (e.g., population nonnative data kept in the database 96). The results of this evaluation 98 is used to generate training results which may be sent through an email 100 to the user, a parent, a teacher, a school administrator, or other intended target. Alternatively, the results of this evaluation may be sent back to a device 14 that is operating the present invention, or which is monitoring the progress of at least one student that is using the current invention, in the form of a user progress report 102. The user report may be presented to a user by the training as feedback, or can be sent to an administrator as a set of statistics for a particular user. The report 102 may provide the user with an indication of the user's performance as compared to that of an appropriate reference group. Preferably, a sample of the population to which a particular user is compared will have similar characteristics with the user, such as age, gender, IQ, grade level, musical skill level, socioeconomic level, primary language, and/or other characteristics, in order to generate an appropriate comparison.

Figure 31:
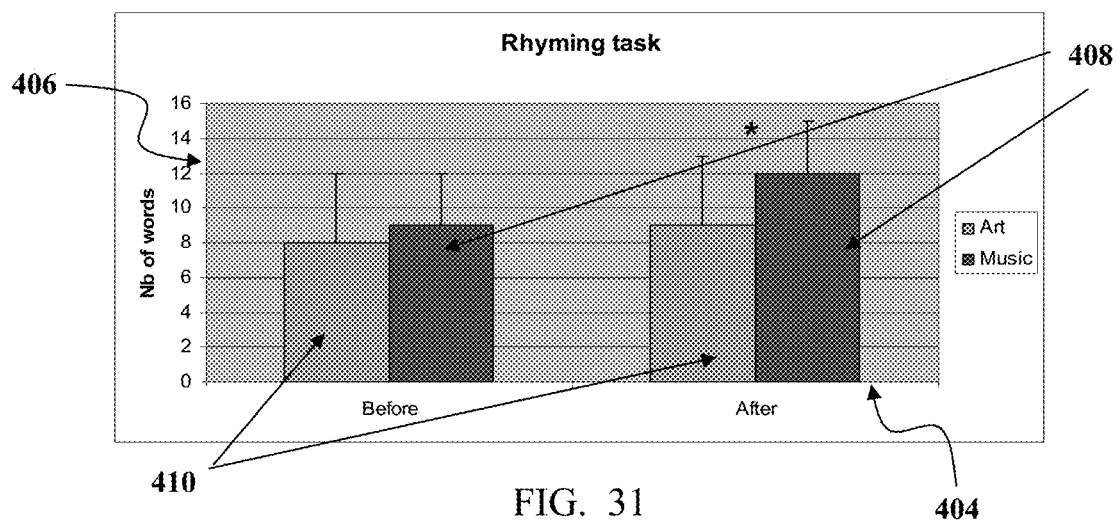
FIG. 31 is a graphical representation of the study results of the present invention showing the rhyming score of the method of the present invention and the control groups before and after training.

A second manner that the data may be utilized, is that the stored data can be provided to an interactive map module 596 so that the information on the interactive map 104 may be updated to reflect the user's progress through the training. FIG. 31 shows an interactive map 104 that indicating the user's performance and/or current level.

A third manner that the data may be utilized, is to produce a progress/performance report 106, similar to report 102 except that it is provided to the training software for storage or other use. The session report may be provided to the user in a variety of means as feedback. The report 106 can also contain summary statistics of the user's training performance including summaries of correct and incorrect responses, and reaction times, both globally and as a function of exercise category. Rates of change of performance and other statistics and raw data related to user responses can be statistically assessed, compared to self or population reference data. The training can combine data from multiple reports to track a user's response over time.

A fourth manner that the data may be utilized, is that the data are provided to the progress tracker module 592 so that the training manager module 574 may adapt the training curriculum 108 that is provided to a user. In this manner training curriculum can be adjusted according to a user's skills, performance, or needs. The needs of the user may be indicated by data corresponding to the user (including data managed in the user profile module 604), and the analysis or other review of this data may provide support for the selection and ordering of the training components presented to the user.

Training Platforms

Figure 7:
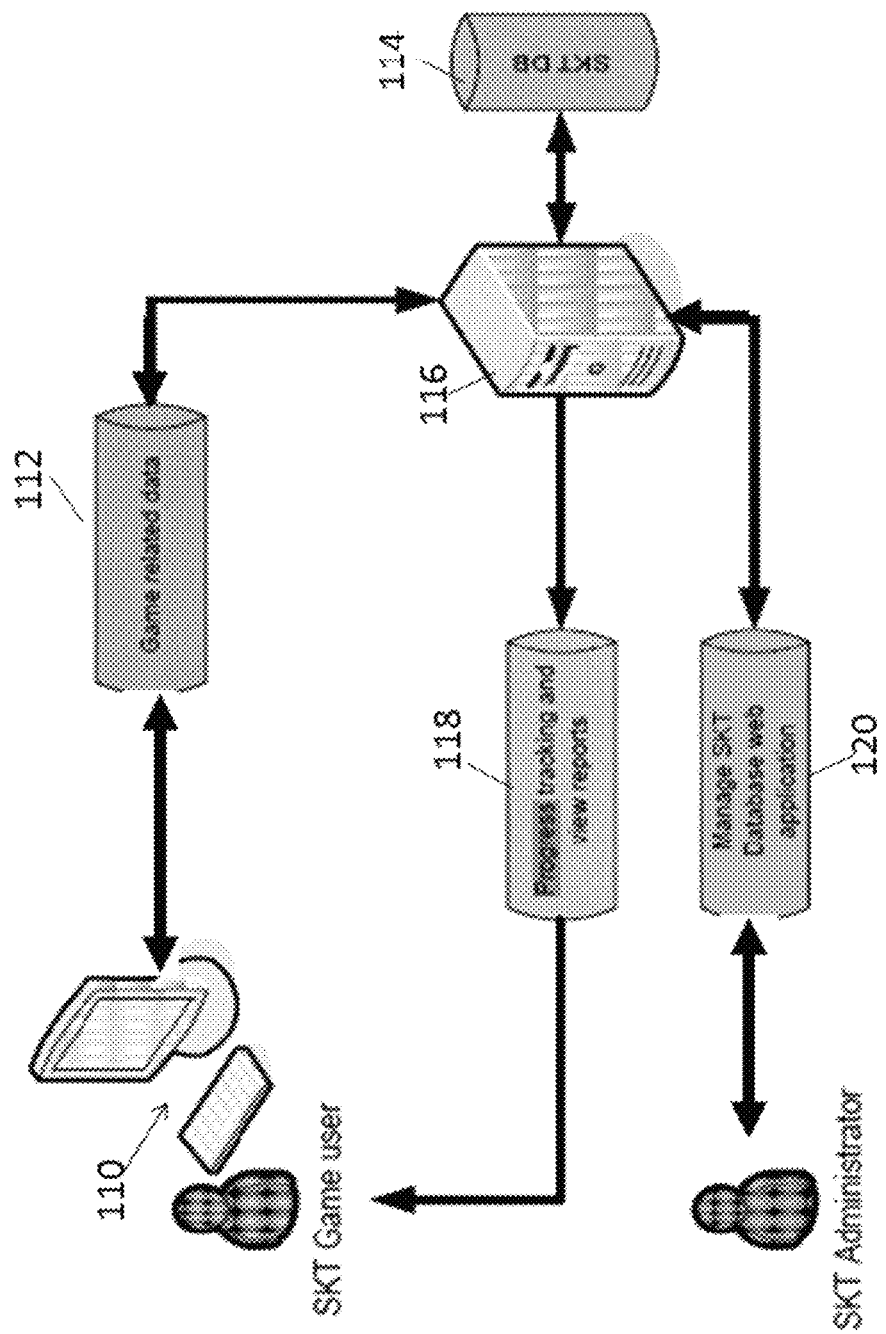
FIG. 7 is a diagram showing an example deployment of the training which incorporates a web server computer which interacts with a user's local device, an administrator, and a user, over a wired or wireless connection.

The training may be realized upon a large variety of training platforms. An example, with remote implementation is shown in FIG. 7. In the figure, the invention is implemented as a Smarterkids Training (SKT) game that provides training to the user through a computer program operated by a server 116 (i.e., server based training which can be realized over the internet) and provided to a user on a local device 110. The device 110 may operate according to a computer program product that may offer the training in a variety of formats. For example, the training may be implemented, partially or fully, as a computer game, a type of interactive story, or any other training format. The format may be adjusted to be suitable for presented on a particular platform. For example, an interactive story can be provided on an interactive e-reader device, a game format of the training can be presented by a gaining console, smart television/cable, television platform such as Netflix or Amazon, smart-phone, tablet or other suitable device.

In one embodiment, the platform includes a device 110 which can be any device which is capable of running the training modules shown in FIG. 40 to provide the training to the user. The training modules comprise data, algorithms, and computer code which is necessary to provide the training. The training modules 550 to 606 may be realizable using both software and hardware. The training modules contain algorithms to present training content to a user. Accordingly the evaluation module 578 is configured to present evaluation module content and operations (such as occurs in step 272) of the training component to a user. In addition to the description of the modules that will be disclosed within this specification, several additional aspects of the figure should be introduced here. Firstly, all the training modules may operate upon and share information with other modules. Secondly, the modules are meant to assist with defining the invention and are thematically based according to the features they provide during the training. All the modules may simply have been realized within training software program and a dedicated device which are configured to realize the features of the training. The internet module 568 can assists with allowing the device 110 to access the internet and communicate with remote components of the training system such as a remote server. When implemented on a server, the internet module 568 can assists with allowing the remote device 110 to access the training over the internet and communicate with remote components of the training system such as supplying training to a user on a web page or communicating with a training application installed on a user's local machine 110. The remote data and lessons module 572 can assist with synchronizing data between the server and a local device, and working with the internet module 568 to provide training to one or more remote users and allowing remote users in the same or different locations to use the training together. For example, the remote data and lessons module 572 can assist with users logging into the training and with being paired together to jointly participate in the training. The exercise module 576 can be operated upon by the training manager module 574 to provide the exercise content related to the different tasks.

Figure 41:
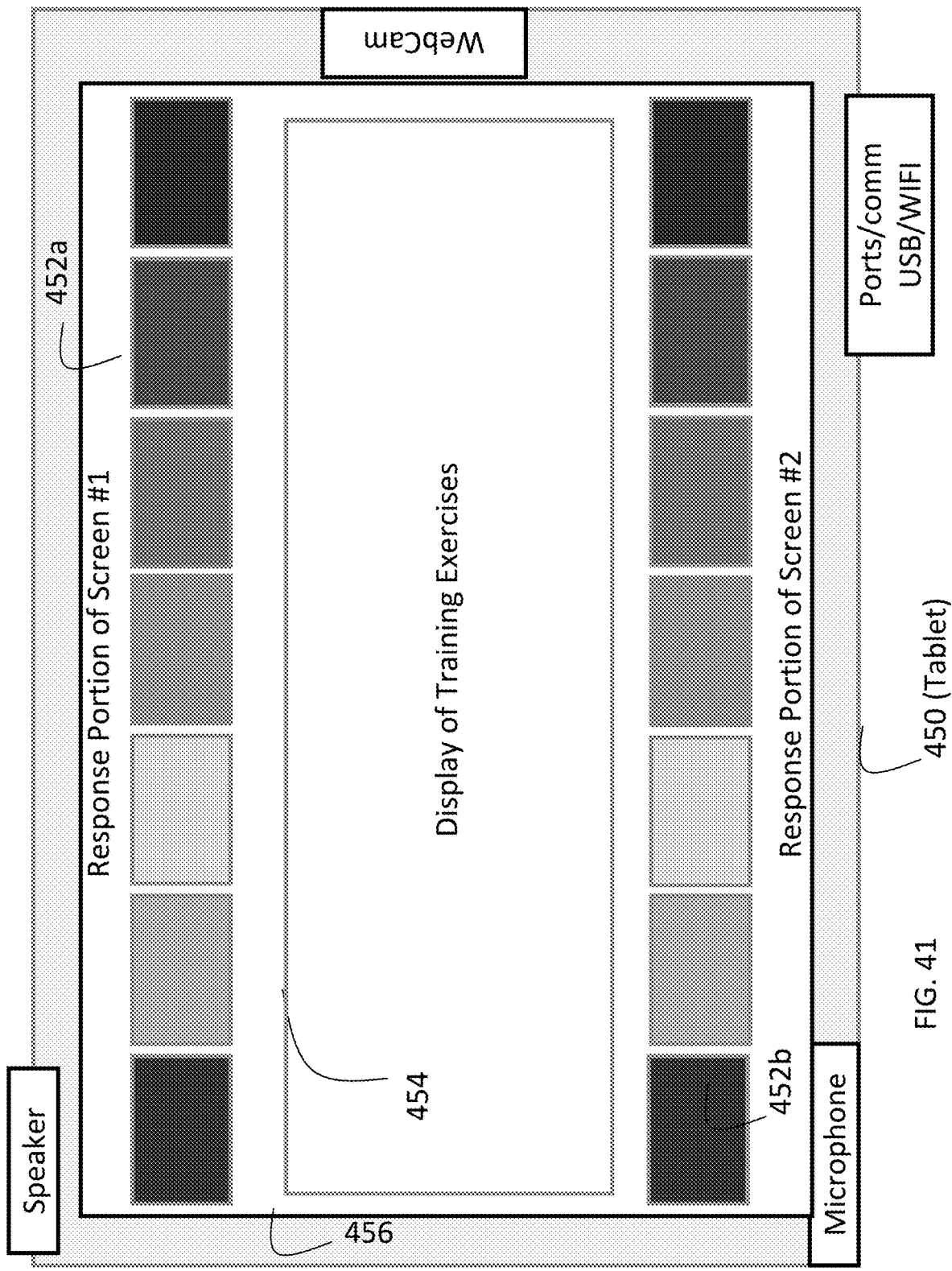
FIG. 41 is a graphical representation of a two player embodiment of the training program realized using a tablet computer with a touch screen and in which players interact with the training using a graphical user interface.

The device 110, can be a PC tablet 450, as shown in the embodiment of FIG. 41, that may obtain information and training software from a remote server over its internet link. The device 110, has components such as a processor, memory, power, and other computer components which can implement the training according to training instructions, as are well known. The tablet is shown with additional common features of a tablet including a webcam, microphone, speaker, ports, and internet connectivity, and provide a first user response area 452a, and a second user response area 452b, whereby two users may respond to training exercises that are presented in the middle area 454 of the tablet display 456.

The training can be controlled by a remote computer/server 116 which may communicate with the device 110 over the internet, using wired or wireless technology. The device 110 can implement the training by running computer code that resides locally, or which it obtains from the remote server 116, or a combination of the two. If the device 110 runs the software locally then it may intermittently send game related user data 112 to the server 116. Such user data may be stored by any device utilized by the present invention, or data storage can be remote from, but accessible by, the present invention such as a database 114 on the remote server 116. User results customized for the user can be sent to the user 118 and results customized for an administrator can be sent to the administrator using a communication channel and web-based application 120. The administrator may also manage the training and access relevant information used the web based application 120.

As shown in FIG. 7, feedback may be provided to an SKT administrator who is a clinical or institutional administrator in charge of the training. Feedback or reports may be provided through a variety of means, for example, such as through a web application 120 to a web server 116 or remote database 114, to any email addresses, to a printer, or to another data storage means in which the user's data may be saved. The present invention may translate the user's data into performance, evaluation and progress reports. As shown in FIG. 7, such reports may be categorized and/or named according to their content, for example, "Progress Tracking" reports. The database 114 can stored information remotely or can upload information to a user's device 110. The database 114 can store all information related to a user and to a user's training such as a user's profile, performance, age, parameters related to the exercises, lessons, modules, training, and levels.

It would be known, to those skilled in the art, that the remote server 116, can host the training itself, or it may work in conjunction with other remote servers. For example, if a telecommunications, internet or other type of company which provides service/content (e.g., Netflix™ or Verizon™) supplied the training to users on their computers or televisions, then the server 116 may act as a portal or relay that permits access to a $3^{rd}$ party server which would itself provide the training.

Report Generation.

Figure 8:
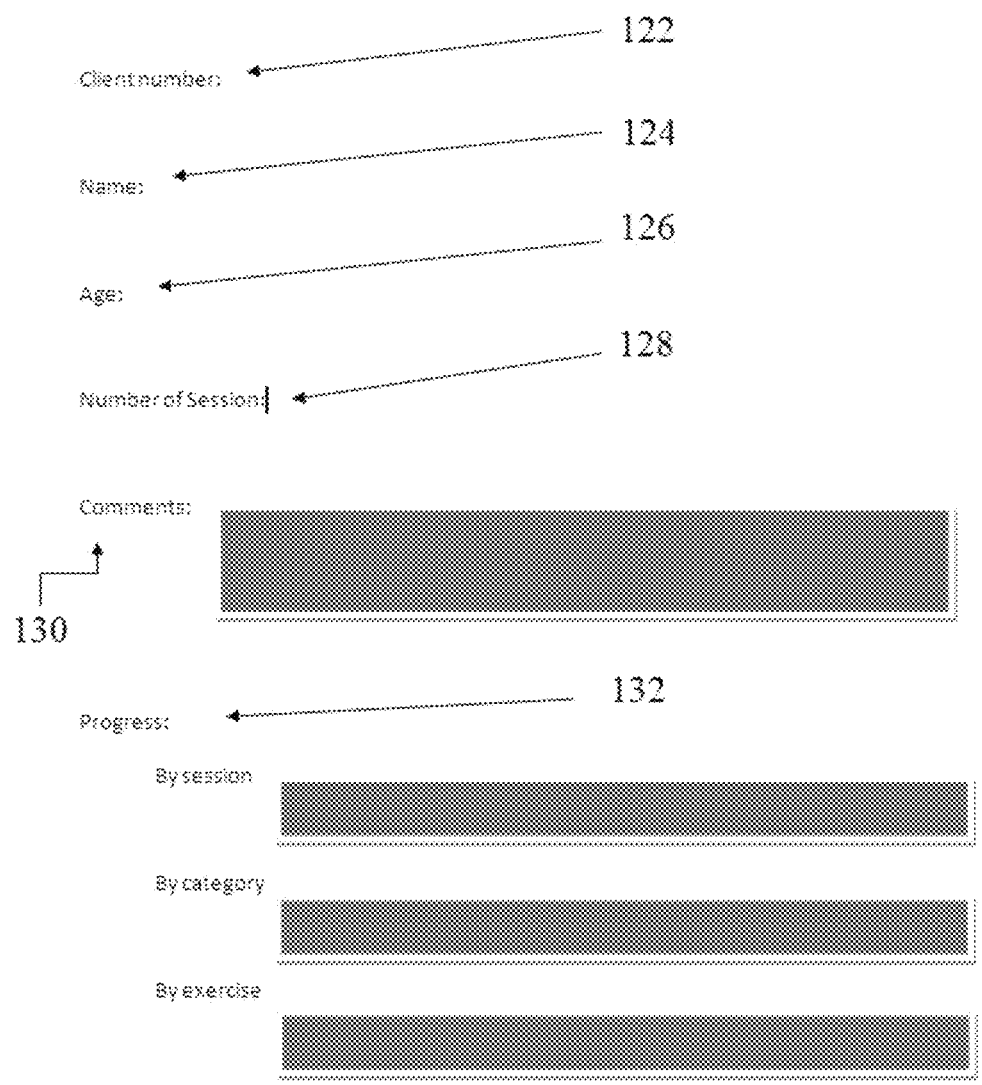
FIG. 8 is an example of the format and information fields of a first page of a report generated by the tracking progress module report.

An illustrative example of a report generated by the report generation module 594 is shown in FIG. 8. The report may contain user information, for example, such as client identification code 122, name 124, age 126. The report may also provide a section for comments 130 which may be completed by the user, clinicians, therapists, parents, or other parties. The report may also display progress update information 132 for each session, lesson, exercise category, module and level, of the training. A variety of other types relevant information and report formats, graphs, percentiles, and summary statistics may be provided, as is well known.

Figure 9:
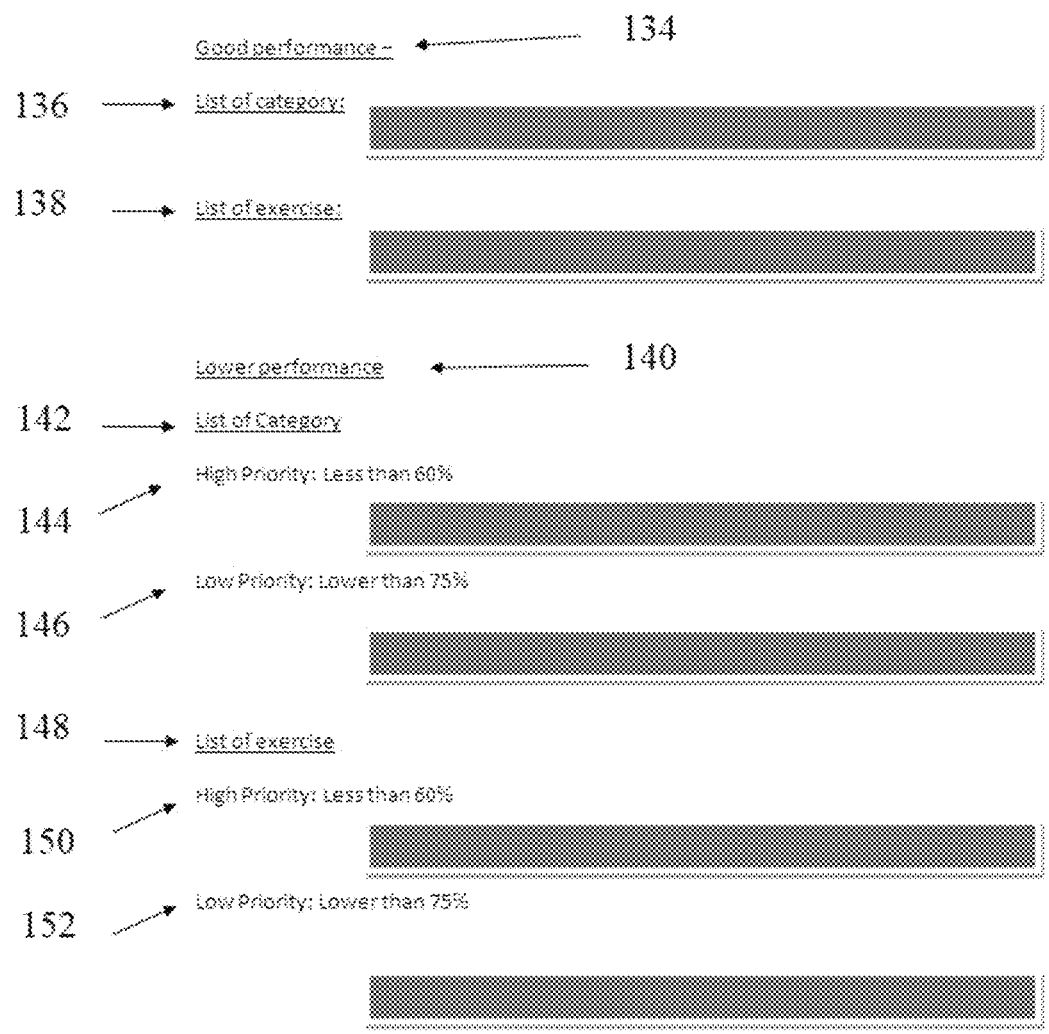
FIG. 9 is an example of the format and information fields of a second page of a report generated by the tracking progress module report.

Further information which may be included in the report is shown in FIG. 9. This includes data relating to the range of performance of the user classified as either "Good performance" 134 or "Lower performance" 140. Good performance 134 may be reported in two components: user performance reported by exercise category 136; and user performance reported as a function of specific exercise 138. "Lower performance" results 140 indicate which categories 142 and exercises 148 need to be improved.

The exercise category performance list 142 for lower performance 140 can be divided into a "high priority" section 144 which are exercise categories in which the user obtained less than an X % performance rate (e.g., 60%); and a "low priority" section 146 which include any exercise category for which the user obtained less than an Y % performance rate (e.g., 75%). The exercise performance list 148, shows the same information broken down for individual exercises rather than categories. Rather than using 60% and 75%, the values may be defined otherwise, defined by teacher, defined according to population nonnative data, defined according to the training context or user profile, as well as other manners.

Training Structure (Sessions, Lessons, Exercises and Modules).

As shown in FIG. 10, in a preferred embodiment of the present invention, the curriculum may be organized into 90 lessons. The table 154 may constitute a preferred curriculum for healthy children, without developmental delays (i.e. "special needs" users). The users may be aged 3-6, preferably aged 5-6, but any age range may be found to be acceptable. A training session may typically contain up to 3 repetitions of a single lesson, but a session can contain less than that if a user's performance is sufficient. Lessons 1 to 3 can occur on 3 sequential days, with each lesson being repeated up to 3 times on a particular day. Although lessons 1 to 3 may be identical, the story components of the lessons or the evaluation modules that follow the lessons may be different. Additionally, the parameters of lesson 3 may be adjusted so that it is slightly harder than lesson 1 or 2. If each session is trained on a separate days, then the full training may be accomplished in approximately one to three months, depending upon whether the user requires 3 repetitions of each lesson and whether the user's skill allows them to progress more rapidly.

The order of the training exercises within each lesson may be by category, and may include: rhythm 156; voice awareness 158; musical ear 160; theory 162; musical product 164; and creativity 166. The order of the exercises across each triplet of 3 lessons (e.g., lessons 1-3, or 7-9) may be the same or different. In lessons 1-3, the rhythm exercise that will be used is "Animal walking #1". In lessons 1-3, although the order of the training exercises may change, the exercises themselves will usually not change materially. In a preferred embodiment, the order of stimuli presented within a particular exercise, such as "Walk like the animals #1" may change, however the content will generally not change unless user performance is assessed and suggests increasing the difficulty of the training. In that case, in one embodiment, for session 1, lessons 1-3 may have increasing difficulty, where the parameters of the training are increased to make the exercises harder. In this example, there may be a total of 90 rather than 30 difficulty levels. In lessons 4-6 the difficulty of the exercises may be increased relative to session lessons 1-3, as reflected by the title "Walk like the animals #2". Alternatively, the exercises may simply be different and not necessarily harder. For lessons 1, 2, and 3 the "Walk like the Animals" exercises will normally all have the same background theme, which in this example is a setting of a pond and a raft, upon which the animals perform. Having a particular background for a set of exercises provides users with more context for remembering what to do during the training task.

The training may include multiple difficulty levels of training, as shown in FIG. 10. For example, a first, second and third lessons of a triplet of training may be of increasing difficulty. In one embodiment, the 30 difficulty levels are implemented across 30 lesson triplets (e.g. lessons 1-3, and other lesson triplets are shown in the table) where each lesson triplet represents one difficulty level and each subsequent triplet represents a harder difficulty level. Alternatively, if the $2^{nd}$ and $3^{rd}$ lesson makes the stimuli a little harder, either by increasing the number of stimuli presented or by adjusting some other parameter of the training then up to 90 difficulty levels would be realized. As training progresses, subsequent lesson triplets may not be more difficult, but may just be considered different, and there may be only a few levels of difficulty, such as 6. Between 2 and 100 levels of difficulty may be realized by different curriculums, with 100 levels requiring between 1 and 4 months for completion.

In one embodiment, the training may require that a particular level of performance is obtained across all the categories at a particular lesson before the user is allowed to go to the next lesson. However, lessons may typically be repeated either 3× or until performance for the exercise reaches a performance criterion. For example, in the session starting with lesson 1, Animal Noises #1 will be repeated by the training manager module 574 until either the user reaches the 75% correct performance with respect to correct responses, or until the lesson is repeated 3×. In either of these cases Animal Noises #1 will be replaced with Animal Noises #2.

Accordingly, in the case of a very good student, Animal Noises 1, 2, and 3 can be completed by the end of the first training session. In one embodiment, during a subsequent session, Animal Noises #3 will be repeated, since that is the most difficult difficulty level for that particular exercise theme (i.e., there is no Animal Noises 4). In another embodiment, Animal Noises #3 may be presented in the subsequent session during every other lesson in order to decrease redundancy. In a further embodiment Animal Noises #3 may be entirely skipped by training manager module 574 during lessons 4-9 since the user has already mastered the exercise. In a further embodiment, components of the exercise parameters in Animal Noises #3 may be further adjusted to increase difficulty by speeding up parts of the exercise.

The table 154 also shows an embodiment in which the review feature is first made available in the curriculum at a point 168 corresponding to lesson 30. The review feature 602 and evaluation modules that follow the exercises presented in a lesson, are intended to stimulate and "crystallize" the neural network created during the training exercises. This is a very important neuroeducation principle that we are using throughout the training. A network is created to process the exercise task and this network will be stimulated through the training and reinforced by the evaluation modules that follow the training exercises.

In addition to a curriculum having various default organization of sessions, lessons, exercises, and modules, the training can insert story modules and evaluation modules at various points of the training. In a preferred embodiment of the present invention each session is proceeded by at least 1 story module. In an alternative embodiment, the first presentation of a lesson is preceded by a story module. For example, lesson 1 of lessons 1-3 is preceded by a story module, but lessons 4-6 and 7-9 each simply begin with a Rhythm exercise since the user is already familiar with the material that is being taught in these subsequent lessons. In this case the latter 6 lessons are simply harder difficulty levels of the exercises. Alternatively each lesson triplet is preceded by a story module.

The curriculum may be chosen by the present invention to address the specific requirements of a particular user, as determined utilizing data such as performance data and the user profile data. Further the curriculum 610 may be set manually, such as by and administrator. The invention may provide for adaptively presenting certain exercises at adjusted levels of difficulty based upon a user's performance 300. Additionally, the training may consist of balanced training that includes exercises configured to provide specially selected categories of training during each part of the training, wherein each category is selected to train and draw upon different musical skills (see FIG. 10). These exercise categories were select to allow the rotation of the user through a series different cognitive skills exercises that are designed, both in terms of content and duration of the exercise, to capture and retain the attention of users.

Typically, the duration of each exercise may last between 5 to 10 minutes depending upon the user, but normally about 6 minutes. The exercise duration may be stable through the exercise categories and levels provided to a particular user, or the exercise duration may vary. A variety of exercise levels and durations may be provided to a particular user. Each lesson may include the same number of exercises in the same categories, or a different number.

Training Manager.

A training manager module 574 (and/or teacher, when implemented in a classroom setting) may guide a user through exercises. The combination of exercises provided to a user in a specific curriculum 610 may vary, and may be tailored to a specific user and user performance. The analysis of performance data and user profile data may provide information regarding the skill, level, or other characteristics of a user. This information may be utilized to determine the best presentation of exercises, including the levels, category, format (such as in video game style, or other styles or formats), duration, and order of exercises, to be presented to a user that will best support the learning and progression of skills of the user. Although users may advance through the exercises on a predetermined schedule and independently of performance, this will usually occur contingently on performance.

In another example of the method of the present invention, as shown in FIG. 35, a user may be presented with training having exercises that are a set of games. The user may choose to start a game 440 and indicate this choice to the present invention. A user information module 442 may be presented to the user, and the user may be required to enter user information that is used to create a user profile or look up an existing user profile by way of the database module 570. This information may be utilized by the user profile module 604 to determine if the user has previously utilized the present invention and if there is any information relating to the user's level of performance that may be used by the training manager module 574 to adjust the training sequence and difficulty level. The performance module 590 and tracking progress module 592 can be used to assess the user's responses to the training 444, including any modules presented after the exercise. These results can be stored by the database module 570. An interactive map module may be updated according to the user's recent performance and may be presented to the user 446 by the interactive map module 596.

Performance Monitoring.

The exercises may be adjusted for difficulty, but the default parameters of each exercise may be associated with different levels of difficulty. The training may include, or be linked to, a performance monitoring module 590 for monitoring and recording the performance of the individual in each exercise component at each difficulty level. The training manager 574 may be operable to present to the individual, once the individual has achieved a minimum performance threshold for a first exercise, a subsequent exercise, or N exercises, associated with an increasing level of difficulty relative to the preceding exercise, based on assessment of user performance by the performance monitoring module 590. As a result, the training may provide adaptive training of the individual to iteratively improve the performance across all exercise categories by adjusting difficulty level of the individual exercises or the entire lesson.

In the training, level 2 may generally be more difficult than level 1; level 3 may be more difficult than level 2, and so on. The difficulty may, for example, be adjusted upwards by using more complex rhythms or melodies, or by increasing the number of sounds to discriminate, or the number of elements to remember in an exercise. Performance target criteria may be set. For example, a criterion may be that approximately 65% to 85% of questions posed by a question module 580 must be answered correctly either for items related to a particular exercise, a module that follows the exercise, or across an entire lesson. The performance target criterion may be applied only to a selected set of the exercises or lessons within a session.

The performance monitoring module 590 may transfer information, including raw data and analysis results to the training manager 574 and to a database module 570, so that data about a user may be stored and then recalled when a user utilizes the present invention at a future date. In this manner, the appropriate training parameters for a user may be set each time a user begins training.

A clinician, or other professional, may further obtain historical user information to assess the user's performance and progress. For example, this data may be summarized and reported by the report module 594. If the clinician determines that the training parameters such as difficulty level should be adjusted, the clinician may act as a training administrator by setting parameters and curriculum related to the training 502. Accordingly, by operating in administrator mode, the clinician can cause the present invention to present to the user a customized training curriculum, with customized training protocols, parameters, or performance criteria.

Evaluation Modules.

Figure 11:
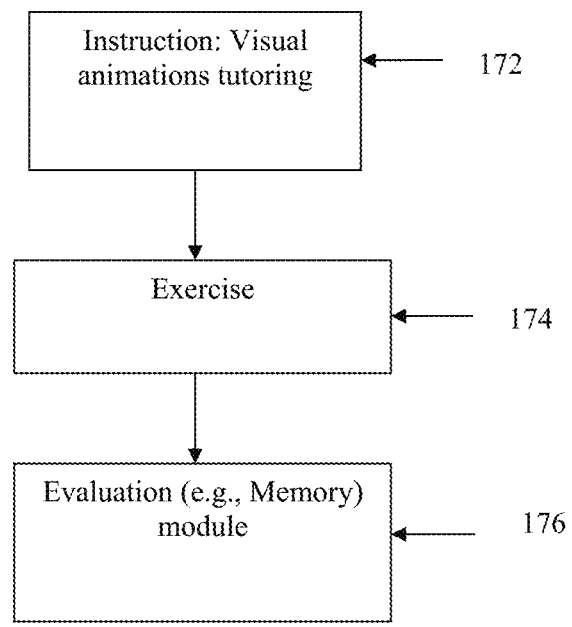
FIG. 11 is a flow chart showing an exercise implemented within a lesson including stages at which the computer program operates to provide instructions, the exercise tasks, and an evaluation module which in this case is a memory module.

The present invention may include evaluation module subroutines 578 to evaluate and reinforce the skills of a user. As shown in FIG. 11, evaluation modules 176 normally follow an exercise 174 or a lesson and are related to preceding content. However, evaluation modules 176 may also be defined, or contingently invoked, intermittently within an exercise, lesson or session. One type of evaluation module is a memory module 582 which evaluates and activates a user's memory. Within a lesson, the series of training components may include the step of presenting instructions 172 to the user, either by a story module having an animated cartoon and an animal character who instructs the user what the task will be, or by verbal instructions spoken to the user, or otherwise. The exercise 174 follows the instructions. Some type of review is then presented by an evaluation module 176 and user response data that are input from the user are assessed by the evaluation module 578. Evaluation operations 176 may involve presenting one or more questions to a user auditory, visual or auditory-visual modality, and evaluating a selection, choice, vocalization, movement, or other user response.

Figure 12:
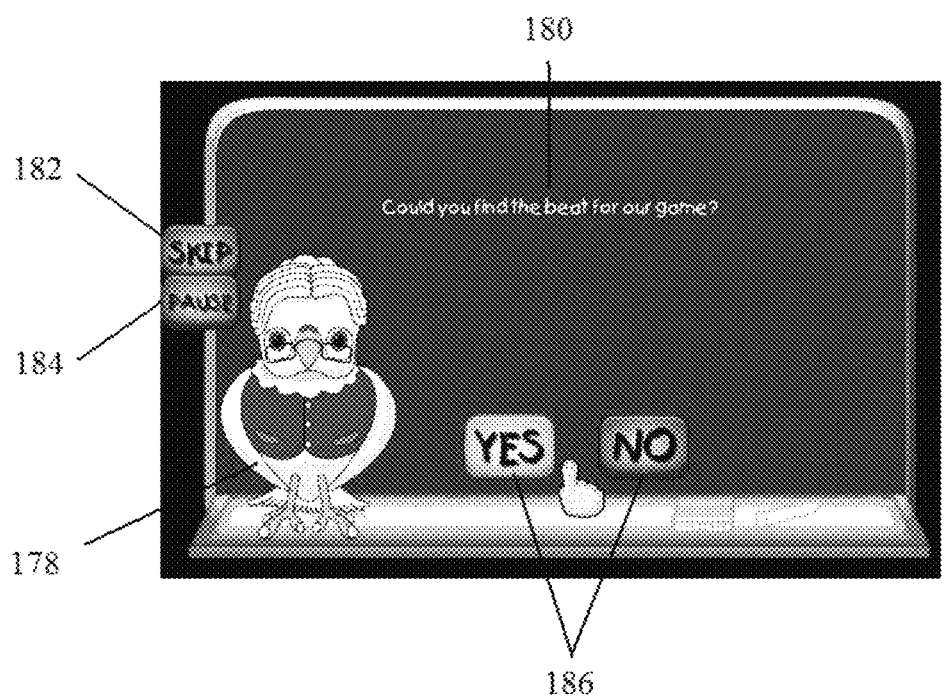
FIG. 12 is a pictorial representation of screen from an evaluation module of the training.

In another embodiment of the present invention, as shown in FIG. 12 an evaluation module is shown in which a user is asked to provide a subjective evaluation of whether the user was able to detect and reproduce the beat in the prior exercise. This example shows that evaluation questions may not always have an answer that is correct or incorrect. Although the screen shows the question in written form, the question will almost always be spoken to the user as well-reading should not be considered a prerequisite of the training. As shown in FIG. 12, the evaluation module may have several elements presented in a pictorial representation, including one or more animal characters 178. Virtual menu items may be utilized by a user to navigate through the training, to provide input to the present invention. Some menu items presented to a user may include a "SKIP" button 182, a "PAUSE" button 184, and one or more response buttons 186, for example, such as a "YES" response button and a "NO" response button. The response buttons may allow response to questions posed by the memory module, or to provide other user input. Virtual keyboards may also be provided by the user interface module 550. The user interface module 550 can be comprised of both software and hardware (such as a keyboard interface touchscreen of a tablet computer)

Figure 28:
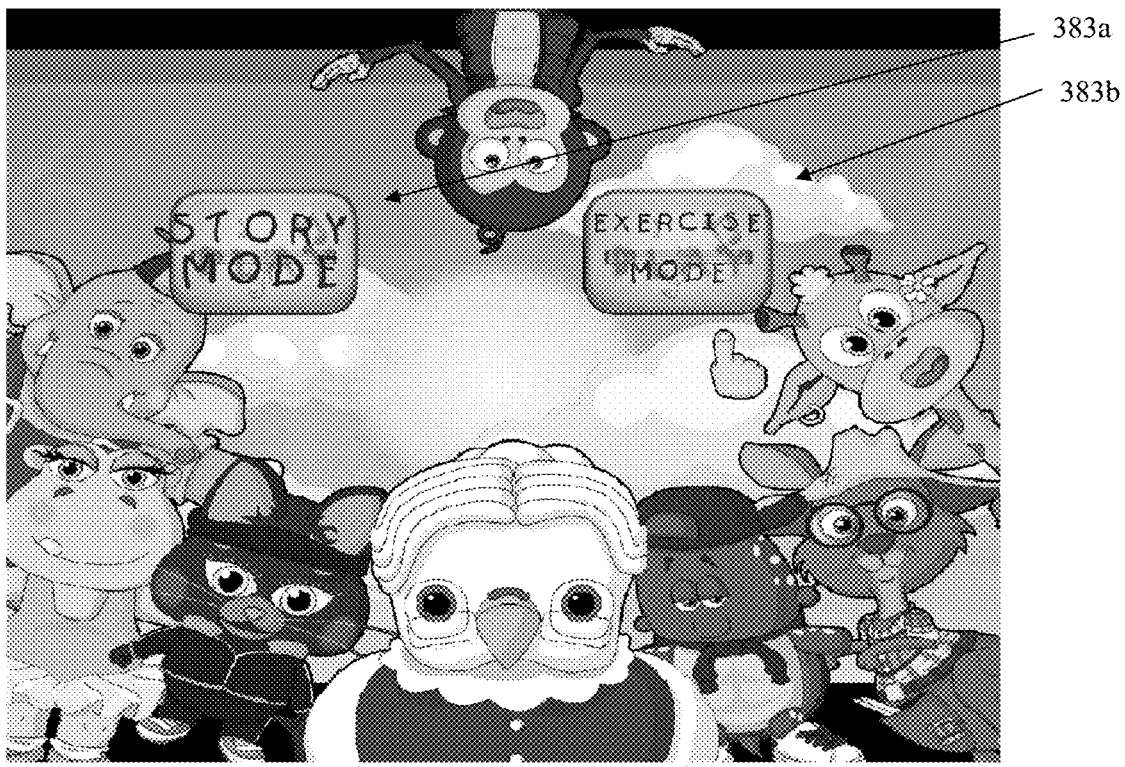
FIG. 28 is a pictorial representation of a game screen which allows the user to toggle between a story module and exercise module of the training program.

FIG. 28 shows a pictorial representation having buttons 383a,383b that allow a user to operate the training in "Story" or "Exercise" modes. Review modes, and other modes are also possible.

Figure 13:
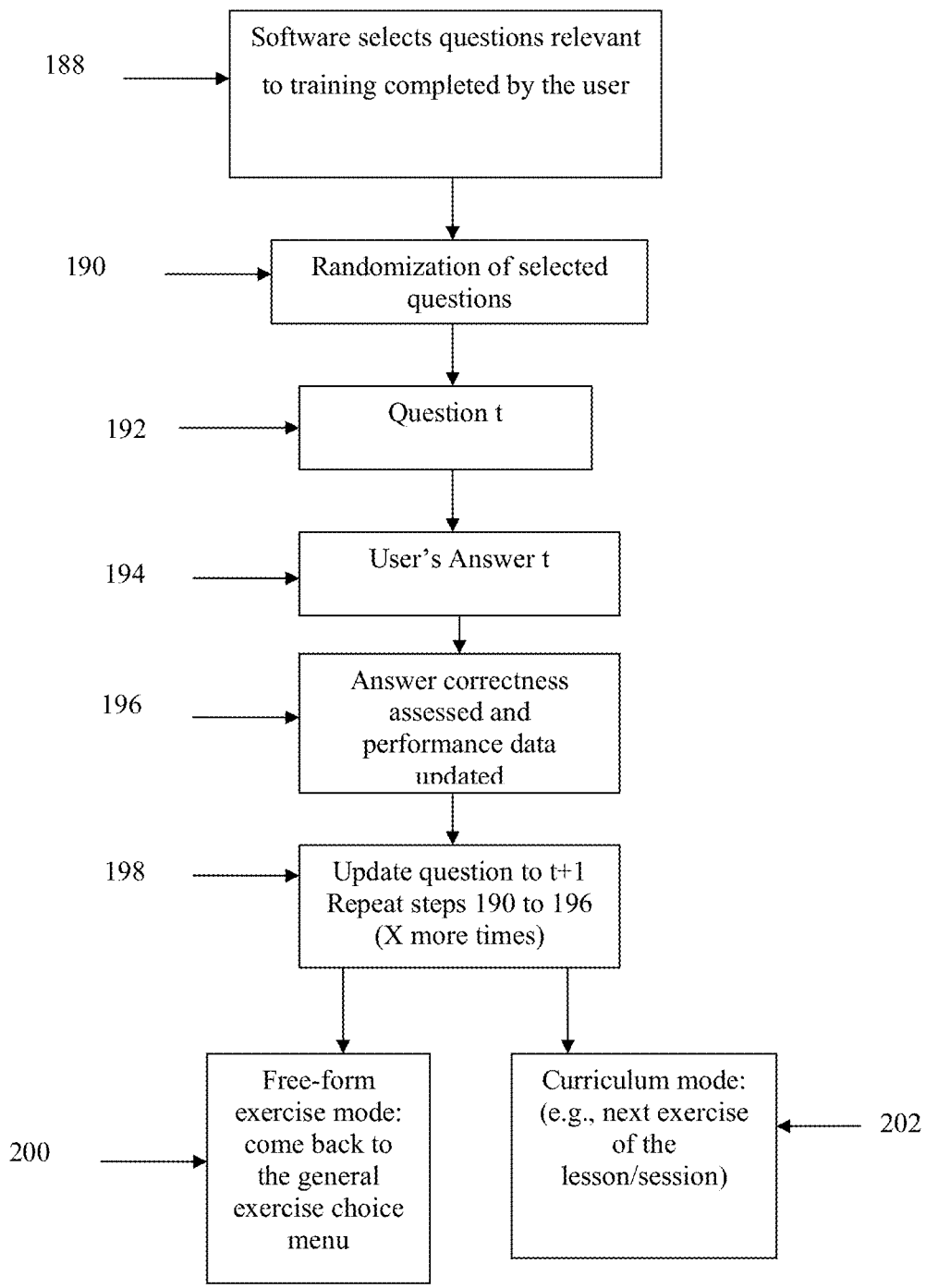
FIG. 13 is a flow chart showing the operation of an evaluation module (e.g. a memory module), assessment of user response, and tracking of user progress, which is followed by the selection of either the free form or curriculum mode.

FIG. 13 shows another embodiment of the present invention with component steps that are implemented by the evaluation module 578. Although a fixed set and order of questions may be used, the software may also be configured to implement the step of selecting one or more questions 188 from a set of questions. In the latter case, the evaluation module 578 may access the set of questions stored in a database 570, which may be a local or a remote data storage means 94, 96. In the next step, the order of the selected questions 190 is randomized. Each question may then be posed to the user. For example, a first questions may be posed to the user as a question 't' 192. The user may respond to the question 't' 194, and the response may be collected and or evaluated by the evaluation module 578 working in conjunction with the performance module 590, or any other analysis module of the training. The evaluation module 578 may operate to repeat the process of posing questions to the user multiple times, for example, such as two more times 198 for a total of three questions/answers. As illustrated, after an exercise lesson is completed the user may be allowed to make choices that will cause the next part of the training to be selected by the user if the software is operating in free-form mode 200, or the next exercise of the lesson or session will be triggered if the user is operating in curriculum mode 202.

The evaluation module 578 may further be operable to evaluate the knowledge or skill of a user. The evaluation module 578 may utilize the user responses and other information and/or data collected by the present invention, for example, such as the time that a user took to complete an exercise, to analyze, or otherwise evaluate the knowledge or skill of a user. The responses in particular may be evaluated to determine the number of correct responses provided by the user to the questions posed to the user. The memory evaluation module 578 may also, or alternatively, transfer response information to another analysis module of the present invention for that module to undertake an analysis of the performance rate of the user. The evaluation module 578 may further be operable to include elements that may help to remind the user about the selected elements of particular exercises, and to reinforce concepts taught in the exercises.

Figure 14:
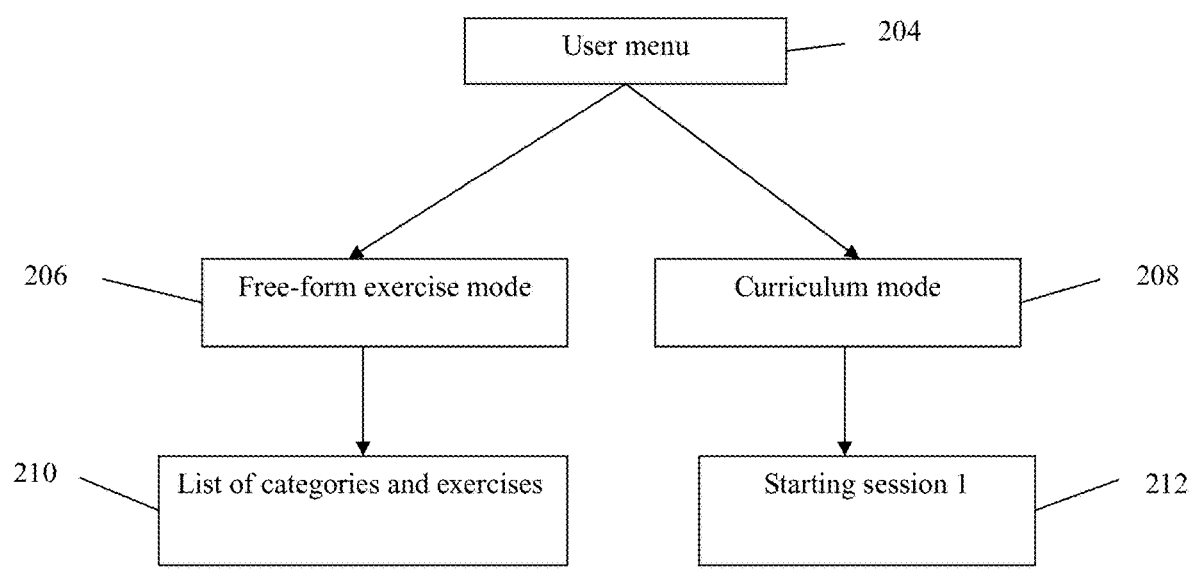
FIG. 14 is a flow chart showing the provision of two modes of the present invention including 1. Free-form exercise mode and 2. Curriculum mode.

As shown in FIG. 14, the two or more modes of operation may be presented to a user. The training manager module 574 may provide the user with a general exercise choice menu 200, for example, such as a free-form mode 206, which then provides the user with a list of categories and exercises that they may select 210. Alternatively, if the user selected the curriculum mode 208, then the user may be presented with the subsequent exercise 202 defined in the training curriculum of the present invention.

Training Modes and Permissions

The present invention may offer users a variety of modes of use. For example, as shown in FIG. 14, a user menu 204 may offer users at least two modes of use, for example, such as a free-form exercise mode 206, and a curriculum mode 208. The free-form exercise mode 206, may be operable to allow users to access and practice any of the exercises of the present invention. The exercises may be presented to the user in a list so that the user may utilize the input means to choose an exercise from the list 210. In a preferred embodiment the list will be presented graphically and will only include exercises already completed by the user, with the most recently completed exercises at the top of the list and the rest in chronological or other order. The curriculum mode may represent a set of exercises, lessons and/or story modules. Users may be guided through the program, for example, such as by a training manager module 574. A user may be provided with a starting session 212 based upon a user profile, when available. In the curriculum mode users may be limited as to what exercises they are allowed to choose. As training progresses, the curriculum mode may utilize data and other information collected by the present invention to adapt the exercises, lessons, and/or modules to the performance level of a user and more generally to the skills of the user. Accordingly, in Curriculum mode the training is provided to the user according to predefined curriculum, although the order and characteristics of the training may be adjusted based upon the user profile and performance.

The review option may also be embodied as one or more screens showing a set of icons that represent at least a subset of the different exercises of the training. Selecting an icon for a particular exercise will cause the training to again repeat the exercises.

In addition to Free Form, Curriculum, and Review mode, there may also be Story mode and skills assessment mode. In Story mode, 1 or more story modules are presented to a user and the user can also be allowed to choose a new story, repeat a story or skip to the next story. In story mode, the user may be limited to story modules which are related to exercises which the user has already completed. In one embodiment, the user may select stories by clicking on pictures of the interactive map which show prior lessons that have been completed by the user.

A skills assessment mode can be presented to a first-time user of the present invention in order to assess their capability for doing certain types of exercises. The skills assessment mode may contain a set of exercises that are designed to produce a skills assessment result that indicates what exercises, lessons or difficulty levels, and training parameter settings are appropriate for the user so the training can be adjusted.

In addition to modes, at least two different permission levels may be provided according to parameter values set in the permission module 598 of the present invention. The first permission level is "administrator", which may allow viewing and adjusting of training provided to a user including any of the aspects of the training (e.g., the curriculum, lesson content, training progression). A teaching professional, training professional, or clinician, may work with the user to improve the user's skills and performance. A clinician may want to increase the amount of training on chosen exercises to address the user's needs. Administrator rights by the permission module 598, allow the administer to customize the curriculum and exercise parameters. The second permission level is "User" level, in which the training normally operates, and there may be limitations set relating to how the user may operate and adjust any aspect of the training, which are set by default or adjusted by the administrator. The present invention may also include a standard training program for users, such as grouping of exercises that result in 90 different lessons arranged in a standard manner.

The training may operate in a story mode, which is one of at least 2 modes 383 selectable by the user or professional user. The story mode 383a is mode in which users are a generally passive and may be shown selected cartoon animations. The animations are aimed at illustrating or strengthening training concepts and reference knowledge such as the association between visual cues 512 of animals and the respective auditory counterparts 514 or a musical scale concept. The relationship between a visual cue 512 such as an animal character and particular musical sound 514 (or other musical aspect), that is related to that character normally does not change once established. The story module 32 may also request some participation from the user, for example, the user may be asked to sing by an animated cartoon character.

Exercise Task Parameters.

Cues and Probes. During an exercise task at least one probe may be presented, either alone or with a cue, and within a background context. An auditory or visual stimulus may serve as either a probe, a cue, or as part of the background. A stimulus that serves as a probe in one exercise may serve differently (e.g., as a cue) in a different task. In the context of an audio-visual stimulus, the sound and image (e g, animal character) are "paired" when the two are repeatedly associated with each other, both during various training components.

Figure 24:
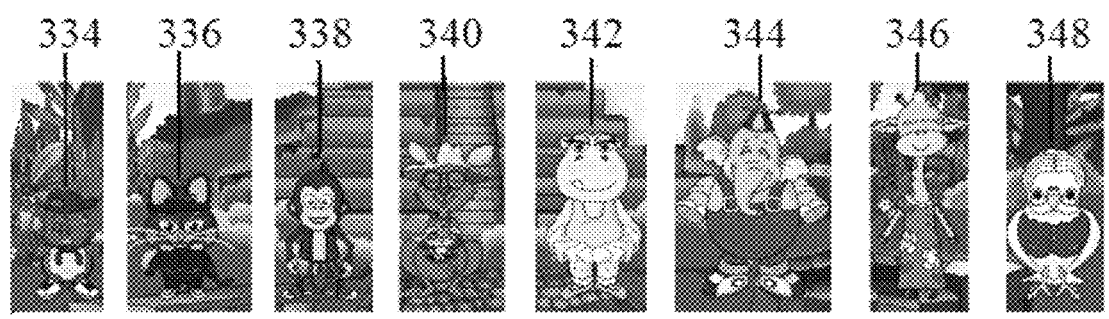
FIG. 24 is a pictorial representation of multiple animal/character buttons that may be used in the training of the present invention to allow users to provide responses.

Animal characters may be utilized as visual cues, as shown in FIG. 24. The animal characters may include the following: Do the Turtle 334; Re the Cat 336; Mi the Monkey 338; Fa the Kangaroo 340; Sol the Hippo 342; La the Elephant 344; Ti the Giraffe 346; and Miss Bird 348. The animal character buttons may allow the user to answer questions of the exercises such as "which animal corresponds to the following sound?" The Animal characters may be paired with specific sets of sounds, colors, or themes.

In one example of an exercise task, at least one visual cue may be presented (e.g., Ms. Owl) along with a question "Do I make this sound?" Questions may be presented in the same modality as the cue or in a different modality. The question may then be followed by an auditory probe stimulus (e.g. either the sound was previously associated with Ms Owl or a different sound). Alternatively, the visual cue may be followed by a question such as "Do I make any of these sounds?" This may then be followed by at least two auditory stimuli, presented sequentially, where 1 of the auditory stimuli can be the correct auditory probe (i.e., the "target"), and the at least one other auditory probe is incorrect. The incorrect auditory probe serves as a "distractor". Alternatively, two or more visual cues may be presented (e.g. Ms. Owl and Mr Giraffe), followed by a question, such as: "Do either of us make this sound?", followed by a sound probe. Alternatively, the question may be "Do either of us make any of the following sounds?" In these examples the user must select "yes" or "no" buttons that appear graphically on the screen or must say "yes" or "no" which is sensed and processed by the user interface module. Alternatively, the question may be "Which of us makes this sound?" followed by the sound probe, and the user can "click" on the correct animal cue.

Alternatively, the exercise may utilize at least one auditory cue and at least one visual probe. In one example, in one of low difficulty level exercise, at least one auditory cue may be presented (e.g., the sound associated with Ms. Owl) followed by a question "What animal makes this sound?" The question may then be followed by at least one visual probe stimulus. Using only Ms Owl as the visual probe is a very easy task and the user simply clicks on Ms Owl.

Background. Backgrounds may be visual, auditory, or multimodal. A background of an exercise may be unchanging (e.g., a simple scene in which cue and probe stimuli are presented). Alternatively, a visual background may be animated, or may have animated components. Auditory backgrounds may be musical tunes, various auditory stimuli that may or may not be related to animal characters, and may change over time or be repeated. There may also be no auditory background.

Task Difficulty. In the present invention of training, "task difficulty level' may be increased for a particular exercise by adjusting at least one type of difficulty: Type 1) the physical or perceptual content and parameters 502 of an exercise, and Type 2) the conceptual content or parameters 506 of an exercise. In general, Type 1 difficulty is more related to perceptual processing, and Type 2 difficulty is more related to cognitive processing and abstract thought ability.

The perceptual difficulty of the task can be adjusted, for example, by increasing the similarity or difference between the target and distractor probe(s), adjusting the interval between two sequentially presented cues or probes, adjusting the interval of presentation of any presented cues or probes, by increasing the number of cues or probes, by increasing the interval between the cues and probes, or by increasing the interval for which the cue or probe is shown or played (e.g. the duration for which the stimulus is presented to the user may be for 0.5 sec. or 1 sec.).

The conceptual difficulty can be adjusted by increasing the grade level of the language used, difficulty of theory based exercises, increasing the grade level of the concepts which are trained, and other aspects of the training related to abstract thought, or difficulty of the memory or other cognitive operations engaged by the training.

In a musical production category exercise, examples of adjusting these two types of difficulty parameters are as follows. As 2 to 3 repetitions of an exercise are presented, the physical parameters are adjusted 504 according to difficulty parameters stored in the perceptual module 502. For example, at least a portion of the song is played more quickly, or is adjusted to incorporate more difficult acoustical stimuli (e.g., words that are harder to pronounce or more complex rhythm patterns). Task difficulty level can also be adjusted 504 according to difficulty parameters stored in the conceptual module 506. by at least a portion of the song being replaced by a portion of song that comprises more complex types of words or concepts. For example, an increase in difficulty level 504 can comprise increasing the grade-level of the vocabulary that is sung. Alternatively, the new harder portion of a song may be appended to the end of the default song. Instead of making the physical parameters (that define musical aspects of the song) or conceptual parameters (related to abstract ideas or more advanced vocabulary) harder, difficulty level can be adjusted by simply substituting the song with an entirely new song exercise.

The user's singing may, or may not, be evaluated 524. Accordingly, the user does not have to meet any type of performance target criterion in order for the increases in Type 1 or Type 2 difficulty to occur. Task difficulty may simply be adjusted according to a predefined schedule, according to administrator or user preference, according to a training syllabus, and/or according to performance related to other exercise categories. Alternatively, the student's singing can be evaluated. This may occur during the singing by a teacher evaluating the signing output of the user, or by a microphone 552 recording the user's singing which is this submitted to signal analysis 564, such as pitch matching analysis. Alternatively, an evaluation of user performance on the task may be accomplished by the evaluation module 578 presenting the student questions about the content of lyrics. Type 1 and Type 2 difficulty can be adjusted 504 according to student performance which is evaluated by the performance module 590, or according to age, developmental stage, grade level, user interests, or otherwise.

In the Musical product exercise, Type 2 difficulty could also be increased by providing more complex concepts. For example, the song may start with an animal character singing "I can count to eight, I can count to eight, hear me hear me I can count to 8. Let's count together: 1,2,3,4,5,6, 7,8." In an increased difficulty song can be sung by the character where the counting is backwards "I can count backwards from 8, I can count backwards from 8, here me, hear me count back from 8: 8,7,6,5,4,3,2,1". In a further difficulty level the animal character can then instruct the user "now you count backwards", at which point the user would independently recite the numbers in descending order.

Although this is a singing exercise, various mathematical skills or concepts can thus be introduced.

Progression of Difficulty Level.

Increasing task difficulty, as has just been disclosed, can occur within an exercise task or across exercises, lessons, or other training components. In one embodiment of the present invention, training may start at a specific level as reflected by a background theme, for example, such as the pond level wherein tasks are presented with a pond scene background. While progressing through the training, the user may successfully reach subsequent training levels which are reflected by different background themes, for example, such as the "theatre stage" level. Subsequent levels may progress in difficulty or simply may change content of the training.

A user may not be required necessarily to start at a beginning level, which may be the easiest level, when starting training. A user may be able to start at a higher level depending on any performance analysis corresponding to the user. For example if performance related to a user's prior training indicates that the user has adequately mastered a particular level of the training, then the user may begin a current training session according to a later portion of the curriculum. The present invention may also or alternatively include a skills assessment module that is presented to a first-time user of the present invention. The skills assessment exercise or module may be utilized to determine a user's skill level and a user may begin the session at an exercise, module or lesson appropriate to the user's skill level. In some embodiments of the present invention it may be possible for a user to choose an exercise, module or lesson level to begin to utilize the present invention. The present invention may assess and analyze the user's use of the present invention during an exercise, lesson or module and may determine the level of the next exercise, lesson or module presented to the user in accordance with the information collected about the user's performance. The next exercise, lesson or module presented to a user may be of a more or less difficult level based upon this assessment and analysis.

The embodiments of the present invention may also vary in accordance with the characteristics of the user, including the attention span, prior musical training, performance level and other characteristics of the user. The grouping of exercises into modules, set or lessons, and the ordering and presentation of these to a user, may also vary in embodiments of the present invention, in accordance with the determination of the best means of training a user to improve cognitive skills through use of the present invention. Presentation of feedback and other aspects of the present invention may also vary in embodiments of the present invention. Measures, such as performance level success required to advance to a greater level of difficulty, and number of repetitions of an exercise that may be permitted by the present invention. Other measures may also vary between embodiments of the present invention, as may the persons authorized to adjust such measures. In some embodiments of the present invention measures may be adjusted by authorized persons, and in other embodiments it may not be possible to adjust some/any measures.

Progression of Difficulty Level.

In one embodiment of the present invention, a game may start at a specific level and environment, for example, such as the pond level. While playing the game, the user may be required to successfully reach another level and/or environment, for example, such as the theatre stage level. Levels may progress in difficultly from a beginning level to a final level. However, a user may not be required necessarily to start at a beginning level, which may be the easiest level, when starting a session. A user may be able to start at a higher level depending on any performance analysis corresponding to the user. So if a performance analysis, such as, for example a performance analysis of a user's prior experience using the present invention, indicates that the user's performance level is at a level beyond the easiest level, then the user may begin a session at a level of greater difficulty than the easiest level.

The present invention may also or alternatively include a skills assessment exercise or module that is presented to a first-time user of the present invention. The skills assessment exercise or module may be utilized to determine a user's skills in order to adjust the training curriculum and its parameters appropriately. In some embodiments of the present invention it may be possible for a user to choose how far into the training curriculum the starting lesson will be drawn from. The present invention may evaluate and analyze the user's use of the present invention during a training component and may determine the lesson, module, or difficulty level presented to the user in accordance with the information collected about the user's performance. The next training component presented to a user may be of a more or less difficult level based upon this assessment and analysis.

Setting Training Parameters.

Training parameters can be set and adjusted using age and gender matched population nonnative values. Training parameter values can also be set according to characteristics of a child, such as age, IQ, socioeconomic status, presence and type of developmental delay, sensory processing disorder, cognitive or language disorder, motor impairment, gender, language level, $1^{st}$ or $2^{nd}$ language, grade level, ability to read, or other relevant parameter. Training parameters can further be set and adjusted by assessing user's performance history.

Multi-Modal Evaluation of User Performance.

User performance can be evaluated in the context of population normative values which are age, gender, and otherwise appropriately matched. User performance can also be evaluated in the context of characteristics of a child, such as IQ, presence and type of developmental delay, a sensory processing disorder, cognitive or language disorder, motor impairment, language level, speech or hearing disorder, socioeconomic status, presence of a $1^{st}$ or $2^{nd}$ language, grade level, ability to read, or other relevant parameter. User performance can further be assessed in the context of a user's performance history. User performance may be assessed by a performance module 590, in the context of these other types of information which may be present in the user profile module 604.

A user performance module 590 may assess either individual or as composite or summary scores, the accuracy of a user's response, reaction times, and other measures. The training device 110 may be configured to operate in a school or home environment with external devices that sense data from users and communicate either wirelessly 556 or through a sensor/stimulation module 558. One such as device may be a portable EEG device, preferably having between 1 and 10 active leads (and a reference and can collect data before, during, and after training EEG data after training can be compared to before training to show the effect of training on a user.

Human Avatars.

The training may use animated animal characters and a video game format in order to provide a fun approach to training for young users. One disadvantage of this approach is that some training exercises require a user to mimic the actions of the animals, and the correspondence between an animal's body and the user's body may not be clear. For example, showing a monkey touching its toes with its hands may evoke the correct response in some users, but may be vague to others who will not copy the animal correctly (e.g., they may simply bend over and fail to try to touch their toes). For this reason, an advantage of the current invention that is can present human avatars that mimic the animal's behavior. For example, when an animal character brushes its teeth, the human avatar can turn and look at the animal and then start brushing its teeth as well. Another advantage of the human avatar is that child who sees another child (the avatar) copying an animal character then the child may be further encouraged to participate. This effect is similar that seen with the canned laughter used for TV shows, which encourages the at-home TV audience to laugh along as well. In one embodiment, human avatar feature may be turned on or off.

Single or Multiple User Training.

The training can be oriented for 1 or 2 or more users. In one embodiment, using the training by more than one user, the ability to set up multiple user profiles, may be limited by the training program, and only may be permitted when an administrator provides this feature to occur. The training may be designed to operate differently when multiple users are engaged by the training. For example, an exercise that requires singing may be implemented similar to the approach adopted by karaoke where a dot is used to indicate what word is sung, or the words are highlighted when a user is supposed to sing them. When 2 or more users are participating in the exercises then the dot may appear with a particular color which is associated with each user. Alternatively, an animal character can be associated with each user, and the animal character is shown singing at times when a particular user is supposed to sing and can otherwise be used to indicate to a user when a particular user should respond to the training. Other manners of indicating which of the users is supposed to respond to the training, at a particular time or in response to a particular task, are possible.

Training Exercise Categories.

Many training components can be mostly or entirely passive. These may also require a very simple response, or a response that is different than what is required during active training exercises in that it is not training or testing the skills of a student. An example, of such a response is directing a user to "click to continue". This is done simply to keep the user engaged and is not related to task. Additionally, in a passive training a user may be asked about user preferences: do they want a training component such as a story module to be repeated; do they want to be presented with a harder difficulty level; do they want a training component to be skipped, etc. In passive training the user is usually not required to make response. Although not required, a user may sign along with the characters in an animated story and may be asked questions as part of the song, but the song will progress regardless of whether the user responds. For example, the song may ask "Do you like blue" and then follow up with "We do", without expecting the user to make a response by answering this question.

During active training exercises, users are asked to make at least one response or selection. A response may be a movement such as clapping, singing, or answering a question. A selection may be a response that indicates a choice made about two or more stimuli shown to the user. The response may or may not be evaluated. If evaluated, then feedback may or may not be provided. Both evaluation and feedback may be based upon only one response/selection made by a user or a set of responses/selections.

Passive Training.

There are at least two different training components that constitute "passive training".

Passive Stories and Instructional Cartoons. Animated stories (cartoon or video) and instruction modules, deployed by the story manager module 606, may precede, or be presented between, active training exercises. In the case of stories, the audiovisual stimuli (e g animal-sounds pairings) that will be (or have been) presented during active training components may be used. Across many different stories, the student may become familiar with the audio-visual (animal-sound) associations known as "pairings". A story also serves to introduce a visual cue (animal character) or training theme. In this manner a user becomes familiar with, for example, the visual cues, animal characters, sounds, animal-sound pairings, exercise themes and environments, training concepts and goals, various training, and music-based concepts used in the active training exercises.

In one embodiment, a story entails having the animals say their names and sing their sounds, in the context of the storyline. For example, Tea the Giraffe may like to drink Tea, and may like the letter "T", and may like to go on a trip with the Elephant La who kept "La-fing", and so on. Mnemonic-oriented stories aid the user in accomplishing the active training exercises, by reinforcing the memory of the animal-sound pairings. In another embodiment, an animated story may include the animals walking to a theater to put on a play, and along the way they meet other characters. This can be followed by a story where the animal characters enact a play in which they each introduce themselves and make their sounds.

Passive Audio-Visual Pairing Exercises (passive cross-modality training). An example of this training component is illustrated by the method shown in FIG. 39. The training begins by assessing any user parameters that have been stored in a user's profile 500. Part of step 500 may be to use this information to select or adjust training content, parameters, or curriculum. If there is a story module associated with an exercise that is about to be presented to the user then the story can be presented to a user 501. If not then selected parameter values associated with the exercise may be adjusted 502 so that exercise components 510-526 occur as intended. In the exercise, an auditory cue 512 (e.g., a tone) is presented J times, for a duration of K seconds and a corresponding visual cue 514 (e.g. an animal character) is shown. During the exercise audio-visual cue pairings are sequentially presented for at least N animals, with N set to at least 2 (by step 502). The exercise can include auditory and visual context and instructions, for example, presenting, "Hi, it is nice to meet you, this is the sound I make", followed by the audio cue "La". The user is not asked to make any response such as choosing which of the animals made that sound. Rather the user merely watches and learns the audio-visual pairings through repetition. As dictated by step 502 or as set in a default manner, for a percentage of trials, the visual cue 514 may be presented F seconds before or after the tone cue is presented, rather than being shown simultaneously as is defined for delay "D" parameter 513. Although FIG. 39, shows additional steps 518-526, in this exercise example the exercise follows path "2*e*" and returns to step 502 to determine if any adjustments should be made, and if the exercise should return to step 510 with the same or new stimuli, or end 527.

The first audiovisual cue 510 of an Exercise may constitute an animated animal saying "Hello my name is LA the elephant, and my sound is LA". The "LA" is sung by the animal. The second audiovisual cue 510 of the exercise may constitute an animated animal saying "Hello my name is TEE the Giraffe, and my sound is TEA". The TEA is sung by the animal. The auditory stimuli "Hello my name is TEE the Giraffe, and my sound is TEA" may all be considered the auditory cue 512. Alternatively, "Hello my name is TEE the Giraffe, and my sound is" may be considered an informational or question component of the exercise task 511 and "TEA" by itself serves as the auditory cue 512. In this case, the informational or question component of the exercise 511 may be information as just described or may be embodied as a question "Hello my name is TEE the Giraffe, did you know that I sound like this?" 511 which is then followed by the auditory cue 512. This exercise may constitute presenting audiovisual stimuli 510, with each animal corresponding to a selected musical sound (e.g., Doe, Ray, Me, Far, Sew, La, Tea).

In some exercise tasks additional visual cues may exist on the screen, but are relatively, or completely inactive. For example, while Tee the Giraffe is talking and making sounds, LA the elephant may be sitting, or doing something else on the screen. These other types of visual cues may be presented as part of the background that is selected 509 which is presented with the audiovisual cues 510, the parameters of which may be fixed or which may be adjusted 509. This allows the student to acknowledge that the other animal does not make that sound (and may even cause the student to mentally rehearse the sound that is not being made which is associated with the background animal). The audiovisual stimuli may be repeated a selected number of times, after which the exercise is terminated 527.

The set of exercise stimuli may be selected, in step 502. While one set of animals are associated with a first set of sounds (Doe, Ray, Me, etc), a second set of animals are associated with a different set of sounds such as musical notes played by a piano. For example, C,D,E,F,G,A,B,[C], etc, with the bracketed 'C' indicating that the last note is an octave higher than the first note. C and [C] are associated with a different animal. Accordingly, additional stimulus sets may be used in order to create a larger set of audio-visual stimuli (e g, animal-sound pairs).

Each animal may also have a rhythm or dance move associated with their character which is shown here. In active exercises the user may be asked to judge if a dance move or rhythm is correct for an animal character The passive audio-visual pairings may be presented as simple animated sequences, but are preferably implemented within a story context in order to elicit and maintain increase a user's interest level. This approach allows the exercise to seem more fun and less like cognitive training.

In an easy level of this exercise, only 2 or 3 animal-sound cue pairings may be presented to a user, and the presentation may be limited to 3 repetitions. Other difficulty levels may adjust these training parameters to adjust the difficulty of the information being reviewed or for other reasons.

Active Training.

In a preferred embodiment there are 6 categories of active training exercises.

Rhythm Exercises.

Figure 15:
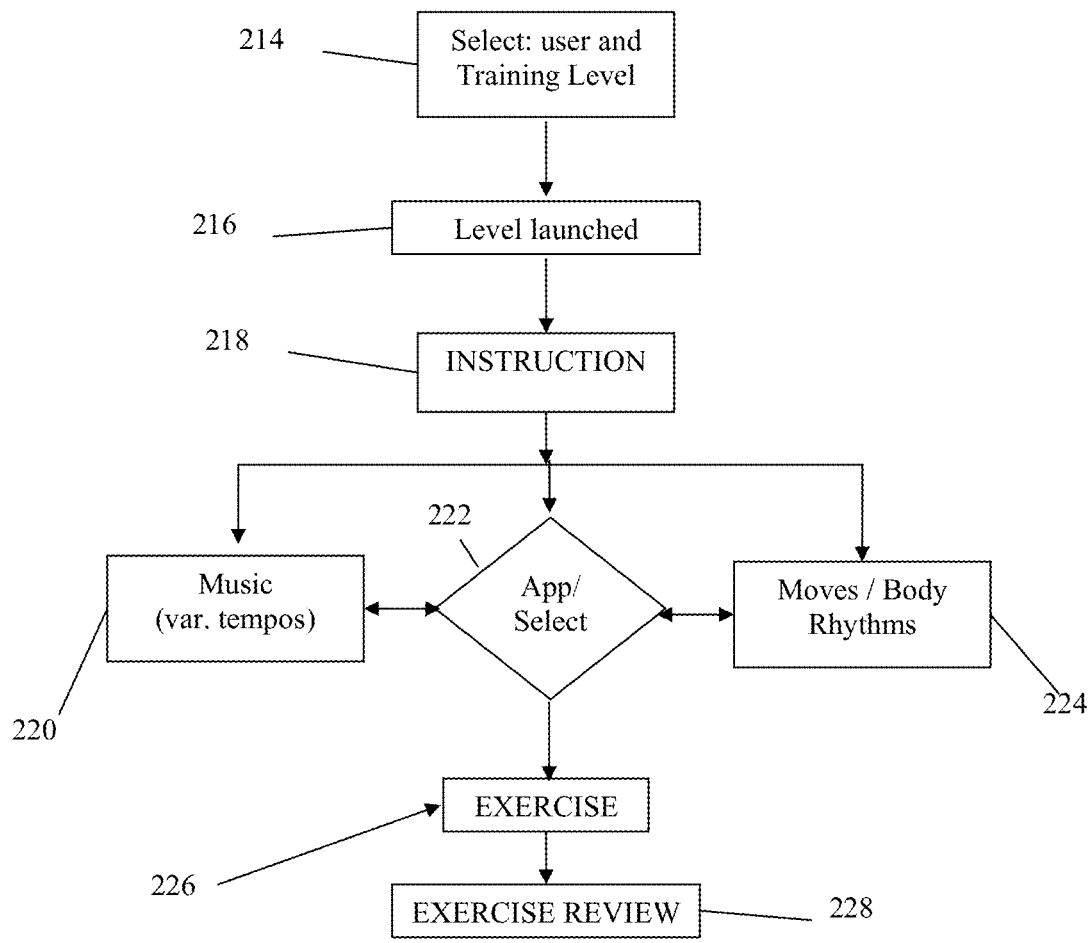
FIG. 15 is a flow chart showing the provision of training according to a Rhythm Exercise category as may be implemented within a lesson.

An example embodiment of a rhythm exercise (RE) 76 of the present invention is shown in FIG. 15. The user, or curriculum, may select the training level 214 that is appropriate for the user. For example, the training starts by a user selecting their profile by entering their user info for from a list of users, and then the training is adjusted according to a user's profile information. The present invention may initiate the training at the appropriate level 216, which may involve presenting instructions 218 to a user. The present invention may pseudo-randomly or in a fixed manner select appropriate training exercise, content, parameters 222 according to training parameters. For example sounds and tempos are selected 220 and body movements and/or body rhythms are selected 224 with their corresponding animal character. In the training exercise 226, the user may be required to reproduce the moves of the animal character corresponding to a specific rhythm 226. The present invention may then provide exercise review 228, whereby a set of questions relating to the exercise are posed to the user, using an evaluation module 578. The Rhythm exercises may train a user to distinguish between at least two different musical rhythms.

In an embodiment, in FIG. 15, the step of providing the review exercise review 228 may be skipped and performance on the exercise task may be accomplished using the performance monitoring module 590. The user's performance on the exercise may be used along with information provided by the progress tracking module 592 to then end the particular exercise, or repeat it by starting from either step 218 or 222, although normally the exercise is done only once per lesson. If repeating the exercise then steps 220, 222, and 224, may occur followed by steps 226 and 228. The arrow between 220 and 222, as well as between 222 and 224 are bidirectional since the exercise may send information to the routine choosing the music and the subroutine may then send information back to the exercise's main routine.

The invention may contain various rhythm exercises 76 that promote training using different aspects rhythm such as physical aspects (e.g., where a user may repeat, identify, or discriminate aspects of musical timing, sound patterns, regularity, beat, tempo, alternation, repetition, and themes) and abstract understanding of rhythm (e.g. understanding of: metric hierarchy, rhythm based expectations, concepts such as on and off beat). Rhythm Exercises RE1 to RE8 are listed in the table of FIG. 10, in the column labeled "Rhythm" as part of a curriculum. The following shows example embodiments of those exercises.

RE1: The user is instructed to copy physical movements produced one or more animals. For example, a user may be instructed: "Each animal friend walks a little different. You have to make the same moves as the animal Doe The Turtle makes this move. Can you do that too?" The user then attempts to mimic the movement.

RE2: The user is instructed to make different movements. For example, the user may hear the instructions "jump jump jump" or "move your arms, arms, arms", and may see an animated animal and child avatar making the movements that the user is supposed to mimic.

RE3: The user is instructed to choose one visual animal probe stimulus that marches with the same beat as either an animated child, a tune that is being played or both. The user may also be asked to determine whether an animated character is correctly moving to beat that is being played, for example, by selecting "yes" or "no" when the game asks "Is Ms Owl walking correctly to the beat?" As the task progresses the user may be told to walk in a manner that is normally shown by different animals-Doe The Turtle, then La the elephant, etc. so that the movements change across time.

RE4: The user is instructed to "sit on the floor and keep the beat". An animated human avatar may appear in the upper corner showing the moves that the user should make. The auditory instructions may tell a user to "Blink blink blink your eyes" or "Wave wave wave your hands".

RE5: The user is instructed to "Dance like me". During the exercise, different characters perform different dance moves to different rhythms. The user is instructed to emulate these movements.

RE6: The user may be instructed to "Copy my moves". During the exercise the user must copy the moves made by the character, such as, clapping, lifting arms etc. Different animal characters may unique movements and rhythms.

RE7: The user may be instructed to "See and feel the beat in music". During the exercise the user is instructed to place objects in at least 1 target area of a device display. Objects are clustered in sets of 1, 2, 3, 4, or more. For example, there may be four boxes shown on the top of the display. The boxes contain from 1 to 4 yellow stars. When the user clicks on any of the boxes this causes the same number of stars to go to a target area. If the user clicks on a 1-star box, then on a 4 star-box, then 1 star, then 2 stars, a beat will be constructed in the target area of the screen. The training will then play the resulting rhythm: one note-pause-4 notes-pause, and so on. Accordingly, the user builds beats by building different combination of boxes-of-rhythms. In this example, all the yellow stars represent the same note. Rather than simply having yellow stars, there can be blue stars or other colors and shape combinations will emit sounds with different characteristics (e.g., different durations). In other words, the different colors and shapes can reflect different beats, notes, or sounds. However, since this is a beat exercise, the characteristics should relate to promotions of skills related to beats and timing. One object of this exercise is to allow users to build different beats and then see the visual representation of the rhythms they hear. Several menu options may be provided such as "build beats", "play beats", "stop sounds", and "clear", which clears the previously built beat.

RE8: The user is instructed to "Create the beat of the music you hear". This exercise is similar to RE7 except that the user is instructed to attempt to build the visual representation which matches a beat that that is generated by the training program.

Figure 16:
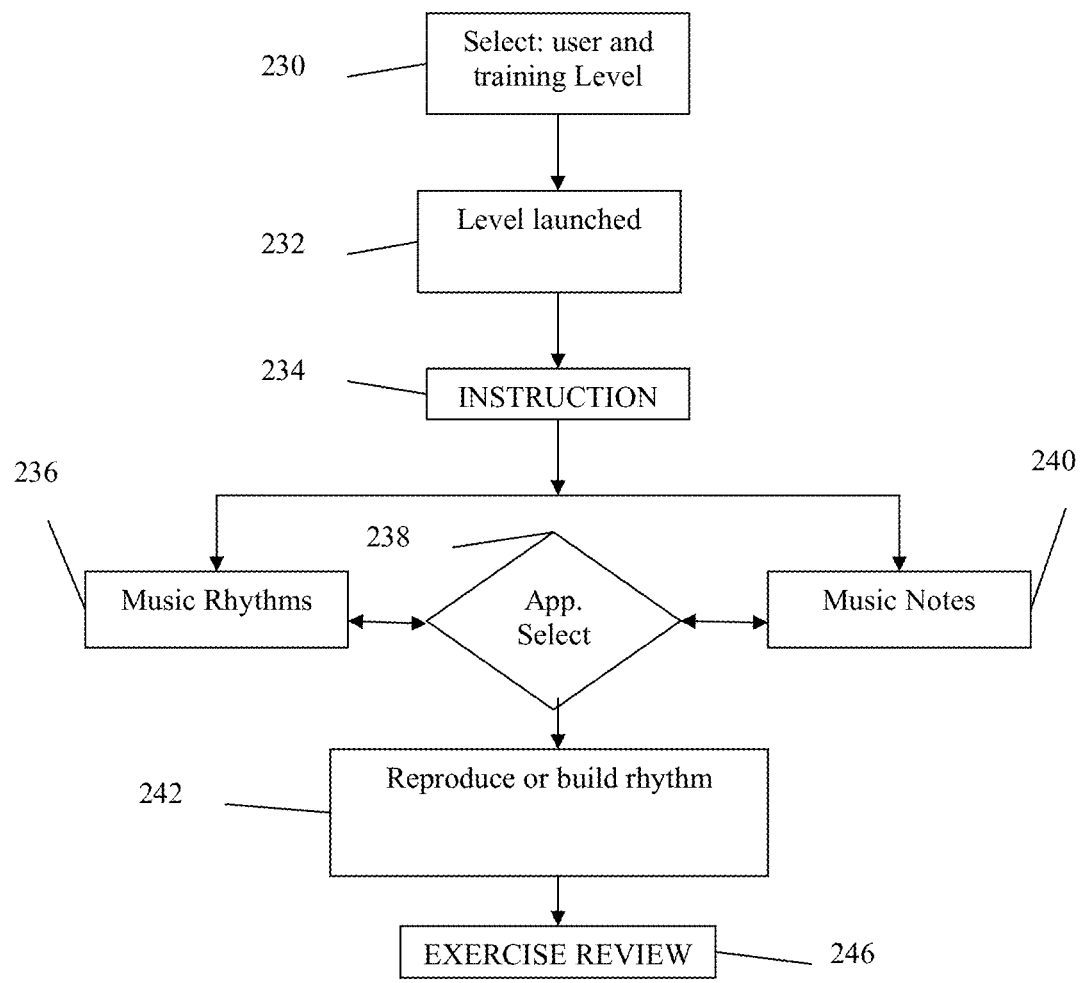
FIG. 16 is a flow chart showing the provision of training according to a Rhythm Building exercise of the Rhythm exercise category.

An alternative embodiment of the present invention, having both a rhythm production exercise and rhythm matching exercise aspects (combining RE7 and RE8), is shown at FIG. 16. In the first step, the user, or the curriculum, may select a training level 230 and/or rhythm exercise. If the user has created a user profile, then by identifying the user, the training can set training parameters which are appropriate to the user. In the next step, the present invention may initiate training at a level 232 chosen as appropriate for the user (e.g. a particular lesson). The training may then provide instructions 234 to the user. Training may then randomly, psuedorandomly, selectively, contingently, or in a fixed manner operate to select appropriate training parameters 238, rhythms 236 and musical notes 240. The background may be a musical a staff. In this example, the user may be required to build or reproduce a specific rhythm 242 in a manner similar to that disclosed for RE7 and RE8. Training may then perform the step of exercise review 244.

It is an advantage of the invention that various aspects of rhythm, body movement, gross motor movement, and fine motor movement, are explored by the different illustrative exercises RE1 to RE8. For example, in RE1 "rhythm mimicking" and lower body gross motor movement is emphasized where the user must imitate the way that different animals walk and should do so with the same cadence as the animated animal. In RE2, the user may be instructed to move upper body parts as well as lower body parts, such as marching while raising and lowering their arms according to a musical beat. In RE3, the user may be asked to select one of several animal probe stimuli, so that the movements shown by the probe match the movements shown for an animated visual cue. In an alternative of this exercise, there may be a musical beat and the user is asked to select an animated character that is moving correctly in accordance with the musical beat. Again beat matching, and assessment of auditory and visual timing, is trained. In RE4, the user is sitting and the motor movements are more related to fine motor movement such as blinking, or hand clapping, to the beat of a rhythm. Younger users (e.g. 4 year olds) may find it especially difficult to clap to a particular beat.

Accordingly, RE1 and RE2 relate to rhythm generation and gross motor movement using various portions of the body, RE3 relates to rhythm matching, and RE4 relates to rhythm generation and relatively finer motor movement than RE1 and RE2. RE5 relates to dancing to a rhythm, which allows more freedom than RE1, 2, and 3, and allows the user to creatively interpret and feel rhythm, or to somewhat ignore rhythm (which may be important if the user is having trouble with the other rhythm exercises and being a little frustrated). RE7 relates to abstract rhythm generation in a manner that allows the user to create different rhythms by selecting visual tokens which are then placed in an area of the screen that indicates the token will be "played". RE7 is therefore a cross modal exercise where visual patterns of symbols chosen by a user are played as their respective auditory patterns. In RE7, the user can create whatever rhythm patterns they wish and the idea here is to emphasize how abstract visual symbols can be represented in a different modality. This also allows the user to be creative and experiment with making music. In RE8, the user is asked to match tones that are being played, which requires inter-modal comparison in order to select visual pattern probes that match the auditory rhythm cues.

A user's rhythm may be assessed in relation to a rhythm template by evaluating whether a particular component of the user generated rhythm occurs before, concurrently, or after a corresponding component of the template rhythm. Rhythm performance can be assessed as the average delay error (measured as user component relative to template component), calculated using responses that came before, after, or both before and after (combined). The evaluation can be done for rhythms produced either simultaneously in real time, or matched/repeated by a user after a delay.

By presenting the cluster of rhythm exercises to users, both conceptual and physical aspects of rhythm are thereby explored across these exercises. Further, users are not forced to simply look at a computer screen or teacher, but are also able to move their bodies, blow off some steam, have fun, which promotes remaining engaged by the training.

The parameters may be adjusted to increase difficulty, or new types of rhythm exercise themselves may be presented. For example, the beats that are generated may be increased in difficulty by having longer sequences, faster tempos or more complex rhythms, or more complicated physical movements. The progression from easier to harder levels of difficulty may linked to evaluation of a user's performance or may simply occur according to a predetermined curriculum schedule, or user preference, or otherwise. The difficulty level may be adjusted only for a subset of rhythm exercises. The body parts a user may be instructed to move can include: hands; arms; shoulders; feet; legs; head; or whole body. The musical rhythm may have its tempo adjusted to change difficulty. The difficulty may adjusted according to the particular one or more body parts that the user is expected to move to the rhythm.

If user behavior is measured or evaluated, then this can be achieved by having a human observer input a score related to the performance via the user interface module 550. Alternatively, capture and evaluation of behavior may be achieved using webcam 554 with motion capture/evaluation routines 562, or through use of sound recording devices 552 and sound processing module 564 (to measure hands clapping to assess rhythm generation performance) or other types of sensors 558 (motion, accelerometer or position sensors worn on the user's body or clothing, a touch screen which the user may tap or a pressure sensitive floor mat) with assessment by the performance module 590. The sound processing module 564 may contain a rhythm recognition module which evaluates how well the rhythm is produced by a user, for example, by comparing the rhythm made by a user to a template.

When performance is evaluated, the response may be evaluated by the performance module 590 according to a self-nonnative reference of the user's past performance stored in database 570. Alternatively, the response data may be evaluated according to an appropriate population nonnative reference stored in database 570.

Figure 38D:
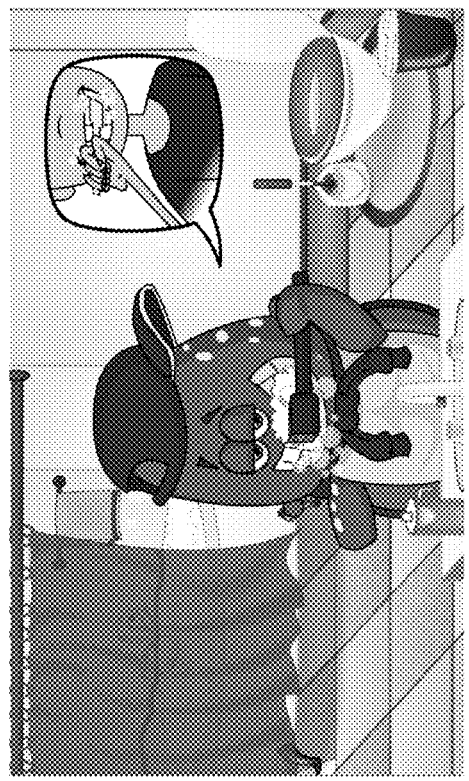

In addition to the visual cues 514 and probes 522 of animated characters which are used in many of the rhythm exercises in a preferred embodiment of the invention, the invention may show an animated human avatar that mimics the movements made by the animal (see FIG. 38D).

Musical Ear Exercises.

Musical ear (ME) exercises 80, may train a user to associate the particular musical cue 512 with, or without, a visual cue 514 of animal character. For example, the target musical note C4 may be associated with a turtle character. The training may use tones or vocal representations relating to musical notes, for example, such as Do-C4, Re-D4, Mi-E4, Fa-F4, So-G4, La-A4, Ti-B4, Do-C5, etc. Each of the above musical notes may be represented respectively by a visual-cue 512, such as visual-character or shape or image or color, and said corresponding visual shape/character/color which is associated with a sound-cue 512 corresponding to the musical note. The exercise may provide instructions and tasks designed for user to recognize the relationship between tones and characters.

The ME exercises 80 may train a subject to identify the visual-auditory pairings by requiring that a user chose between different sound candidates, for example, distinguishing between C4 (or Do) and other musical notes, for example, such as D4, E4, F4, G4, H4, A4, B4, C5, etc to correctly recognize one or more sound cues and/or probes rather than choosing incorrect alternatives.

Figure 18:
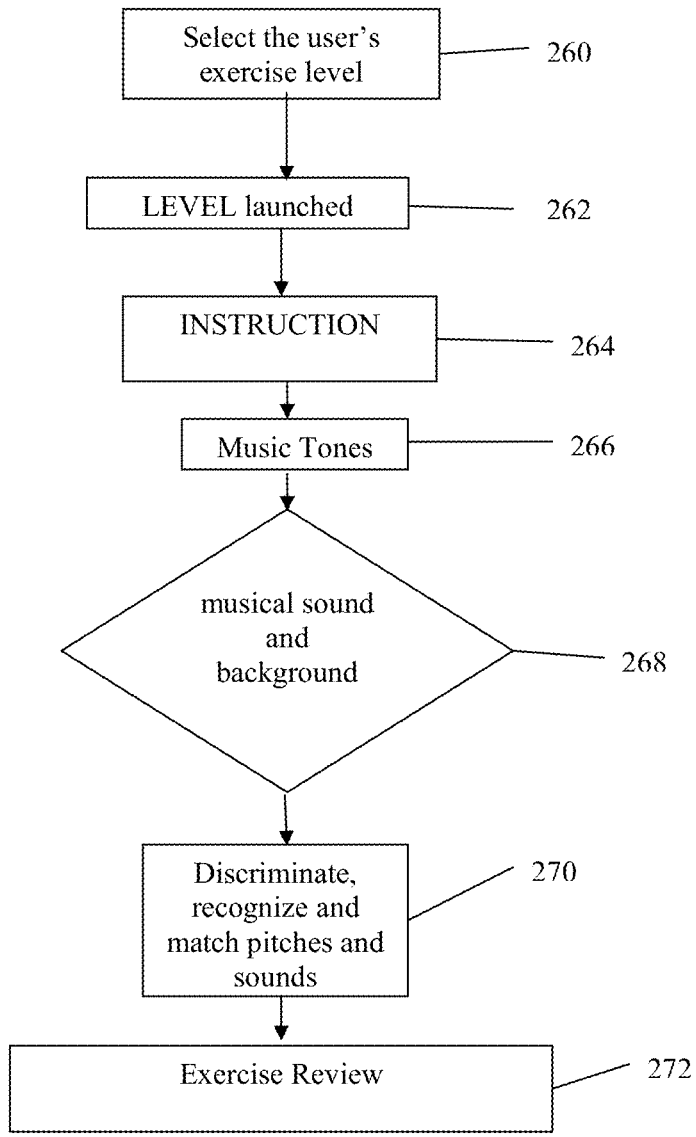
FIG. 18 is a flow chart showing the provision of training according to a Musical Ear Exercise category.

The training of the present invention may include an ME exercise that may be operable in the manner shown in FIG. 18. The user or the curriculum mode, may select the exercise level of lesson in step 260 as appropriate to the user. The exercise is started at the appropriate level in step 262. Instructions are then provided 264 to the user. The training manager 574 may select musical stimuli in step 266 in presented these against a background environment in step 268. Different background environments may be used to signify different levels of the training. During the exercise training 270 the user may be instructed to discriminate, match, recognize, or otherwise make choices and selections about musical stimuli according to the exercise, and usually in relation to animal characters. The exercise may be followed by a review 272, in which set of questions are posed to the user.

In one embodiment, musical ear exercises will require responses from the user which are related to audio-visual pairings that have been previously established. As shown in FIG. 39 these relationships can be established either in steps 500 to 514 or otherwise such as in a story module. In some exercises a cue 512 and/or 514 is presented simultaneously with the probe 520 and/or 522 (e.g., the delay implemented in step 516 is set to zero), while in others the probe presentation follows the cue presentation (e.g., the delay implemented in step 516 is set to a positive value). By requiring a user to match an auditory 520, visual 522, or audiovisual probe 518 to cue template (512 and/or 514), the success of the consolidation of audiovisual pairings may be assessed by evaluation of the user response 524 evaluated by the performance module 590. In order to maintain user interest, indirect goals may be used in some exercises. For example, correct user responses can lead to various rewards. In one example of an indirect goal, a child avatar is helped to cross a pond when the user provides correct responses to the exercise task. In this case, correct answers result in building a path across the water-see FIG. 37b). In other example of indirect goals, a racecar can progress around a track as a function of a user's correct responses (see FIG. 37c).

Matching Tones-intra-modality (cue-delay-probe). In one exercise, following operation according to FIG. 39, an auditory cue 512 (e.g. "I like to say LA, who am I?") is presented, where at least the portion of the cue "LA" is repeated J times. Alternatively the auditory cue is a compound cue, comprising a first cue component ("I like to say"), a second cue component, the sound "La-A4", and a third cue component "who am I?" After a delay of S1 seconds 516, a first audiovisual probe 518 (e.g., a sound probe 520 combined with visual probe 522 of the animal that makes that sound) is presented. After a delay of S2 seconds 523, the operation follows path 2h and a $2^{nd}$ audiovisual probe 518 is presented. The user may then be asked 519 to decide if the first or second audiovisual probe matched the auditory cue 512 (i.e. the sound component of one of the audiovisual probes matches the auditory cue 512).

The instructions for this task, such as "You will hear a sound and then see two animals, choose the animal that makes that sound", may be presented in step 511 before the user sees the cue and probe stimuli. Alternatively a question may be posed in step 519 after the cue and probe stimuli are shown, such as "Can you pick the animal that made that sound?" Additionally, the question may also be posed to the user both before and after the cue and probe stimuli are shown using both in steps 511 and 519.

The user selection can be assessed 524 and this may lead to feedback 526, or the step of providing feedback 526 may be skipped so that the method returns to step 502. This training paradigm is intended, in part, to train the auditory working memory, sensory memory of the user. The auditory cue 512 serves as an auditory template that must be matched by the auditory component 520 of the audiovisual probe 518. It also is intended to serve to strengthen the audiovisual pairings.

The difficulty level of this task can be increased by adjusting a number of parameters of the exercise in step 502. For example, 1) the duration of the cue or the probe may be shorter (usually the probe); 2) increasing the number of probes that are presented, (either sequentially or simultaneously when the probes are only visual); 3) increasing the delay between a cue and probe; and, 4) decreasing the delay between sequential probes (one of which is reflects the correct choice of a task).

Cross-Modality Audio-Visual Matching with Delay. In another embodiment of the training, an exercise has an auditory cue 512 (e.g. "I like to say LA, who am I?"). After a delay of S1 seconds 516, a first visual probe 522 is presented (e.g., an animal that has previously been paired with a sound), but no auditory probe 520 is presented. After a delay of S2 seconds 523, a second visual probe 522, is presented, again without an auditory component 520. Alternatively a first and at least a second visual probe may be presented at the same time. Task difficulty may be increased by adjusting the parameters as was disclosed for the "Matching Tones-intra-modality (delay cue-to-probe)" example. Among other benefits, this task is intended to train the auditory working memory of the user. The auditory cue 512 serves as an auditory template that must be matched by the memory of the sound which was previously paired with the visual probe 522. Additionally, the user must hold the auditory probe 512 in memory while assessing the visual probes 522.

Music Ear exercises are listed in the table of FIG. 10, in the column labeled "Musical Ear" as part of a curriculum. The following shows example embodiments of some of those exercises, as well as alternative embodiments:

ME1: Audio-Visual Matching Simultaneous. A sound cue 512 is presented J times for a duration of K and at least N visual probes 522 (e.g., animals) are simultaneously shown, with N set to at least 1 (using 1 lets the user simply associate the animal probe 522 with the sound cue 512). Prior to the first task of the exercise, the user may be presented with instructions for the task through a speaker 12 in step 511. For example the user may be told "Today you will hear some sounds. Can you pick the animal that matches that sound?" After the instructions are presented 511, a sound cue is played 512 and the user must select which of several animal cues 522 made that sound. If the user selects an animal, and this response is evaluated 524 as correct, then the user is provided with positive feedback 526 such as being told "good job", while if the response is evaluated 524 as incorrect then the user may be given feedback 526 in which the user is asked to try again. Negative feedback may also be provided but the preference is for this type of "try again" neutral feedback, or providing no feedback, for incorrect answers, at least for young users. No adjustment is made in difficulty as the training moves through step 502, then and various components of steps 510 and 518 may be again repeated. In a particular exercise, users may be allowed to "try again" up to 'E' number of times, as dictated in step 502 (as implemented under control of the training manager 574) with E normally set to 3. If evaluation of a user profile 500 indicates that the user is cognitively or physically challenged, then E may be increased accordingly to improve the match of the training with the user's profile, skills and progress. When a user performs the task correctly, step 526 may return to steps 510 and 518 through step 502. In the next task iteration, a new auditory cue may be shown with at least 1 new visual probe 522 (animal) or auditory cue 512, replacing one of the original task stimuli. In this manner, all the visual probes of an exercise "test-set" will eventually be presented to the user.

The exercise can become more difficult, for example, by presenting at least N animal cues in step 522, where N is increased from 2 up to 8 or more animals. Additionally, on a percentage of trials, the animal choices may be presented F seconds after the cue tone is presented by setting a delay parameter in step 516 to a non-zero value. Difficulty may be increased in step 502 contingently upon the user successfully selecting the correct answer at least X % of the time, where X may be adjusted as a function of age or otherwise.

ME2: Audio-Visual Matching Simultaneous/delay. Similar to ME1, in this example exercise, the user is instructed to identify which animal probe 522 makes a particular sound 512. There can be between 4 and 8 animal choices (see FIG. 37a). In one embodiment of this exercise the animals may be shown when the sound is played (delay parameter in step 516 is set to a zero value). In another embodiment the animals are shown after a delay of M seconds. The exercise may continue until the user has selected J correct animals, as dictated in the parameters 502 that guide the training manager 574 in providing the exercise. Additionally, if the user produces N (e.g., 3) wrong responses in a row then the training progresses to the next exercise under controlled of the training manager 574.

Figure 37B:
FIGS. 37a-d show 4 pictorial representations of exemplary game screens of the training.

ME3-ME5: These exercises are similar to ME1 and ME2 but have indirect goals designed to increase the entertainment of the exercises. The training is designed to discourage user boredom after playing the ME1 and ME2 game-exercises for 5 to 10 minutes. For example, in ME3 a tic-tac-toe (also known as 3 in a row) board is shown embodied as a set of Lilly pads (FIG. 37b). The indirect goal is to help an animated avatar cross a river by making a path through a set of Lilly pads. The user must select which animal makes a particular sound, but the goal is not simply to choose the animal that makes the sound but also select from multiple Lilly pads having the same animal (from 2 or more choices of the same animal) which will allow the character cross the river. To provide visual feedback, if the user chooses correctly then the Lilly pad turns green otherwise the Lilly pad turns red.

Figure 37D:
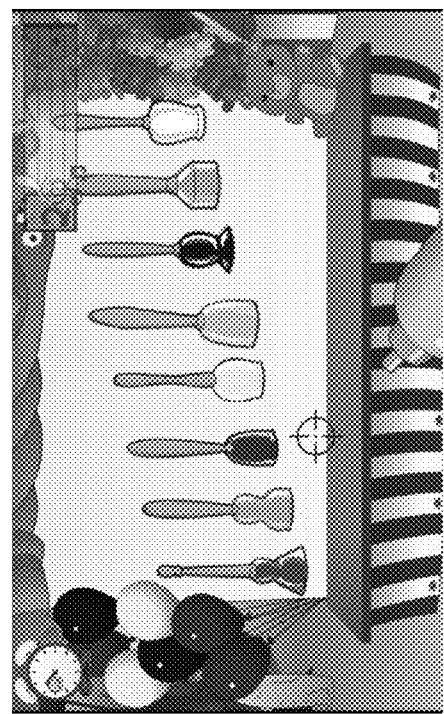
Figure 37A:
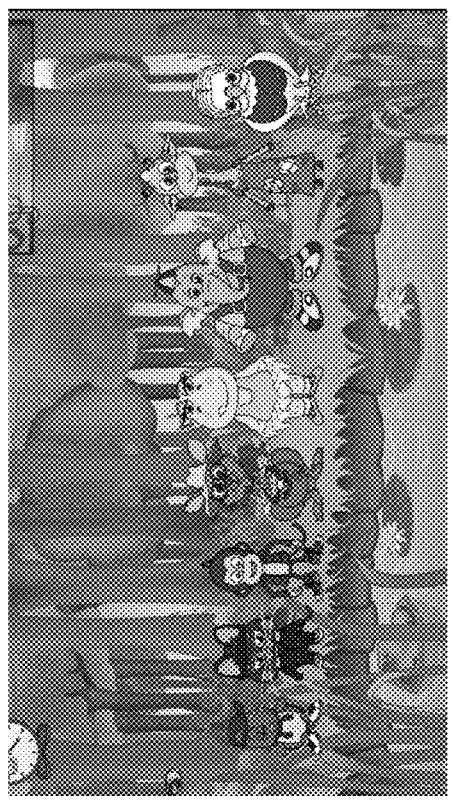
Figure 37C:
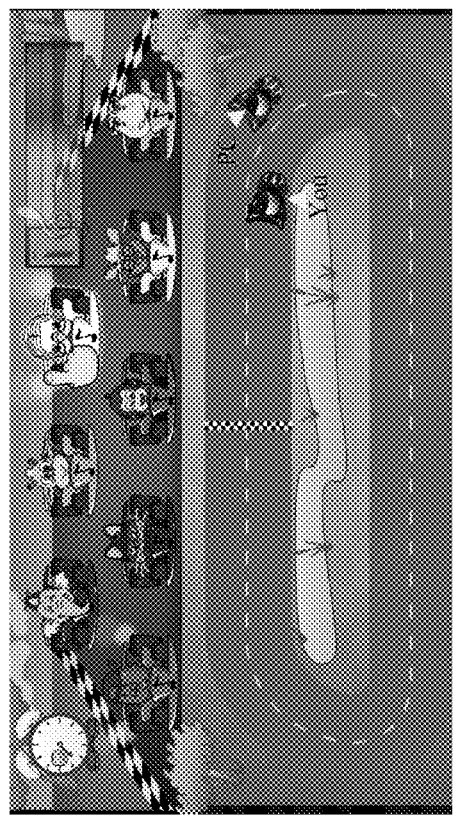

ME4: In ME4 when the user correctly identifies the sound cue, using the animal probes at the top of the screen, a car progresses around a track towards to reach a finish line (FIG. 37c). If a user incorrectly identifies the sound then the other car advances. This continues until one car wins or a time limit runs out. In addition to the visual feedback provided by the car positions, auditory feedback may also be provided.

ME5: In this exercise there is a set of visual stimuli such as animal characters, musical instruments, bells, or other group of similar items (FIG. 37d). In the case of bells, the user is told to "listen carefully and try to play the bells back in the right order". The bells ring in a particular sequence. Afterwards, the user may use the computer mouse to aim a water-cannon at the bells. Clicking the mouse button results in shooting/selecting any of the bells to make them "ring" (both visual and sound feedback may occur 526). The user must do this according to the previously shown sequence. Task difficulty may be increased by increasing the number of bells, or length/complexity of bell sequences. One aspect of this music-based task is to provide memory training.

In an example embodiment, during each ME exercise the training presents one cue stimulus in at least a first modality 512 or 514 at a first time, for a selected first duration. The exercise also includes presenting, to the user, at least one probe stimulus in at least a second modality 520 or 522, at a second time and for a selected second duration (which may be the entire length of the exercise). The probe stimuli may be visual 522 or audiovisual 518, while the cue may be only visual 514 or auditory 512. The musical ear training can include a set of exercises in which least one visual cue or the probe stimulus is followed by, preceded by, or simultaneously presented with, a sound stimulus. The user is normally instructed to provide a response that reflects a choice about the at least one probe stimulus. This response should be made in response to a particular question or instructing. The training may evaluate the user's choices and selections to determine if the user response was correct or incorrect.

Theory Exercises.

Theory exercises (TE) 82 of the present invention train various themes related to music theory and often relate to symbolic and spatial relationships. A TE exercise may train a user to associate the music scale with an image of the human body, to recognize and distinguish between the lines and spaces of a musical staff, to recognize the relationship of the sounds and animals in the context of a music staff, and to place the animals on locations of the music staff according to tones that the animals represent.

Figure 19:
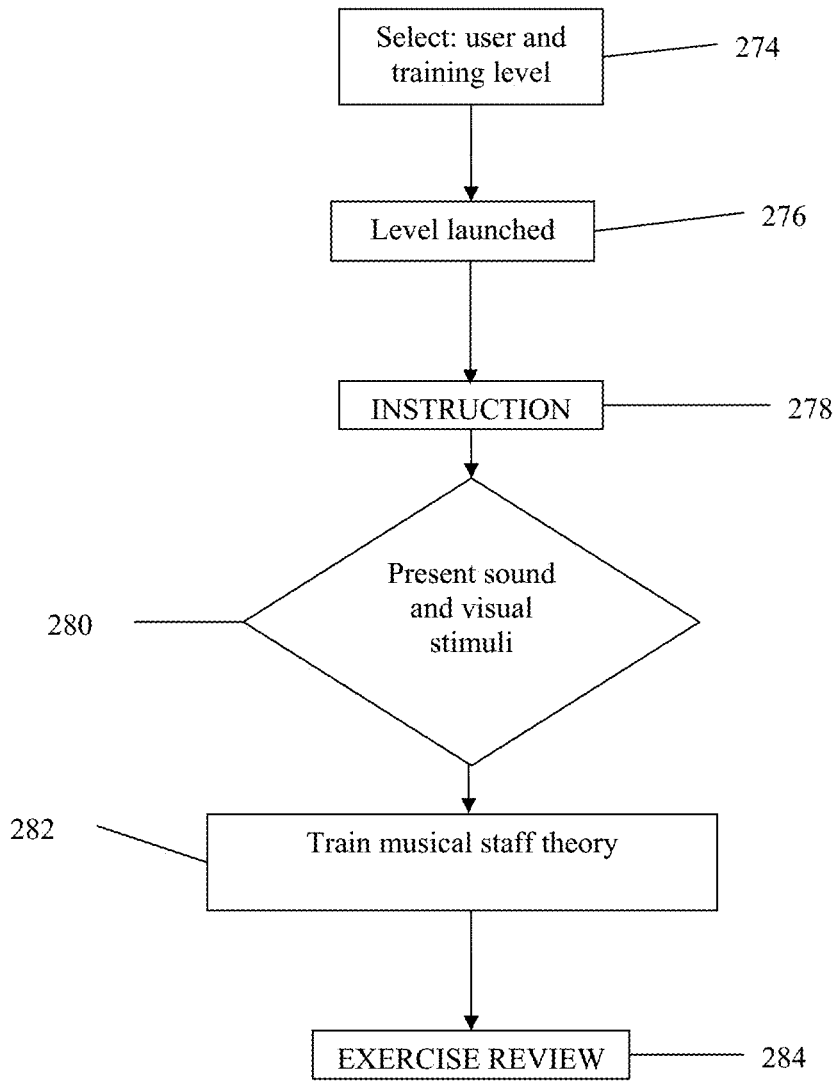
FIG. 19 is a flow chart showing the provision of training according to a Theory Exercise category.

An example method of providing a TE exercise is shown in FIG. 19. The user or the curriculum mode may select training level 274 appropriate to the user. The training is launched 276 so that it is appropriate to the user and may provide instructions 278 to the user. Selected music stimuli and/or animal characters 280 are presented to the user in the course of the exercise. The user may match, discriminate, recognize, and manage the auditory and visual stimuli in the context of a musical staff paradigm 282. Exercise review 284, may terminate the exercise with a set of questions that are posed to the user.

Theory exercises are exercises which train the relationship of exercise stimuli to musical concepts, such as the relationship between a musical staff and the notes that may be placed upon it. The exercise not only reinforces the audiovisual pairings taught in other training components, but also introduces various musical concepts and paradigms. One such concept is that when notes are placed at different locations along a musical staff that these have different sounds. This type of abstract/symbolic representation, although taught in relation to music, is similar to representations found with letters, language, reading, numbers, and math. Accordingly, one advantage of TE exercise skills is that these can generalize to other types of cognitive processes and skills. Theory exercises are listed in the table of FIG. 10, in the column labeled "Theory" as part of a curriculum. The following provides example embodiments of some of those exercises, as well as alternative embodiments:

TE1: In this exercise there are a series of notes on a musical staff. Each note is in a different color that corresponds to an animal character, such as a blue note which corresponds to the monkey "ME" who wears a blue outfit. An animal appears and makes their sound and the user must select the note that corresponds with the animal from the notes on the staff. Since animal sounds correspond to a musical scale, this exercise reinforces knowledge about what sounds are in what part of the musical scale/staff. This is intended to train the grapheme-phoneme conversion processing used in reading skills by associating an image with a specific sound. From a cognitive standpoint it is assumed that learning about this type of symbolic representation of sound will reinforce skills related to reasoning and language (which is also a symbolic representation of sound). Rather than using full notes on the staff, in one embodiment, half or quarter notes may be used, and a sound such as "La" may be presented for shorter durations, accordingly.

Figure 38A:
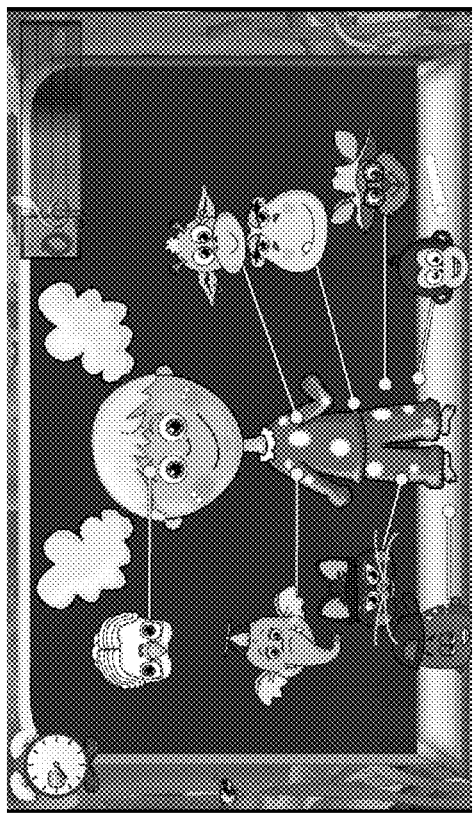

TE2: In this exercise there are a series questions about the correct location for different animals in relation to a human character's body part. For example, as shown in FIG. 38*a*, the owl is "mapped" to the character's head (and was associated with the top of the musical staff in the prior exercise). The turtle is associated with the character's feet (and was previously associated with the lowest note on the musical staff). Accordingly, this exercise provides an anatomical pneumonic for remembering the positions of the animal characters on a musical staff. This reinforces a semantic relationship between sounds (higher to lowest) and the body (head to toe).

TE3: In this exercise, as shown in FIG. 38*b*, the user must determine if the animal character is located either upon the lines of the musical staff or within the spaces between the lines of the musical staff.

TE4: In this exercise, the user is instructed to set each animal character on the correct place on the musical staff. This exercise reinforces the material learned in TCE1 to TCE3.

Figure 38C:
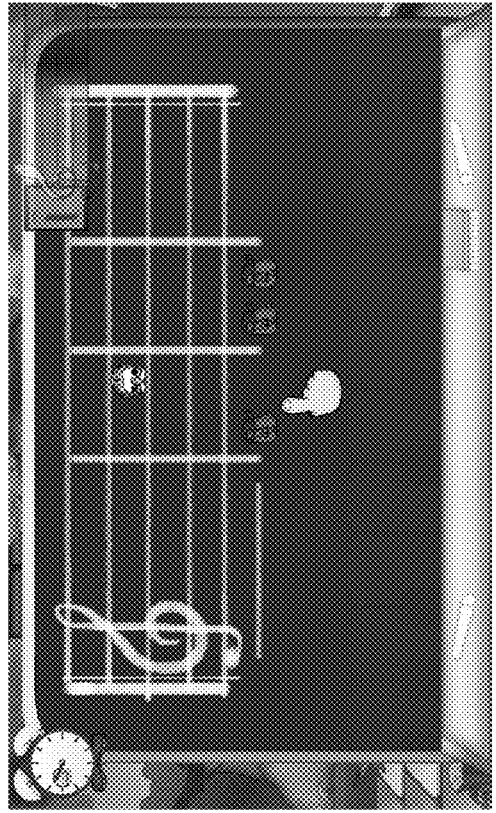

TE5: In this exercise, the user hears a simple musical note progression and then must choose which of two candidate sets of animals, arranged on a musical staff, represents what they just heard. As shown in FIG. 38*c*, in this example there is a single TEA note in one candidate set and two TEA notes in the other. When the user chooses correctly, the user may also then be instructed to try to sing the musical notes selected. In this exercise, the task stimuli allow simple music reading since the animal positions on the vertical lines of the staff are associated with the notes on the musical staff.

Accordingly, a cognitive training method is provided using a music-based game format by providing a set of musical theory exercises that requires a response from a user. The set of exercises can comprise both 1) a set of exercise that reinforce visual-auditory pairings, promote musical theory concepts, and explore relative relationships between stimuli (e.g. TE2), and 2) a set of exercises that explore the shapes and sounds explicitly within the context of a musical staff (e.g., TE3). In this example, the first set of exercises directly promotes associations between the stimuli (some notes are higher than others), and a second set of exercises contains primary goals emphasize the associations between the stimuli within a musical staff context.

Voice Awareness

The present invention may provide voice awareness skills 78 that provide training intended to warm the subject's voice, teach about vocal range, volume, scooping voice and vocal ornamentations using choral speaking, teach about vocal projection and vocal mime using simple auditory themes, simple movements and voice mime. The user may further be trained by the exercises to enhance, construct or express meaning utilizing their voice. Unlike singing lessons which may be used in music training, the voice awareness exercises include talking, repeating poems, rhyming, memorizing new vocabulary, educational concepts, talking with particular accents or voices of various characters, and other vocal activities. These exercises are more like warm, up exercises and are "gentler" than requiring a user to sing a whole song.

Figure 17:
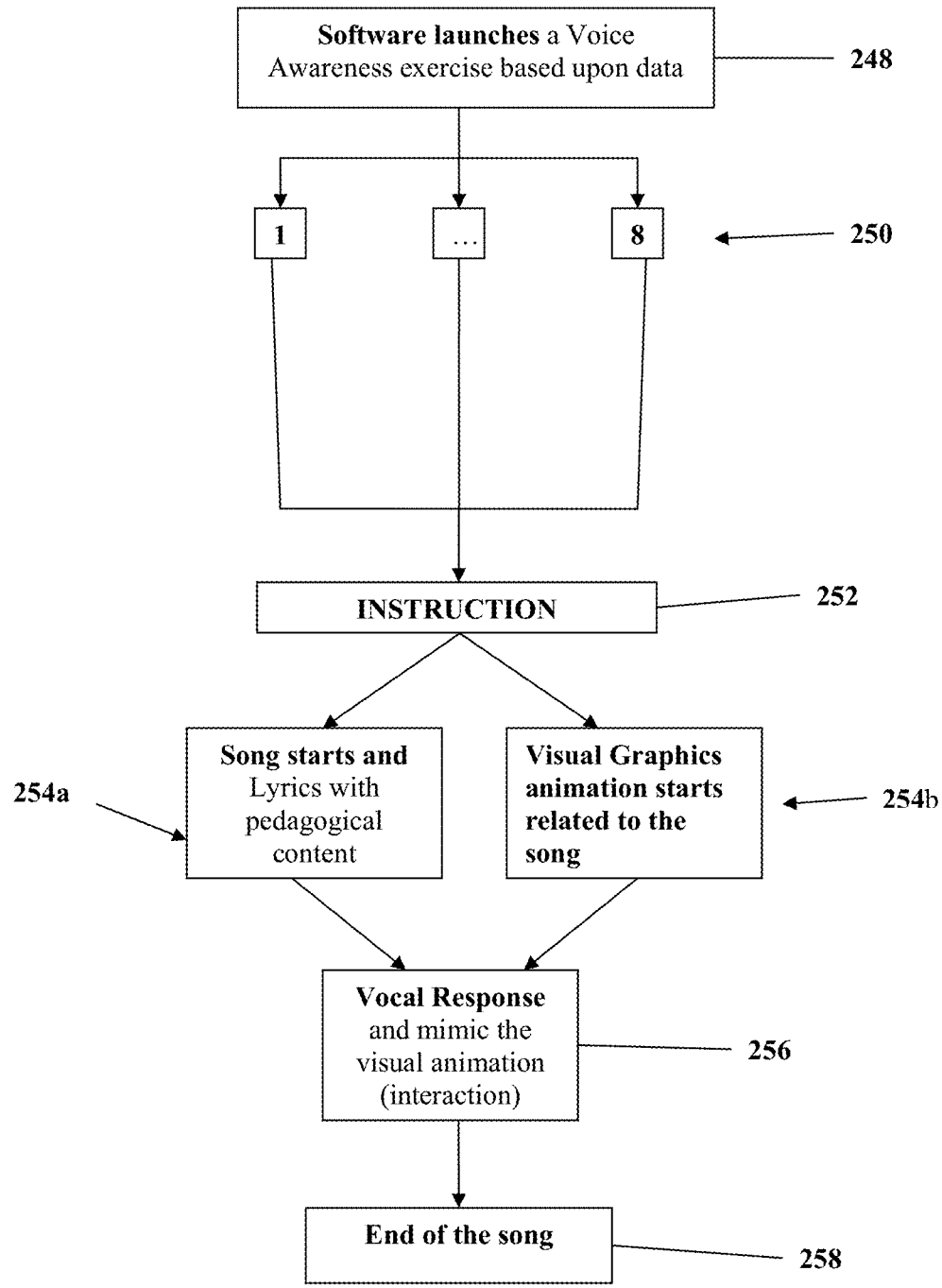
FIG. 17 is a flow chart showing the provision of training according to a Voice Awareness Exercise category.

An exemplary embodiment of the voice exercise is shown in FIG. 17. The user or the curriculum mode may initiate a song, poem or text which may be spoken or sung by a user during the VAE 248 based upon a user's prior performance or historical use of the training. The stimuli may be selected from between 1 and 8 sets of exercises 250 which correspond to training levels so that these are appropriate for a user. Instructions may then be provided 252 relating to what the user should do during the exercise. A story module may be presented to give an example of a principal of the exercise, in some cases. The exercise is then presented and may involve lines from a song (with lyrics and pedagogical content), poem or other content 254*a* and associated graphic animation 254*b* presented to a user. The user may vocally respond 256 along with the training and by doing this can "warm" the user's voice and allow exploration of vocal range in the course of the exercise. The VAE module 248 can also detect the user's participation and performance by use of a sound processing module including pitch recognition algorithms. The exercise may then finish 258, or an evaluation module may provide questions that review song content or other aspect of the song.

The voice awareness exercises are intended to cause the users to both speak, repeat words and song snippets, and sing short songs, in an interactive manner with the training. A simple exercise may train the vocal (motor) apparatus using a simple utterances or sounds (sounds made by the user may not have words and the user may be instructed to hum or emit other vocal response). While simple, the VAE can be difficult for a user with language or other impairment, unlike the musical production exercises which are often similar to performing karaoke, the voice awareness exercises generally require relatively less vocal response from users.

For example, the exercise may ask a user to make the sound associated with an animal such as a cow "Can you make the sound a cow makes?" The voice awareness exercises may also have users pretending to brush their teeth, jump around, and do other activities that encourage young users to participate. Although singing a 3-6 minute song may be overwhelming or unsuitable for some users, these users can also likely jump around while singing small parts of song and thereby participate successfully in the training. The intention of the voice awareness exercises is therefore to have users repeat sounds, songs, words or sentences in a manner that is simpler than singing entire songs. Often this occurs while the user concurrently does a physical activity, for example, in order to deter shyness when the training occurs in a group setting.

Voice Awareness exercises (VAE) are listed in the table of FIG. 10, in the column labeled "Voice Awareness" as part of a curriculum. The following provides example embodiments of some of those exercises, as well as alternative embodiments:

VAE1: In this exercise, the user watches a character get ready for school and is encouraged to mime various behaviors such as brushing teeth, tucking in a shirt, flossing, etc. The user may also be asked to repeat parts of a song that is presented.

VAE2: In this exercise, the user hears and repeats a poem about eating lunch.

VAE3: In this exercise, the user watches an animated rock band and is encouraged to sing along with parts of the song.

VAE4: In this exercise, the user is asked to make sounds like various animals that appear in the animated sequence.

VAE5: In this exercise, the user participates in a dance class by doing activities such as clicking their heels together, touching toes, bending etc.

VAE6: In this exercise, an elephant reads a poem and then the user is asked to repeat the poem, or parts of the poem, either along with the elephant during a second iteration, or by repeating segments of what the elephant says.

VAE7: In this exercise, the user repeats songs that have a high degree of rhyming.

VAE8: In this exercise, the user is asked to make sounds from nature such as the wind, a wood pecker, etc.

VAE9: In this exercise, the user is asked to make sounds that are associated with the animated animals that have previously been paired with particular sounds.

Musical Product.

Figure 20:
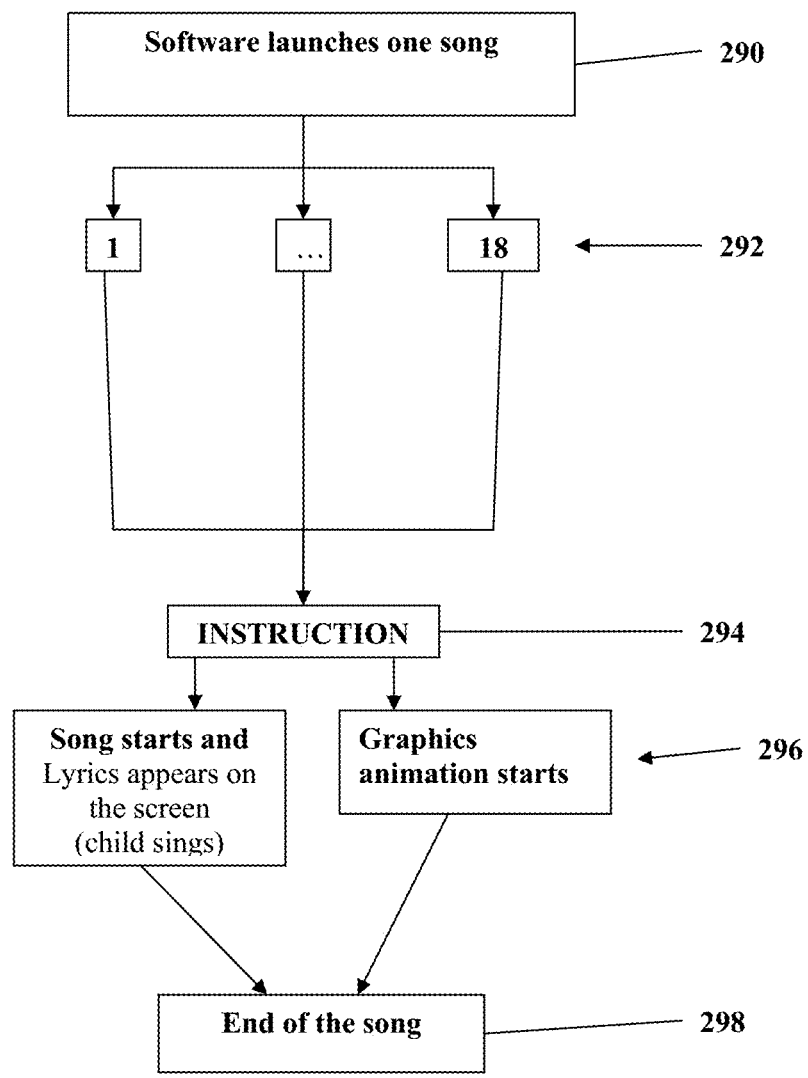
FIG. 20 is a flow chart showing the provision of training according to a Musical Product Exercise category.
Figure 21:
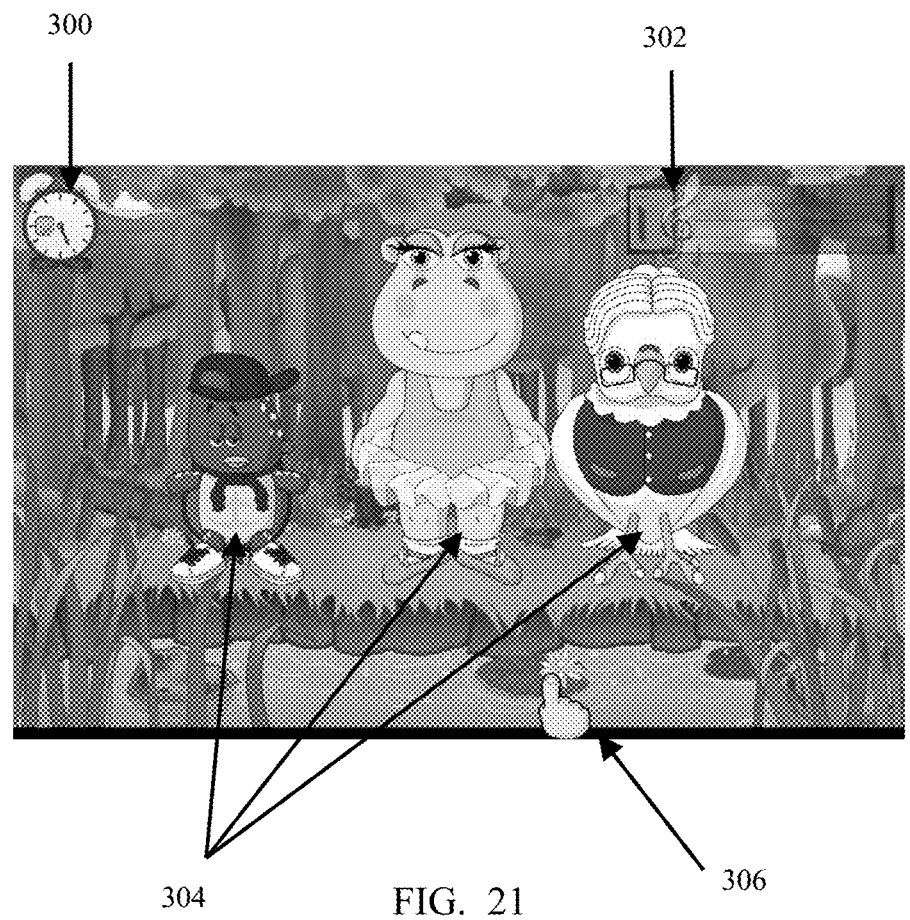
FIG. 21 is a pictorial representation of a game screen of the present invention, which shows a forest environment in which a user has to make a choice about either multiple animal sounds, multiple animal characters, or both.

An exemplary embodiment of the musical product (MPE) exercise 84 is shown in FIG. 20. MPE exercises are designed train a subject to sing correctly, to produce sound at the correct pitch, and to memorize simple (or difficult) meaningful lyrics. MPE exercises may further promote learning various musical and singing skills and concepts. Particular moves, such as body movements, may also be required as part of an MPE, so that a user learns to sing and move in accordance with the music. In one embodiment, the user is instructed to sing a song as part of an MPE. This may occur while a visual cue (e.g., a moving dot, the word being dynamically highlighted, etc) indicates the word that is to be sung (similar to what occurs in Karaoke). The MPE training may occur similar to the method shown in FIG. 17. The MP module 84 can also be designed to detect the user's participation and performance by use of a sound processing module including pitch recognition algorithms.

Examples of Music production exercises (MPE) are listed in the table of FIG. 10, in the column labeled "Music Production" as part of a curriculum. The following provides examples of topics, themes and embodiments of some of those exercises, as well as alternative embodiments. Several exercises have been selected from over 20-30 exercises which currently exist or which are in design phase in order to illustrate the features of the invention.

MPE1: this exercise is called "Who can that be ringing the doorbell?" This phrase is sung as different animal characters make appearances on the screen and hand is also shown pressing a doorbell. The ending of the song may be fixed and reveal which particular character was ringing the doorbell. Alternatively, the character can change or can change with different versions of the song. In this simple MPE the object is to encourage the user simply to sing the song.

MPE2: is an exercise called "Keep the Beat". The user is instructed by the song to "keep the beat with your hands" then to "keep the beat on your toes", then to "dance with the bop of the beat". The user may also be asked to hum to the beat. In addition to vocal response, users are instructed to use body parts to mimic the beat of the song, which is a type of rhythm exercise. This illustrates that the songs may relate to various musical concepts or skills. Instead of simply concentrating on following the beat correctly with movement, students may also concentrate on humming or singing the song. In this manner, MPE exercises may reinforce other exercise categories and concepts of the training.

MPE3: is an exercise called "I can count to 8". The user sings a song about counting to 8. This introduces a basic number concept in a fun manner. Other examples of numbers or math-themed songs may involve "getting 2 apples from one tree and 2 from another so that you end up with 4 apples". Further, additional portions of a song can be appended to earlier versions in order to increase difficulty level. To illustrate, a secondary portion may instruct a user to "count backward from 8", which is a very different skill than counting forwards. By introducing these concepts in a fun song, students are exposed to various concepts and ideas in a gentle manner. Simple math skills can be introduced within the MPE exercises. In an evaluation module that follows the exercise, a user may be quizzed about a concept such as "what number comes after 5?" A user's response may be evaluated and appropriate feedback provided.

MPE4: Is an exercise called "Scrub scrub scrub". In the exercise, a song informs the user that "It is time to get clean in the tub". Some of the MPE exercises may not be related to developing music, cognitive, or other skills, yet may also serve to be more than simply entertaining. In this case, habits and skills related to topics such as brushing teeth, making the bed, looking both ways before crossing the street, taking baths, and hygiene may be presented to students in order to reinforce good habits in their lives. Further, from a cognitive training perspective, basing songs on everyday chores that the users are familiar with may cause users to be more engaged by, and allocated more attention to, the MPE tasks.

MPE5: Is an exercise called "Running Rodents". In this exercise, a song narrates how some "running rodents" are trying to get cheese. In this exercise, there are many rhymes.

It is obvious that many additional musical product exercises may be provided by the training in order to training a user to sing and to teach students new information in an interesting and efficient manner. Although song lyrics are often very memorable, songs are not normally used to introduce information or concepts in a classroom setting, and this is an advantage of the invention. In order to teach or reinforce language skills and fluency, songs may be presented in different languages, or may have portions of the songs or words which are sung in different languages. For example, a song may be sung about "days of the week" and portions of the song are sung in English and then repeated French.

Songs used in MPE exercises may also be used to introduce various topics such as sounds made by different animals or animated characters. The exercises may also have songs that introduce musical concepts such as a particular tone is higher or lower than a different tone. The difficulty of the songs may be increased by introducing harder rhythms, melodies, or the conceptual, perceptual, or vocabulary level difficulty related to the lyrics of the music. By training song lyrics which use vocabulary from an earlier grade level to a later grade level (such as from a first grade level to a third grade level) as training progresses, difficulty may be adjusted. Alternatively, increasing the average number of syllables per word may be done. Further, more complex ideas and concepts may also be used as training progresses. Difficulty may be increased by adding new songs or by appending additional verses.

User performance evaluation may include presenting questions in the songs, or after the songs. Unlike karaoke the song can be paused while the user is presented with a question. In this case a tune, such as the melody of the song, may continue while the user is asked to answer a question, such as by making a selection on a display. An auditory question may be asked after the song "I can count backwards from 8" which asks, "What number comes before 5?". The choices on the screen can be "4" and "6", and the user must select the appropriate answer by touching the correct response on the display.

Creative Exercises.

Figure 36B:
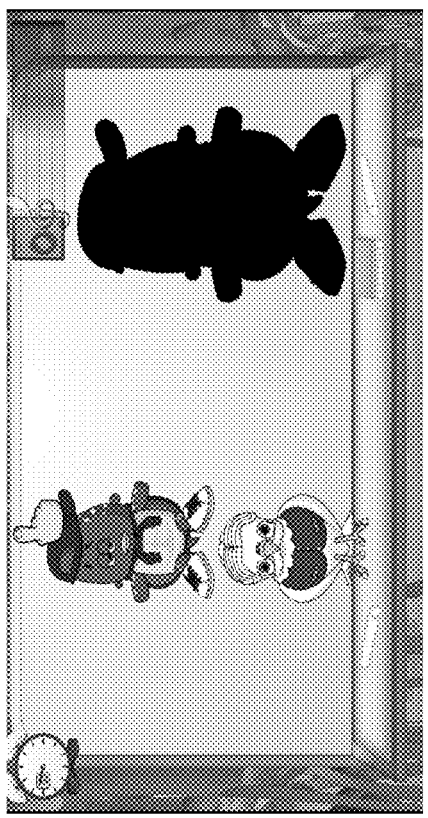
FIGS. 36a-d show 4 pictorial representations of exemplary game screens of the training.
Figure 36D:
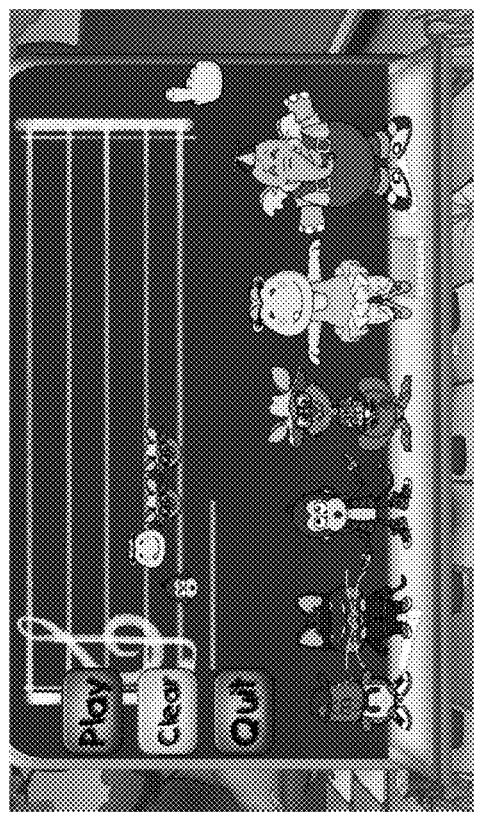
Figure 36A:
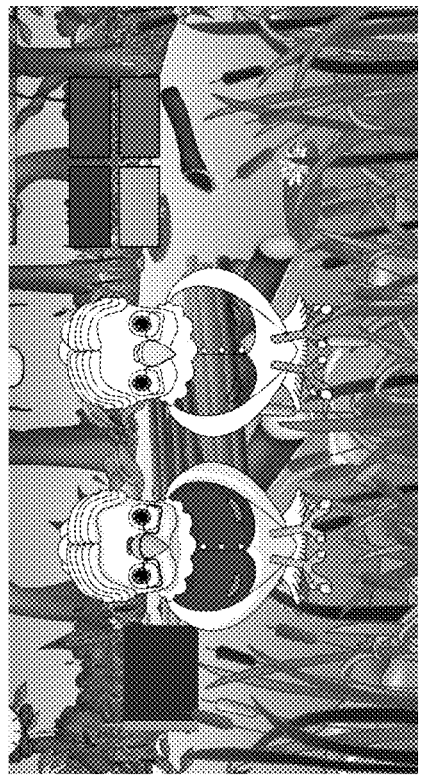

An exemplary embodiment of the creativity exercise (CE) 86 is shown in FIG. 19, where the CE is CE8, in which the user is trained (again) on a musical staff task. The CE training category has an assortment of various exercise types. Some of the CE tasks may be similar to those of the other exercise categories, such as a task related to rhythm of musical staff theory, but the CE tasks are generally more playful, less structured, and allow for the user to be more creative. The CE tasks may also involve various types of artistic goals such as drawing one of the animal characters. The CE tasks may train a user to develop fine motor skills related to writing (e.g., movement of hands and fingers), to recognize the position of tones and their relations on the staff, to perform grapheme-tone conversion, to practice writing skills, to associate various images with different styles of music, to develop spatial skills, and to associate musical content with particular colors and geometrical forms. Creativity exercises may serve simply to be entertaining to a user rather than each being designed to provide training. This is because it is important to allow users to rest so that the training remains fun and entertaining. Creativity exercises are listed in the table of FIG. 10, in the column labeled "Creativity" as part of a curriculum. The following provides example embodiments of some of those exercises, as well as alternative embodiments:

CE1: is an exercise called "Color the animal", an example of which is shown in FIG. 36a. In this exercise the user drags colors from a color palette to regions on an animal. In one embodiment the animal is shown fully colored on the left side of the screen (visual cue) and the animal's silhouette (visual probe) is shown on the right side of the screen. The user drags the colors onto the silhouette until the two animal characters match in color (template matching). In another embodiment, the animal is shown fully colored (visual cue) and then this disappears, or reappears intermittently. The user must remember the colors that go in particular regions to correctly color the silhouette (template matching with delay). The background may be animated which exercises both memory and focus/concentration (template matching with delay and distraction stimuli). Difficulty can be increased by increasing the number of colors used, the delay between cue and probe presentation, the number or type of details of the object which is colored, or by decreasing the difference between the candidate colors, the interval during which the template is shown. Background music may accompany the exercise to make it more entertaining.

CE2: is an exercise called "Draw the animal". In this exercise the user is asked "Do you think you can draw this animal? Try to draw the animal". The user can draw the animal on paper, or if available the user can draw the animal using a tablet or touch sensitive drawing screen. The drawing may or may not be evaluated. This allows practice of fine motor skills and creativity, as well as giving the user a freeform task. Many other embodiments of drawing, copying, and coloring tasks can serve as CE2 tasks.

CE3: is an exercise called "Animal shapes" as shown in FIG. 36b. The task includes a visual cue (a silhouette) of an animal on the right hand side of the page. The user is instructed to click on the correct animal from two or more candidate probes, to correctly match the cue. This task requires spatial comparison of shapes in order to produce a correct match.

In a further example exercise, the user may be asked to find the animal in a complicated background which is related to a particular sound "Can you find the animal that makes the following sound?" There are 8 animals hidden in a picture and as each sound is played the user has to click on the animal associated with it.

CE4: Is an exercise called "Animal Sounds", in which the user clicks on the animal that matches the sound presented to the user (such as a roaring lion). The animals and sounds may include those used in other exercise categories, or many other animals and sounds as well simply to be more fun and entertaining for the user.

Figure 36C:

CE6: Is an exercise in which users click-and-drag puzzle pieces to correct regions of an animal, an example of which is shown in FIG. 36c. This exercise is a virtual jigsaw puzzle. Harder difficulty levels can increase the number and complexity of the puzzle pieces, or the complexity of the puzzle being assembled. Unlike conventional jigsaw puzzles the student can be shown what the filled in puzzle looks like either before the exercise starts, or intermittently, or by pressing a button that says "hint".

CE7: In this exercise, notes slide across the screen on a background that includes a musical staff, while a song corresponding to the notes is played. Students can chose colors for the notes from a group of colored boxes. In alternative version of this exercise, some of the notes are already colored and the student has to select the same color from a group of colored boxes. In another version of the task pictures of the animals slide across the screen on different lines of the staff and the boxes have pictures of the animals, if the user selects the box of the animal character that is going across the screen the animal will make its noise and then disappear. There are many other variations on this type of exercise but it basically may be used to teach the user about the spatial relationship between notes on a musical staff and the respective sounds.

CE8: In this exercise there is a musical staff in the upper part of the screen and animal characters on the lower part of the screen, an example of which is shown in FIG. 36d. The user may create a song by clicking on the animals. Each time a user clicks on the animal, it appears as a corresponding note on the musical staff. When staff is fully filled the tune corresponding to the notes on the staff is played.

Training of Pitch, Melody, and Rhythm.

Auditory processing skills related to detection and discrimination are essential in development of language. The training both develops and evaluates the auditory processing abilities of the user. One fundamental aspect of auditory training includes training components having pitch training. Since pitch is one of the simplest characteristics of music, the training focuses on this topic to provide users with exercises and concepts that are likely to be successfully understood. Pitch recognition is necessary for tone recognition and discrimination. Regardless of exercise category, pitch plays a central role in the learning process related to the training. Pitch detection and discrimination is a key reference linking the animal characters to sounds. These skills are a driving force in a young user's hearing development. Pitch skills are also relied upon in the Musical Product exercises, where users must focuses on applying the mastered elements of rhythm and melody which are often included during the prior exercises of a lesson. The pitch skills and characteristics which are relied upon during the training should be selected to suit the vocal range and ability of an average user in a target age group. Since pitch is easier than working with rhythm and melody, pitch can be emphasized in the training so that the training is easier for young users.

The training can also include the detection and discrimination of Melody. In addition to being central to the Musical Product exercise category, melody is important in forming musical phrasing. Fairly repetitive melodies allow easier memorization. In Voice Awareness Exercises the use of melody compliments the character's movements. Melody can be used to facilitate practicing of the musical scale, to add fun to vocal range exercises, and to help with memorization of training stimuli.

The training also includes the detection and discrimination of rhythm. Users learn to recognize and follow rhythms, sometimes by observing and repeating the animated character's movements so that the training occurs almost effortlessly. The first rhythm exercise RE1, allows a user to become comfortable with simple rhythms. Later exercises such as RE2 familiarize the user with recognizing tempo differences and discriminating between various tempos occurs in exercises such as RE4 and RE5. In the training components related to rhythm and motor skills the training modules may contain rhythm evaluation and recognition algorithms that track and evaluate the performance of the user. This may be done, in part, using a video camera with a motion capture module. All of these skills are then harnessed in the practical application of creating the rhythms as occurs in "Rhythm Building" exercises in which users can create and compose their own rhythm.

Game Screen Backgrounds.

One embodiment the present invention training may be realized as a video-game. The game may include multiple game screen, for example, such as the game screen shown in FIG. 21. Common elements for exercises may appear on a game screen. A clock 300 may measure the cumulative time spent for a given exercise. A point scale 302 may reflect a user's performance. A pointer 306 may enable the user to navigate and select items on the game screen such as animal character buttons 304 that allow a user select an animal as part of providing a response during a task.

Figure 22:
FIG. 22 is a pictorial representation of a game screen of the current invention, which shows a pyramid background that is associated with a particular level of difficulty in the training.

Game screens may have backgrounds reflecting certain environment themes. An example is shown in FIG. 22 which shows a pyramid temple 312. Environments that may be shown along the progress tracker path in FIG. 25 include: the forest 310; the temple 312; and, the jungle 314. Each environment may correspond to a level of difficulty. For example, in FIG. 22, the easiest level may correspond to the pond environment.

User Navigation.

Figure 23:
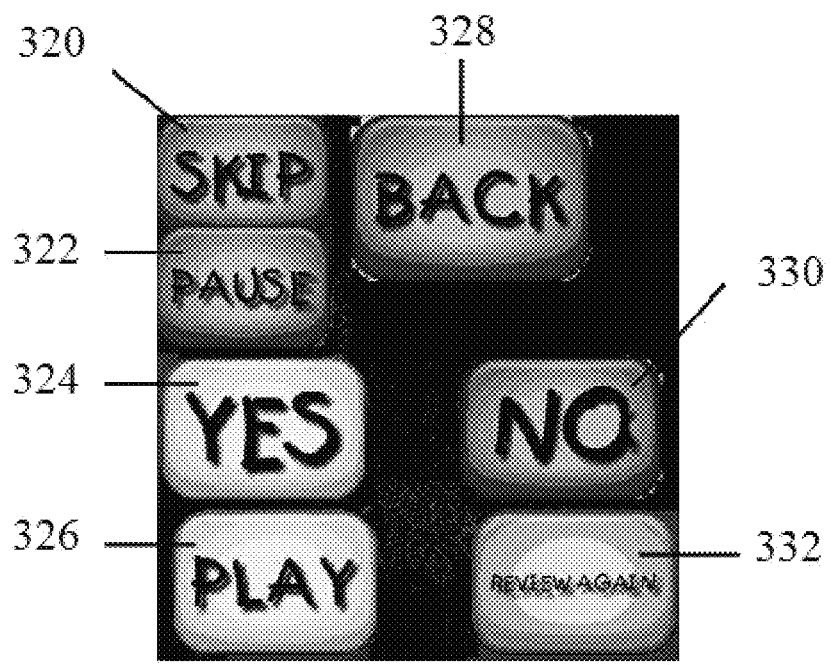
FIG. 23 is a pictorial representation of an example controller module which helps users to navigate within the training environment and access different parts of the training.

A user may interact with the Training Manager Module 574, in order to adjust and control the training in permitted manners. An example of a possible interface that may be used in an embodiment of the invention is shown at FIG. 23, which may be operated by the user interface module 550 to assist a user to navigate using a menu to select and interact with any exercises, games, or other elements of the present invention. The interface may offer multiple additional functions and options, for example, such as options to: repeat the instructions, pause, switch exercises, or return to a general menu of additional options. The interface may display several buttons, for example: a SKIP button 320 may be operable to cause the present invention to skip the screen and move to the next scene; a PAUSE button 322; a YES button 324; a PLAY button 326 which may initiate an exercise or may "restart" a paused screen; a BACK button 328; a NO button 330; and a REVIEW button 332 which may cause the training to provide a review or example for the user.

Feedback

Feedback provided by the training can be positive, neutral, or negative. Feedback may not be given for some exercises. An example, of positive feedback is "Great Job", and example of neutral feedback is "Almost", or more preferably "Good try", while an example of negative feedback would be "That was not correct", "Very close, try again" or "that was not correct, let's try again".

After feedback is provided, the next exercise task may be presented or the current task may be presented again. Task repetition may occur immediately or may occur after 1 or 2 other exercise tasks have occurred. Task repetition may be contingent upon at least one of 1) whether the response was correct or incorrect 2) the feedback type. In the case of Negative or Neutral feedback the user may subsequently be asked to try again or may not be asked to re-try. In one embodiment, when neutral or negative feedback is provided, preferably the user may be allowed to try again up to N times, where N is usually set to 2 or 3. Allowing more than 3 tries would normally be avoided since this might lead to increased frustration for a user. More typically, when a user answers incorrectly, the training simply moves on within providing task repetition or additional chances at providing the correct answer for a task.

In one preferred embodiment of the training the feedback is either positive or neutral, but not negative. Telling a young user that he or she did not get something correct may be demotivating, especially early on in the training.

Feedback can be provided for a single response, choice, or selection of a user. Feedback may also be provided in relation to the user's performance across various exercises, tasks, or other training components.

In a preferred embodiment, the user's response is not related to playing a musical instrument and rather reflects a decision, choice, or answer which is made to respond to a question.

Figure 25:
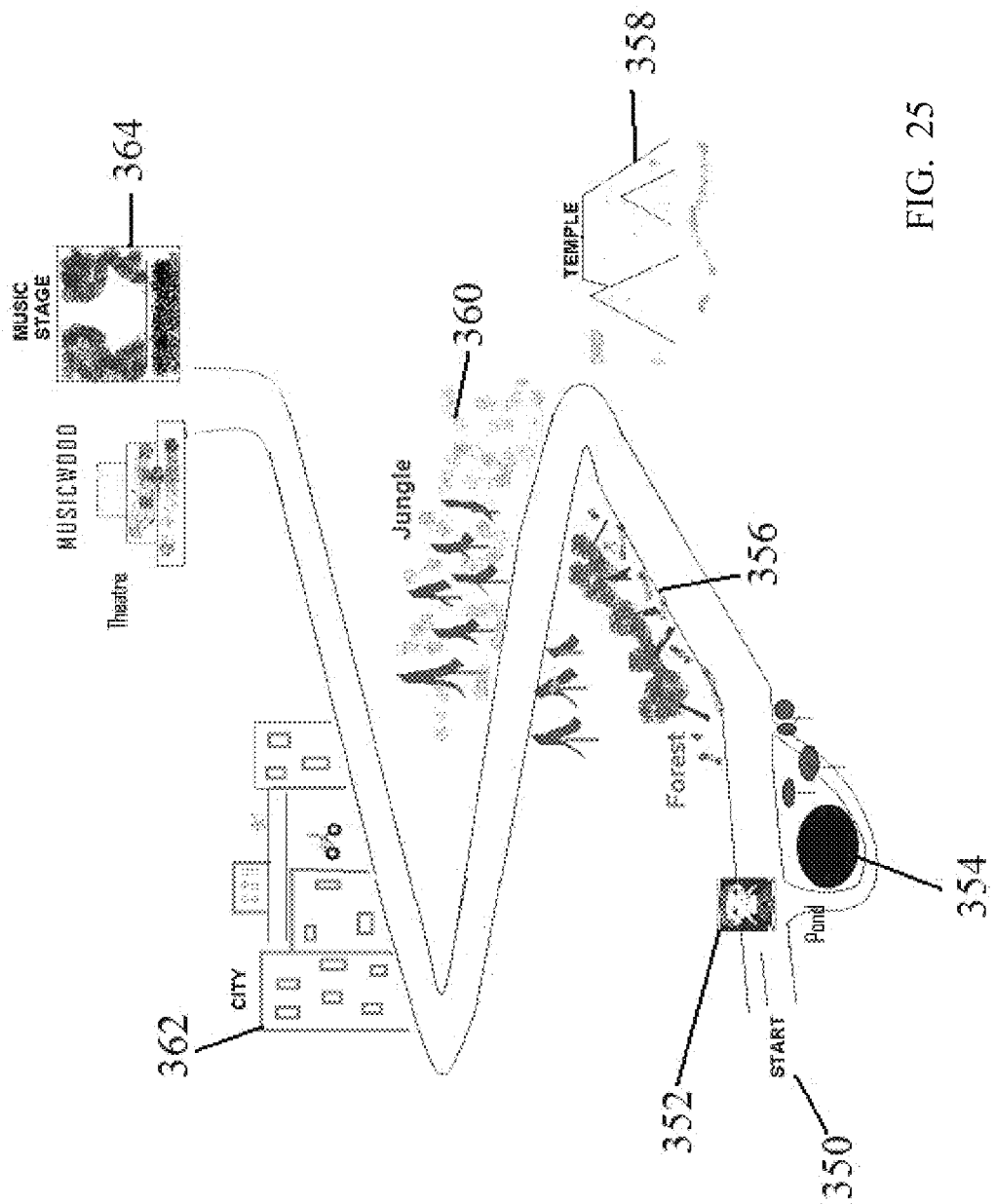
FIG. 25 is a graphical representation of an interactive map of the training platform in which the user's current position is shown to reflect a user's progress.

Feedback may be given regarding a user's progression through the training which is supplied in the form of an interactive map, as shown in FIG. 25. The interactive map may indicate progress by utilizing a pictorial scale. The user may be represented by the image of a little boy or girl avatar 352. The image of the boy or the girl, representing the user, may initially be positioned at the bottom of the map 350, and may progress to different levels according to completion of portions of the curriculum. The interactive map may also be used in the "free exercise choice" mode to allow a user to select training components. In other words, a user can move the avatar to a selected location in order to be presented with training components associated with that part of the training. The user has reached the last level of the training when the image of the boy or girl avatar reaches the theatre stage 364. In this example, the order of levels in as follows: The Pond 354; The Forest 356; The Temple 358; The Jungle 360; The City 362; and the Theatre Stage 364, which is the hardest level. In one embodiment thirty difficulty levels may be represented between The Pond 354 level and the Theatre Stage 364 level.

Feedback regarding a user's progression through training may also be provided as oral feedback or may be provided in a report 118 or by in any other means to a user. A simplified report and associated metrics can be provided to the typical end-user while much more detailed metrics and data may be stored and reported for clinicians and for ongoing research and product development purposes.

Rewards

Figure 26:
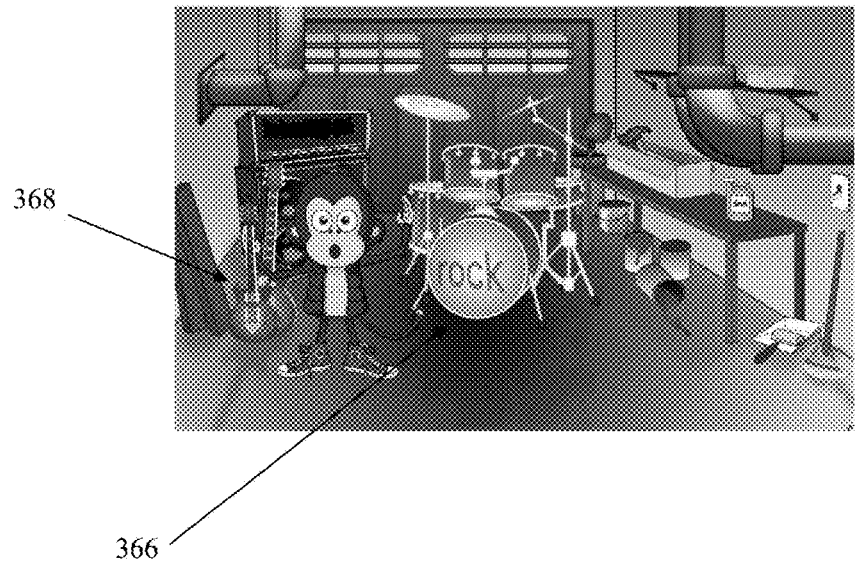
FIG. 26 is a pictorial representation of a game screen which is part of an exercise in which a user is asked to sing along or repeat the song with a rock band and also serves as a screen in which the user is presented with a prize token which in this case is a guitar.

Another type of feedback is a reward which may be implemented as various classes of awards. Progress can be rewarded with a virtual "prize". A reward module 600 may provide prizes to the user throughout the training exercises using animated virtual prize tokens. As shown in FIG. 26, a token is displayed in the center of the screen 366, which in this case is the animated delivery of a "guitar prize" 368. Other forms of prizes and types of rewards may be provided by a reward module. For example, the user may be allowed to listen to a particular story that they like if they win a reward.

Figure 27:
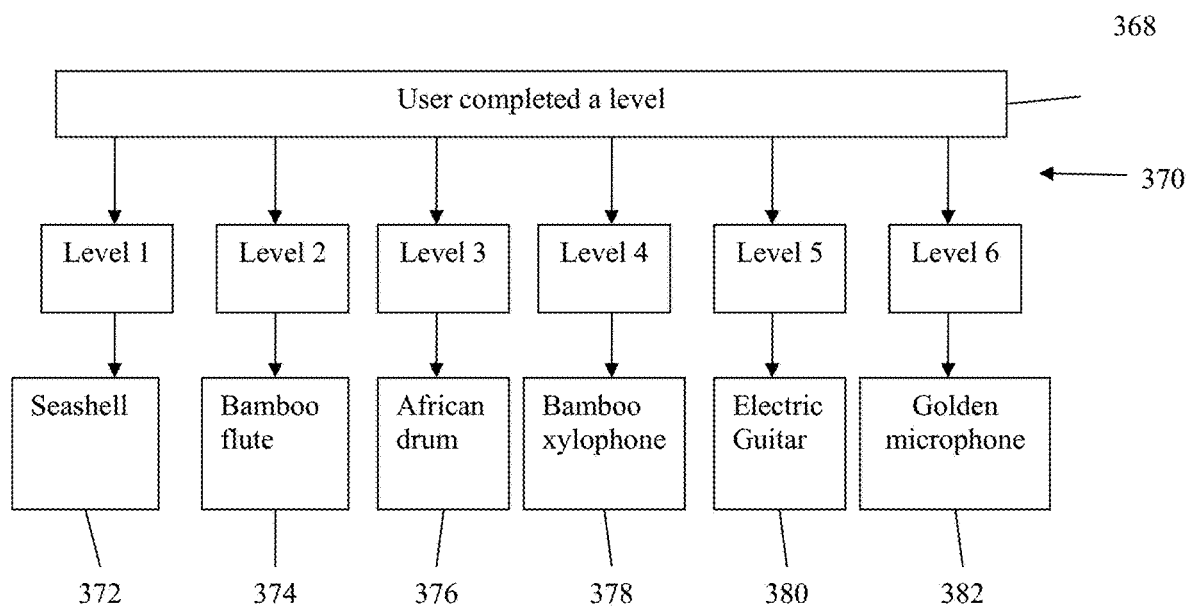
FIG. 27 a flow chart showing the prizes that are given to users as they complete each of a number of different difficulty levels of training.

Rewards can occur either in a fixed manner or can be dependently upon the user's performance, or both. Rewarding may be adjusted to the performance each individual user. For example, a user showing relatively slower progress may receive a prize 368 for reaching a less difficult goal such as the completion of a training level, as shown in FIG. 27. In this example, when the user completes Level 1 370, also known as "The Pond level", a seashell prize 372 is presented to the user by one of the animal characters in an animated video. When the training only includes 6 difficulty levels, then prizes 2-6 374-382 are provided to the user upon meeting training goals.

The reward module 600 may operate with the progress tracking module 592 to deliver rewards according to user progress. The data collected during sessions of the present invention may define the performance goals applicable to each user. Through the information collected by the tracking progress module, the present invention may deliver prizes after each goal reached and/or after each level completed by the user. Performance goals may be met independently from performance rates. Performance goals may be disassociated from performance rates that may be required for a user to increase a level of difficulty. The performance goals may be set at training milestones that may be reached by a user after an amount of effort deemed to be challenging to a particular user and in accordance with the characteristics of the user.

At the end each lesson a student can win a reward class which is a "badge" award, while at the end of each difficulty level a student may be rewarded by an "instrument" class of award. The training may provide a game-screen that is presented to a user intermittently which displays the badge and instrument awards that the student has won. At particular lessons, there are animations that show a user's progress within the overall training or the training for that particular day. This feedback enables a user to gauge their current progress and also understand how much more training will be required. Prizes may also be given when a user finishes particular lessons or at the end of each lesson. Prizes may also be given contingently, based upon user performance.

In one embodiment of the present invention there may be three scenarios for prize delivery implemented by the reward module 600: (1) Performance level is under, for example, 60% after the first three sessions; (2) Performance level is between, for example, 60 and 80% during the first training session; and (3) Performance level is, for example, over 80% during the first session. For case (1), the user will always receive a prize after each exercise for lesson 3 to 6 and will receive prizes depending on performance after lesson 6. Performance should typically be over 65%, and so in this case prizes are given as rewards for simply doing the task, which is likely proving difficult to a user. Additionally, if a user's performance is significantly less than 65%, then certain exercises which the user does the most badly on may be skipped, or substituted with an another version of the exercise (which may be easier or just different in terms of its content), in other levels to keep the user from getting too frustrated.

For case (2), the user will always receive a prize after each session which includes each of lessons 1 to 6, and will then receive prizes contingent upon performance after lesson 6: Performance of each subsequent session should be over 65% for a normally developed child.

For case (3), the user will receive prizes after the completion of each level as long as performance remains over 75%.

Other reward contingencies and schedules are possible and prize delivery may occur at different points of the training in alternative embodiments of the present invention. The prize delivery operations may be adjusted according to parameter of the reward module 600, and reward protocols may be adjusted in accordance with the characteristics of the user or based upon user performance.

Scientific Study Results

Figure 29:
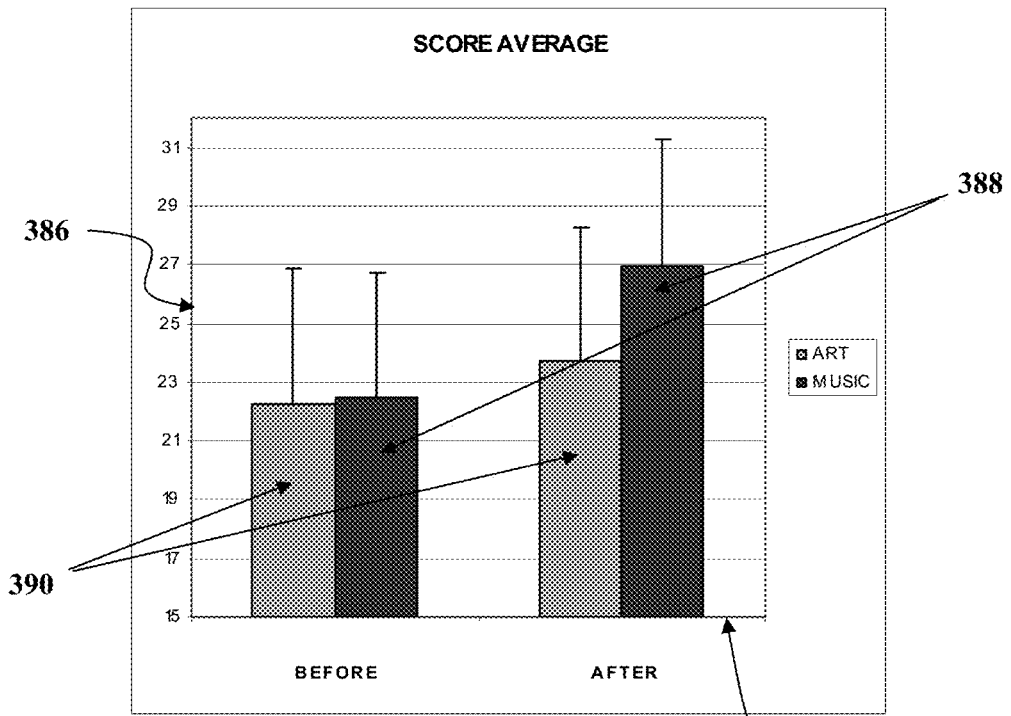
FIG. 29 is a graphical representation of study results related to the present invention, showing the verbal intelligence score of subjects exposed to a method of the present invention and subjects of the control group, both before and after training.

The present invention may be utilized to generate study results. The study results may reflect data related to one or more users of the training. Study results can contain summary statistics such as the minimum, maximum, and average time required for a user of a particular age to complete an exercise of a particular lesson or session. Study results can also include data related to other testing of a user carried out before and after the training in order to show the effect of training. The training has been scientifically validated by such study results to show benefits compared to other types of training. For example, verbal intelligence score of a training group of users and a control group of users, both before and after training by the current invention is shown in FIG. 29. The abscissa axis is labeled to show data from before and after the training 384 and the ordinate axis shows the average score in verbal intelligence 386. Music training is represented by two bars 388 and art training (which served as the control training activity) is represented by two bars 390. FIG. 29 shows significant improvements in verbal intelligence for the training group 388.

Figure 30:
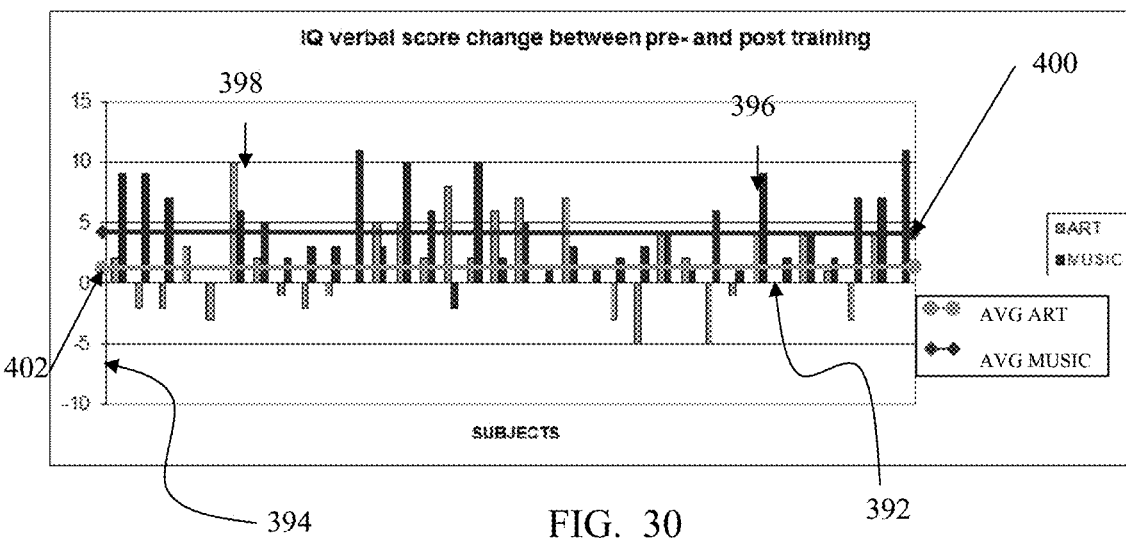
FIG. 30 is a graphical representation of study results related to the present invention showing the change in verbal intelligence score (training-baseline) for each individual who undertook the training of the present invention and the control group training.

FIG. 30 plots study results of the change in verbal intelligence score, computed as the score after training minus the score before training 394, where a positive value shows a benefit of training. Each individual subject is plotted along the abscissa 392 for the group undertaking the method of the present invention 396 involving music training, and the control group 398 involved in art training. Line 400 represents the average verbal intelligence score change for the Training group and line 402 represents the average verbal intelligence score change for the Control group. The strength of the beneficial effect, and its consistency are striking: over 90% of the children involved in the training method of the present invention improved their verbal intelligence score The benefit due to art training as smaller and not as consistent across individuals.

FIG. 31 shows a plot of study results representing a score for a rhyming task in ordinate axis 406 and before and after training sessions in abscissa 404 for the method of the present invention 408 involving music training and the control group 410 involving art training. This graphic is showing the significant improvements in rhyming score for the training group of the present invention 408.

Figure 32:
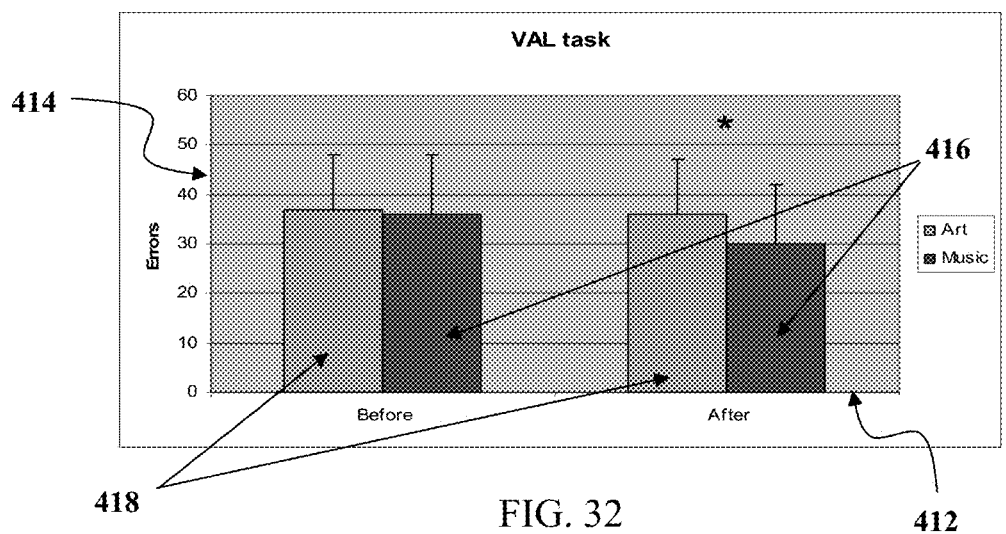
FIG. 32 is a graphical representation of the study results of the present invention showing the Visual Auditory learning score, before and after training, of subjects trained using the method of the present invention versus the control group.

FIG. 32 shows a plot of study results representing a Visual Auditory Learning score in ordinate axis 414 and before and after training sessions in abscissa 412 for the method of the present invention 416 involving music training and the control group 418 involving art training. The results show the significant decrease in Visual Auditory Learning score for the training group of the present invention 416 who achieved a higher performance.

Figure 33:
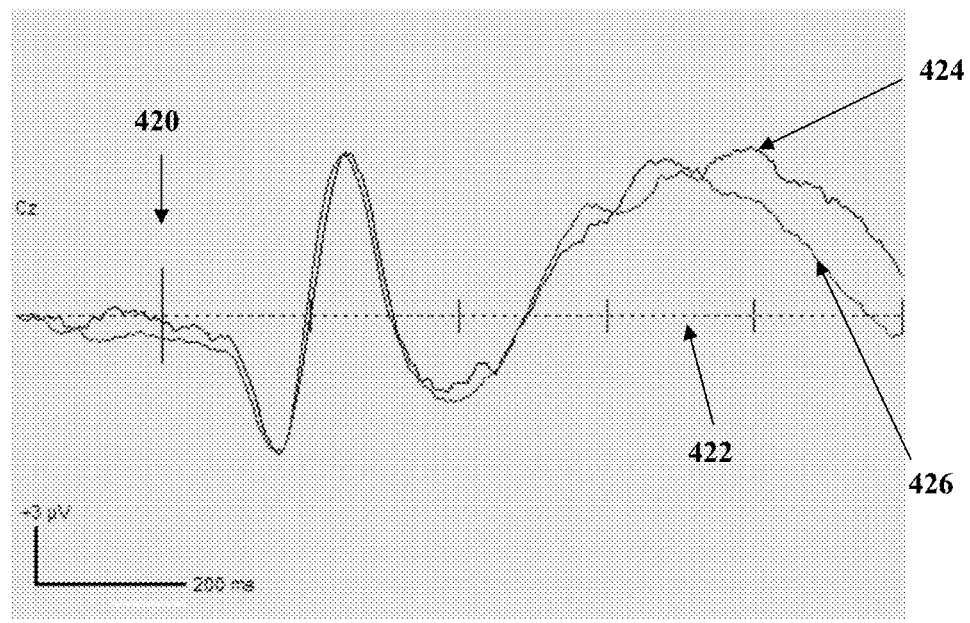
FIG. 33 is a graphical representation of Grand Average event related brain potential to an attention task, representing group mean ERPs elicited by Go stimuli in a Go/Nogo task at Cz site, both before and after training.
Figure 34:
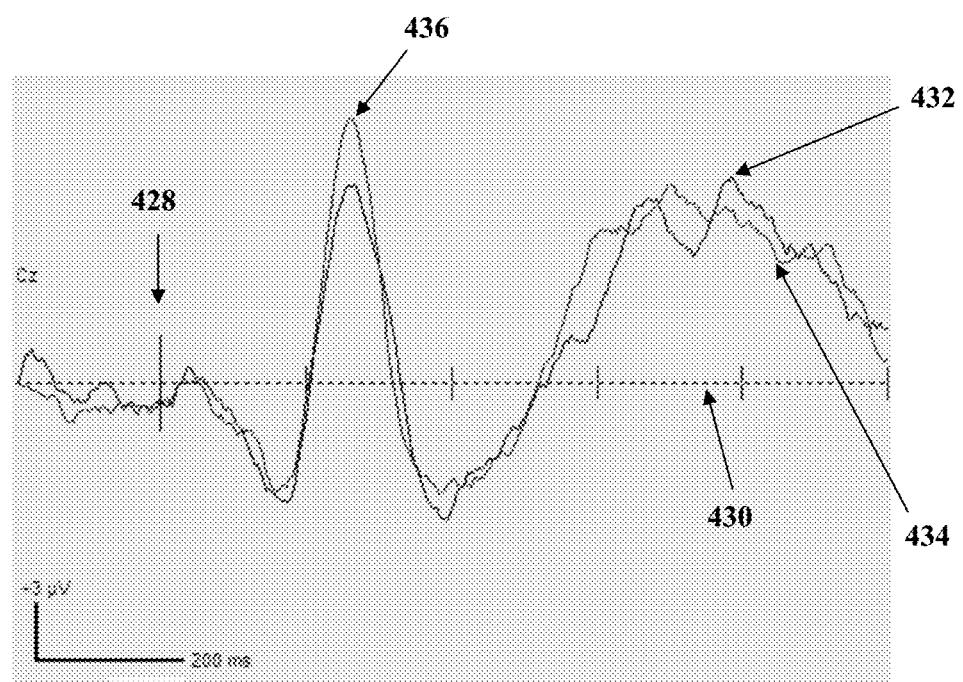
FIG. 34 is a graphical representation Grand Average event related brain potential to an attention task, representing group mean ERPs elicited by Nogo stimuli in a Go/Nogo task at Cz site, both before and after training.

FIG. 33 shows a plot of event related brain potential (ERP) average across all users of the present invention to an attention task. The group-mean ERP elicited by Go stimuli in a Go/Nogo task is shown at Cz scalp location. This electrical signature of brain function was recorded before 424 and after 426 training of users on the present invention. The ordinate axis represents microvolt amplitude of brain electrical signal 420 and the abscissa axis 422 represents the time course from −200 to 1000 milliseconds. The ERP 424 represents pre-test data and the ERP 426 post-test group mean data. FIG. 34 illustrates the brain responses related to No-Go stimuli, where the later components showed a clear difference before and after training on the P2 wave 436.

FIG. 34 shows a plot of grand average ERP for users of the present invention to an attention task. It represents the group means ERP elicited by Nogo stimuli in a Go/Nogo task at Cz site. This brain functioning data was recorded before 432 and after 434 training of users on the present invention. The ordinate axis represents microvolt amplitude of the brain signal 428 and the abscissa axis 430 represents the brain signal in time from −200 to 1000 milliseconds. ERP 432 represents pre-test data and ERP 434 is from the post-test data of the training group of the present invention. FIG. 34 illustrates the significant differences between before and after training recording in the brain responses related to Nogo stimuli such as the P2 component labeled 436.

The example benefits of the present invention reflected in the behavioural and brain changes of young children, and shown in FIGS. 29-34, may be better understood in the context description of the study from which these results were derived, which is included for the purposes of illustration and is not to be construed as limiting the invention in any manner.

Example Study

A scientific study conducted with a population of 71 children aged 4 to 6 years. The study has been published as "Short-term music training enhances verbal intelligence and executive function" by Moreno et al. (2011) in the journal Psychological Sciences. Accordingly the study will only be summarized here.

The training method of the current invention is based on the principle that transfer occurs when novel and trained tasks involving musical exercises involve overlapping processing components and engage a brain region shared with skills related to non-musical skills such as language and attention. Common neural processing and brain area activation suggest a mechanism for effective transfer from the skills trained by the training method to skills related to intelligence, attention, reading and language skills. Music and language share many cognitive processes and brain regions.

By using specific training exercises the brain areas involved in intelligence, attention, reading and language skills may be stimulated. For example, Rhythm training may activate the right hemisphere of the brain involved in pattern and temporal feature detection; Voice/Singing training can involve Heschl's gyrus and the left hemisphere of the brain, as well as the Brocas and Wernicke's areas; Verbal training with memory tasks can involve the planum temporale, pre-frontal and fronto-ventral areas; Training involving the theory category of exercises and involve the parietal and occipital cortex; the ear/discrimination training tasks can involve the auditory related brain areas and frontal and parietal cortices. The hypothesis of the study was that a short period of musical exercise based training would produce benefits in other skill sets related to language, attention, and intelligence and that these benefits could be measured using behavioral and brain imaging based methods.

Seventy-one children between the ages of 4 and 6 years old were recruited from various neighborhoods in the Greater Toronto Area. Data from 7 participants were discarded because they stopped the summer camp after 2 weeks, two children got sick, and two could not speak English fluently. The final sample comprised of 64 children (14 boys/18 girls in the control group and 12 boys/20 girls in the music group). The groups did no differ on age (p>0.8; 63.8 and 63.7 respectively) or mother's education (p>0.6; average education was a bachelors degree). The study received York University Research Ethics Committee approval and all parents signed informed consent. A background questionnaire was provided to every parent in order to screen out children who had had previous music or visual art training, as well as to match each group on level of mother's education.

During four weeks, children underwent the training realized in a computer game format and projected on the classroom wall. A group of students and their teacher participated in a 45 minute training session, which occurred twice each day. Teachers began the training session with a 45-min lesson, followed by a 1-hour break and a second 45-min lesson. The computerized experimental and control training programs were created by Dr. Sylvain Moreno. The computerization of training allowed the researches to control each lesson and to adapt the training progress to each class.

Both musical exercise and art exercise (which served as control) training programs shared the same learning goal, graphics and design, duration, number of breaks, and number of teacher staff. The only differing element was the content of the training. Each training lesson was conducted by 1 teacher, 3 teaching assistants and 1 research assistant. Training video games were directed by the teacher in a class format. The teacher had to follow the software curriculum in both training groups. The curriculum in music training had a combination of exercises shown in FIG. 10. The visual art training emphasized the development of visuo-spatial performance on several components such as light and color, line, perspective, material, and texture. The control training and the music video game were administered to children in separate rooms. Both types of training were described by teachers and parents as challenging, interesting, and rewarding experiences for the children.

Procedure

In the study, children were tested using a longitudinal design including a pre-test condition, followed by training, and then a post-test condition. The same battery of tests was used in before and after the training. The test battery was comprised of three components: 1) Intelligence testing achieved using Wechsler Preschool and Primary Scale of Intelligence (WIPPSI III, Weschsler, 2002) 2) Language testing using a Language test battery (Woodcock-Johnson III Battery, Woodcock et al., 2007) and an attention task (implemented as a Go-Nogo task) in which brain activity was also measured. The pre- and post-test stages involved the same tests. The separate components of the test battery were randomized for each child. The behavioral testing took place in laboratory facilities and lasted 30 minutes.

Children were pseudorandomly assigned to musical training or to visual art training (control group) to ensure that there were no prior-to-training differences between groups on the intelligence score and background questionnaire. All the children underwent both types of training for 20 days at the Royal Conservatory in Toronto. After training, the children returned to the laboratory facilities to again be assessed on a variety of cognitive measures.

WPPSI (Wechsler Preschool and Primary Scale of Intelligence) is an intelligence test designed for children ages 2 years 6 months to 7 years 3 months developed by David Wechsler. The current revision, WPPSI-III, is published by Harcourt Assessment. It provides subtest and composite scores that represent intellectual functioning in verbal and spatial domains. The short version of this measure was used, which comprised of two subtests: Vocabulary and Block Design.

The Vocabulary subtest contains 32 words arranged in order of increasing difficulty. The child is asked to orally explain orally the meaning of each word (for example, "What is a _____?" or "What does mean _____?"). The subtest is discontinued after five consecutive scores of 0.

The Block Design subtest contains 11 items, consisting of two-dimensional, red-and-white pictures of abstract designs. Examinees must use red and white blocks to assemble a design identical to that in the picture. The patterns are arranged in order of increasing difficulty—four blocks are used for the first eight designs, and nine blocks are used for the last three designs. All items are timed: items 1 to 4 are given a maximum of 45 seconds each; items 5 to 8, 75 seconds; and items 9 to 11, 120 seconds. Items 1 to 3 are scored 2, 1 or 0; items 4 to 11 receive 4 points for a correct completion and up to 3 additional time-bonus points for quick evaluation. The subtest is discontinued after three consecutive scores of 0.

The results showed a significant interaction effect between group and pre- and post-test ($p>0.001$). Both groups had the same level of performance pre-test (average verbal IQ: 22.4 vs 22.9) but the neuroscientific software group (26.9) outperformed the present invention control group (24.3) post-test. In FIG. 29, the verbal IQ score average of both groups can be seen. Moreover, FIG. 30 shows how this experimental effect is spread across the neuroscientific software group; almost every child improved his IQ score over the children in the control group for which changes were random (1/3 positive change; 1/3 no change; 1/3 negative change). This Rhyming test is related to phonological awareness: early reading achievement. In this test, the child's ability to provide a rhyming word when given a stimulus word was assessed. Thirty children in both groups were analyzed pre- and post-test. Performance in both groups were similar to pre-test ($p>0.24$; t-test) but not post-test ($p<0.05$; t-test). The training group (Before: 9; After: 12) outperformed the control group (Before: 8; After: 9). Example results from this test is shown in FIG. 31.

The Visual Auditory Learning test is related to phonological awareness and assessed the participant's ability to generalize knowledge of sound/symbol correspondence and to blend sounds into unknown words. Results suggest a significant difference between the groups post-test ($p<0.05$) and not before. Groups scored similar performance pre-test but post-test, the training group outperformed the control group. After the training, children (in music) made fewer mistakes than the control group in Visual Auditory Learning test. An example of the test results for the 2 groups is shown in FIG. 32.

Only 9 subjects in the musical exercise training group were analyzed using brain imaging, pre- and post-test, to examine effects of the training on attention. Examples of these results are shown in FIGS. 33 and 34. The brain data were recorded during a Go/Nogo task in which participants pressed a button when they saw a white shape and did not press a button when they saw a purple shape. In the Go condition, no differences were observed pre- and post-test. However, a significant peak amplitude difference (pre vs post training) was observed (Pre: 7.3.microvolts; Post: 11.6 microvolts; $p<0.05$) at the "P2" ERP component. The P2 component is related to conflict/decision brain processing. The training seems to have modified brain processes related to conflict resolution. The results of the study also showed that brain modification in the attention task positively correlate with Verbal IQ score ($r=0.44$; $p<0.5$).

In conclusion, the data obtained in this example study provide strong scientific support for the efficacy of the training embodied in the present invention. It has been demonstrated that the training exercises significantly improved intelligence, language and attention skills as reflected with behavioral and brain imaging results. Importantly, the success rate of the training technology was extremely high with over 90% of subjects showing an improvement in intelligence score after the training period.

The above results were obtained in developmentally and cognitively normal children. However, by changing the curriculum 601 the training of the present invention can be utilized on a number of populations, and various age groups, in order to provide various types of training and rehabilitation. The following material discloses methods by which training parameters may be adjusted to obtain the desired results.

Curriculum

The system and method may be tailored to deliver training that focuses upon stimulating brain areas involved in specific skills sets. The training may be adjusted to more specifically train language, attention, memory, motor and intelligence skills in individual users through the use of music exercises such as discriminating sound, singing and producing sounds and movements related to sounds. One reason for this is that scientific studies done by Sylvain Moreno have shown that skills obtained from undergoing musical-based exercises may provide generalized benefit to a number of cognitive skills. This may effect may be more pronounced when the music-based exercises are designed according to the current invention in order to focus on particular aspects of cognition.

Figure 42:
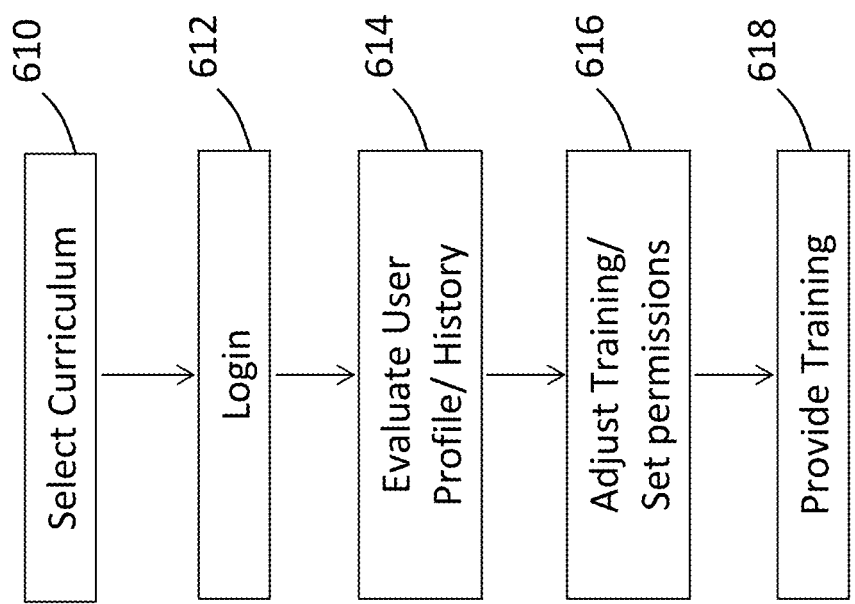
FIG. 42 is a flow chart showing the training program operation including management and adjustment of training which may occur according to a selected training curriculum and the profile or history of a user.

The present invention may include methods for, and computer software to, adapt the training parameters according to specific disorders to be treated or skills which are specifically targeted. The appropriate training exercises and parameters may be selected by the user or administrator choosing a specific curriculum 610, as shown in FIG. 42, which may occur in an independent step 610, or as part of the login process 612, including being automatically selected according to user information entered.

Default curriculums for elderly, young adult, or child users may be appropriate for a large sample of the population. The present invention may also provide curriculums designed to specifically improve verbal intelligence, attention, reading and language skills, to improve their learning capabilities and their potential cognitive achievements. Curriculums can be defined for individuals either with or without various pathology.

A memory curriculum can be used to focus upon memory training. In one embodiment of the present invention, a method for adaptively training a subject to improve his memory by using questions, sounds, words, melodies, songs, images and objects may be provided. For example, this aspect of the invention may be presented as a memory module, or other training component.

An IQ curriculum can be used to focus upon tasks pinpointing general intelligence. In one embodiment of the present invention, a method for adaptively training a subject to improve his/her intelligence score may be provided.

An Executive Function curriculum can be used to focus upon tasks that involve executive function. In yet another embodiment of the present invention, a method for adaptively training a subject to improve executive function may be provided. For example, tasks related to control, attention, inhibition, switching brain processes, may be provided by tasks using acoustic, visual and verbal stimuli, which may occur in timed manner and with various types of feedback.

A Verbal Intelligence curriculum can be used to improve verbal intelligence, attention, reading and language skills.

An Impaired Verbal Intelligence curriculum can be used to provide a training strategy designed to attempt to rapidly and progressively improve the verbal intelligence, attention, reading and/or language skills in individuals that have suffered brain damage or brain abnormal development.

An Elderly curriculum may provide a training strategy designed to attempt to rapidly and progressively improve the verbal intelligence, attention, reading and language skills in individuals who have undergone age-related or disease related deterioration of their verbal intelligence, attention, reading and language processing abilities.

A Hearing Loss curriculum, may provide training which is designed to promote increasing discrimination of language, speech sounds, and other sound characteristics. This may be used as a means for compensation, retraining, and rehabilitation due to various types of central or peripheral hearing loss, especially when related to speech perception, sound discrimination, and other types of loss. An Auditory-Processing Deficit curriculum may provide exercises that target exercises that train or retrain processing which can compensate for specific auditory processing deficits.

A Language discrimination curriculum, may also be provided which is designed to provide sound and language discrimination in the learning of a foreign language.

In one embodiment of the present invention, a method of increasing the ability of a user to process aurally received signals may be disclosed. The method may include multiple steps. The steps are adjusted depending on the characteristics of the user. For example, the method may include the following of 6 exercise categories in one session out of X number of total sessions: Rhythm perception and production, voice/sound production, audio discrimination, singing discrimination and production, conceptualization of knowledge and creation of new concepts related to music production. The training may adapt the difficulty and the steps of the method depending upon the user's performance, for example, such as is indicated by the tracking progress module 592 of the present invention that is operable to analyze and determine a user's performance.

The present invention may also use a modified version of this training strategy as a method for screening human populations to identify those individuals who would benefit from this invention.

Lastly, an Evaluation curriculum can be used to assess certain traits of a user in order to determine aspects of subsequently presented training. For example, assessing that a user is very good at rhythm production may indicate that exercises related to this skill be de-emphasized by the training. Other areas where the user performance is not as good can suggest that these would receive increased benefit from the training. Initial training parameters and settings related to training progression may be set according the performance results of a user while undergoing an Evaluation curriculum. Evaluation curriculum may also be used by a user to assess their baseline characteristics. For example, a user may not realize that their memory skills are somewhat lower than they should be. By assessing the user across a number of training areas, selected areas of training can be provided within a curriculum. The Evaluation curriculum may also be used to pinpoint brain networks which are showing a deficit. By evaluating user performance across a set of training tasks, particular brain regions or networks may be judged by the software to be in deficit, and subsequent training curriculums may be adjusted.

Logging In. The curriculum and training components and parameters may be adjusted based upon a user profile generated when a user logs into the training. Generally, when a user initiates use of the present invention, a user will log in 612 to identify themselves to the training program. The log in process may take several forms, for example, in one embodiment of the present invention the user may provide identifying information. The login process may also include the user being asked to choose an avatar that will represent them during the training. A large variety of log-in options may be presented to a user, in accordance with specific presentation of the present invention including the method by which the training is delivered, for example, such when the user does the training remotely the user may be queried as to whether the user is using a laptop with software locally installed, is using a website presentation, is receiving the training using an e-reader, a tablet, etc. The device or mode of remote presentation may also be automatically detected.

Once a user is logged on, the present invention may search for information relating to any prior use of the present invention by the user by using the database module 570 to search the database 94, 96 evaluate a user profile 614. For example, such information may provide guidance to the training manager 574 regarding the possible levels of use that the user will undertake. If no such information is provided the training manager 574 will choose a starting level for the user, or may provide a basic initial level exercise provided to all first-time users. The basic initial level exercise may be utilized to determine the level of the user. All new users may be asked to create a profile so that their training can be tracked across multiple sessions. An exercise manager may guide a user through exercises based upon their profile and curriculum parameter values.

User Profile. In this embodiment training parameters stored in a database 94, 96 related to the exercises, lessons, modules and levels of difficulty of each may be designed or adjusted 616 to train users of that age, and adjusted according to the user's profile stored in the database 94,96. In another embodiment of the present invention, a training system may be specially tailored to young or old users, such as adjusting reaction time expectations and lesson duration or timeout intervals. The system may include the provision of musical training exercises 618 at adjusted levels of difficulty in response to the user's performance. The training system may be provided in a computer game or video game format that is tailored to the attention span, interests, and various capacities of young children. This system may cause users to attain cognitive and/or musical skills in a manner which is entertaining and self-rewarding.

Users of other ages may utilize alternative embodiments of the present invention, and that the exercises, lessons and/or modules, and the difficulty of each of these, may be designed to train users of other ages. Further, the exercises may be set or adjusted 616 to train users with particular developmental, physical, or cognitive, sensory, or other limitations. Although the changes according to these limitations may be made through adjusting the parameters related to various characteristics of the exercises, these may also be made by adjusting the types of exercises presented to a user 618, such as by limiting the categories of exercises, the number of repetitions used for various stimuli, and difficulty parameters which may be modulated 616.

One embodiment of the present invention, may incorporate a system and method for enabling both normal and individuals with speech, language and reading based communication disabilities (due to auditory or cognitive processing problems or developmental problems such as low intelligence and attention disabilities), to improve their brain processing in relation to language, attention, memory and intelligence, among other skill sets.

The present invention may include methods for, and computer software to, adapt the method parameters related to duration, intensity, speed of presentation, category, and difficulty level to a user based upon performance.

Alternative Embodiments

As shown in FIG. 41, the current invention can be realized using devices such as a computer tablet 450, having conventional user interface components such as a speaker, webcam, microphone, and ports for wired and wireless connection to various devices that may be used as part of the training, as well as internet connectivity to access and send data to remotely located components of the invention.

In one embodiment, the visual display 456 may present the training in a central area 454 oriented towards a user located at the top portion of the figure who responds to virtual buttons provided on the screen 452*a*. When a second player uses the training as well then a second response portion 452*b* may be provided. The orientation of the training within the central area 454 may adjust according to the user who undergoes the training at any particular time. Alternatively, it is obvious that the orientations are possible so that both players can play simultaneously, such as re-orienting the training by 90 degrees so that both players may easily see the training. Players may interact with the training sequentially. Their performances evaluated by the performance module 590 and are stored separately in the database 570 according to 2 different user profiles 604.

Selected Advantages of the Training.

The current invention provides cognitive training using music-based exercises that are unique from traditional music training in many respects. No musical instrument is required. It does not rely upon lessons of "units" of music to be played which are adjusted in duration and content based upon improvement in musical performance of a student. In musical training, normally harder difficulty pieces include more information, harder manual dexterity operations, and do not focus on particular sensory and cognitive processing skills, or at least do not divorce these from the performance of music. Nor are conceptual and perceptual difficulty modulated independently from musical performance in traditional musical training. In fact it is normally the opposite. Further, in music training the exercises usually comprise both reading and playing a musical score. The behavior of the student itself is judged as acceptable or unacceptable, and what a student "thinks" about the stimuli is not much considered or used in training. This is because the primary intention of musical training is to teach a student to play an instrument.

In the current invention exercises often involve judgments and choices that must be made about cues, probes, and candidate musical components. Further the task may be realized within a background which may provide different contexts. The background components may be antithetical to learning to play an instrument, but may be invaluable in teaching cognitive-sensory skills related to attention and stimulus processing. The current training is not directed to solving inefficiency or monotony in musical training and rather is directed to cognitive training and solving the problem that teaching children various primary skills, relate to enhancing cognitive ability, is usually difficult and boring for the children.

Although musical exercises in formal musical training may require a student to concentrate on various aspects of pitch, timing, or other characteristic of the music in order to develop a particular musical skill, the exercises themselves are not designed to emphasize these particular aspects, individually. Rather, the same musical piece may be used and the student is simply asked to concentrate on particular aspects of the musical task. Typically, different songs/pieces of music are not specifically created to emphasize, for example, developing skills related to detection or differentiation of pitch or timing. For example, a beat is not intentionally held constant while difficulty in pitch is modulated or vice-versa.

Many of the training components of the current training each have at least one task which requires the user to make a response that is a choice about musical stimuli that are presented to the user. After a musical exercise has been presented to a subject, the subject may be provided with additional training modules that evaluate the student's knowledge on any aspect of the training including mathematical, linguistic, grammatical, reference, or abstract knowledge that was imparted during the exercise. Unlike musical training, the exercises of the current invention typically are not repeated more than a few times before a different exercise is presented. In one embodiment, training does not expose users to a tedious task that is repeated without variety. For example, the approach of strict repetition may be avoided both by maximally presenting specific components of the exercises 3×, and also be alternating between, at least 2 exercise types. The music aspect of a task may be secondary. For example, in a singing task the users may not be given feedback related to their singing. This task may have alternative cognitively-oriented goals such as using lyrics that become more and more difficult terms of grammar, grade level, or other aspect.

With respect to training developmentally challenged individuals, the current invention provides training that is not limited by physical constraints, or at least less so than with musical production since difficulty level is independently varied from production. Manual dexterity and also musical skill, which normally serves to constrain the user during musical training, may be circumvented as limiting issues. Hence the invention overcomes the problem encountered when a user conceptually understands musical concepts well but is not able to play an instrument sufficiently, which might otherwise provide for a situation in which the training cannot progress. When the object is to train for general cognitive concepts and skills rather than simply trying to train a user to play an instrument, then the conventional music training may lead to large amounts of repetition without the user deriving benefit for cognitive skills.

Other advantages of the invention are to provide training that does not require the ability to read musical notation. There are many students who do not know how to read music or who may suffer from various learning disorders or reading problems such as dyslexia. Both of these groups would encounter considerable trouble using conventional types of musical training.

Accordingly, the current invention provides cognitive based training by using musical exercises which are designed to promote specific musical skills and which are not designed to teach a student to play a musical instrument. Unlike the prior art, even if a student used the invention for 20 years, they still may not become proficient at playing a musical instrument since this is not the object of the training. The intention of the musical training of the current invention is to selectively provide exercises that concentrate on particular cognitive, linguistic and perceptual skills.

What is claimed is:

1. A cognitive training method comprising:
establishing a processor for storing a plurality of exercise category data, each of said exercise category data having a plurality of task data, each of said plurality of task data having a plurality of levels of difficulty data;
said processor configured to present cognitive training to a user in order to improve cognitive skills of the user by operating a training manager module for transmitting, a selected exercise category from said plurality of exercise categories data, a selected task from said plurality of task data having a selected level of difficulty from said plurality of levels of difficulty data in said processor and having a visual display and an audio transducer;
said processor being further configured to operate a user interface module for actuating a user interface to accept user input data from a user in response to said selected task;
sending said user input data from said user interface to said processor;
said processor being further configured for operating the training manager module to:
store said user input data as both user input data and user parameter data and evaluate said user input data using an evaluation module algorithm, and based upon the evaluation of said user input data, adjust a subsequent level of difficulty associated with said selected task, wherein if a tracking progress module determines a selected performance rate of correct user input data is above a predetermined correct data threshold then said level of difficulty is adjusted responsive to said evaluation of said user input data;
adjust values of a plurality of training parameters, at least partially in accordance with and responsive to said stored user parameters; and,
transmit to the user interface and to the user responsive to (1) said user parameters, and (2) said adjusted values of exercise and training parameters, at least one training task selected to include at least one cue stimulus, at least one probe stimulus, and at least one distractor stimulus for interfering with the probe and cue stimuli presented to the user, whereby task difficulty is adjustable as a function of:
difficulty of said cue stimulus, difficulty of said probe stimulus, and difficulty of said at least one distractor stimulus, said distractor stimulus being an independent stimulus with respect to said probe stimulus and said cue stimulus, wherein the distractor stimulus comprises at least one stimulus presented to said user during at least a portion of time interval when said probe stimulus is presented to said user, as a background for distracting the user from at least one of the cue stimulus and the probe stimulus.

2. The method of claim 1, wherein the difficulty of the cue stimulus is adjusted by at least one of: adjusting a predetermined number of stimulus components of the cue stimulus, and adjusting a length of a sequence of tones, and adjusting a complexity of a tonal sequence.

3. The method of claim 1, wherein a difficulty of the cue stimulus is adjusted by at least one of: complexity of a predetermined number of components of a scene, a predetermined number of colors used in the cue stimulus, and the complexity of the scene.

4. The method of claim 1, wherein a difficulty of the cue stimulus is adjusted using at least one of: language grade level, a song lyrics difficulty, and a grade level of the concepts which are being trained.

5. The method of claim 1, wherein the difficulty of the probe stimulus is adjusted by at least one of: a time delay between the cue and probe stimulus, and a time duration of the probe stimulus.

6. The method of claim 1, wherein the difficulty of the distractor stimulus is adjusted by at least one of: adjusting the similarity between at least one distractor stimulus that is presented with the cue stimulus; and, adjusting a predetermined number of distractor stimuli that are presented with the cue stimulus.

7. The method of claim 1, wherein the difficulty of the distractor stimulus is adjusted by at least one of: adjusting the similarity between at least one distractor stimulus that is presented with the probe stimulus and the cue stimulus, adjusting a predetermined number of distractor stimuli that are presented with the probe stimulus, and, adjusting the intensity of at least one distractor stimulus that is presented with the probe stimulus.

8. The method of claim 1, wherein the difficulty of the cue stimulus is adjusted by at least one of: adjusting a complexity of a tonal sequence, adjusting a rhythm, adjusting a tempo, and, adjusting the difference between musical notes.

9. The method of claim 1, wherein the cue stimulus and probe stimulus are visual.

10. The method of claim 1, wherein the cue stimulus and probe stimulus are auditory.

11. The method of claim 1, wherein the cue stimulus and probe stimulus are cross-modal.

12. The method of claim 1, wherein the cue stimulus and at least one distractor stimulus are audiovisual.

13. The method of claim 1, wherein the cue stimulus and at least one distractor stimulus are cross-modal.

14. The method of claim 1, wherein the user input data for the selected task is measured using at least one of the following group selected from: a motion sensor, accelerometer, and a position sensor.

15. The method of claim 1, wherein the user input data for the selected task is measured using a microphone.

16. The method of claim 1, wherein the user input data for the selected task is measured using a touch sensitive drawing screen.

17. The method of claim 1, wherein the user input data for the selected task is measured using a first user response area and a second user response area of a touch sensitive visual display whereby at least one of the first and second user responds to training exercises.

18. The method of claim 1, wherein the step of evaluating the user input data includes evaluating Go/No-Go task data.

19. The method of claim 1, wherein the evaluation of the user input data is used to provide the user with feedback.

20. The method of claim 19, wherein the feedback is selected from the set of feedback types selected from the group of: positive feedback, no feedback, and neutral feedback; and in the case of a neutral feedback then requesting that the user to "try again" by providing up to N additional user input responses, where N is set to 2 or 3.

21. The method of claim 1, wherein the level of task difficulty is selected from the group of: perceptual and conceptual.

* * * * *